US012612402B2

(12) United States Patent
Zhou et al.

(10) Patent No.: US 12,612,402 B2
(45) Date of Patent: Apr. 28, 2026

(54) NITROGEN-CONTAINING FUSED HETEROCYCLIC COMPOUNDS OF N-SULFONAMIDE AND USE THEREOF

(71) Applicant: NUTSHELL THERAPEUTICS (SHANGHAI) CO., LTD., Shanghai (CN)

(72) Inventors: Guoqiang Zhou, Shanghai (CN); Liting Yu, Shanghai (CN); Caiming Xi, Shanghai (CN)

(73) Assignee: NUTSHELL THERAPEUTICS (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 19/026,681

(22) Filed: Jan. 17, 2025

(65) Prior Publication Data

US 2025/0304578 A1 Oct. 2, 2025

Related U.S. Application Data

(63) Continuation-in-part of application No. PCT/CN2024/125849, filed on Oct. 18, 2024.

(30) Foreign Application Priority Data

Oct. 20, 2023 (CN) ......................... 202311366942.7
Dec. 22, 2023 (CN) ......................... 202311783867.4
Mar. 7, 2024 (CN) ......................... 202410262235.1
Sep. 11, 2024 (CN) ......................... 202411275395.6

(51) Int. Cl.
*C07D 471/04* (2006.01)
*A61K 31/4545* (2006.01)
*A61K 31/506* (2006.01)
*A61P 35/00* (2006.01)
*C07B 59/00* (2006.01)

(52) U.S. Cl.
CPC ........ *C07D 471/04* (2013.01); *A61K 31/4545* (2013.01); *A61K 31/506* (2013.01); *A61P 35/00* (2018.01); *C07B 59/002* (2013.01); *G01N 2333/4748* (2013.01)

(58) Field of Classification Search
CPC ... C07D 471/04; A61P 35/00; A61K 31/4545; A61K 31/506; C07B 59/002; G01N 2333/4748
See application file for complete search history.

(56) References Cited

U.S. PATENT DOCUMENTS

2017/0240525 A1 8/2017 Vu et al.
2019/0119249 A1 4/2019 Vu et al.
2021/0002252 A1 1/2021 Vu et al.
2022/0213062 A1 7/2022 Vu et al.
2022/0315564 A1 10/2022 Vu et al.
2023/0033324 A1 2/2023 Levine et al.
2023/0044826 A1 2/2023 Dumble
2023/0049952 A1 2/2023 Levine et al.
2023/0301975 A1 9/2023 Vu
2023/0312539 A1 10/2023 Vu et al.
2024/0269126 A1 8/2024 Levine et al.
2024/0342151 A1 10/2024 Vu
2024/0400591 A1 12/2024 Li et al.

FOREIGN PATENT DOCUMENTS

EP 4559917 A1 5/2025
WO 2021061643 A1 4/2021
WO 2022213975 A1 10/2022
WO 2023196993 A1 10/2023
(Continued)

OTHER PUBLICATIONS

Gura et al., Systems for Identifying New Drugs are Often Faulty. Science, New Series, (1997), 278(5340), 1041-1042 (Year: 1997).*
(Continued)

*Primary Examiner* — Renee Claytor
*Assistant Examiner* — Christopher Lindsay Johnson
(74) *Attorney, Agent, or Firm* — Houston Beshining Law Office PLLC; Liangang Ye

(57) ABSTRACT

The present disclosure discloses a class of nitrogen-containing fused heterocyclic compounds of N-sulfonamide and the use thereof. The nitrogen-containing fused heterocyclic compounds of N-sulfonamide of the present disclosure are compounds of formula I, isotope-labeled compounds thereof, solvates thereof, pharmaceutically acceptable salts thereof, solvates of the pharmaceutically acceptable salts thereof. Such compounds can promote the binding of p53 Y220C mutant with DNA and possess better inhibitory activity against the proliferation of cancer cells.

I

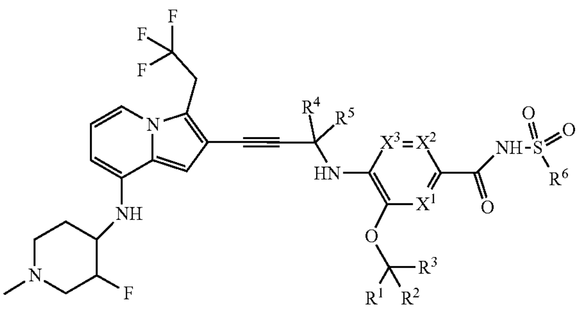

15 Claims, 4 Drawing Sheets

Specification includes a Sequence Listing.

(56) References Cited

FOREIGN PATENT DOCUMENTS

| | | | |
|---|---|---|---|
| WO | 2024086809 | A1 | 4/2024 |
| WO | 2024120471 | A1 | 6/2024 |

OTHER PUBLICATIONS

Johnson et al., Relationships between drug activity in NCI preclinical in vitro and in vivo models and early clinical trials. British Journal of Cancer, (2001), 84(10), 1424-1431 (Year: 2001).*

Pfister et al., Transcriptional Regulation by Wild-Type and Cancer-Related Mutant Forms of p53. Cold Spring Harbor perspectives in medicine, (2017), 7(2), a026054 (Year: 2017).*

Jun. 9, 2025 Taiwan First Office Action issued in Taiwanese Patent Application No. 11420610410.

Alexandrova E M et al. p53 loss-of-heterozygosity is a necessary prerequisite for mutant p53 stabilization and gain-of-function in vivo. Cell Death Dis, 2017, 8(3): e2661-e2661.

Levine A J. Targeting therapies for the p53 protein in cancer treatments. Annu Rev Cancer Biol, 2019, 3: 21-34.

Boettcher S et al. A dominant-negative effect drives selection of Tp53 missense mutations in myeloid malignancies. Science, 2019, 365(6453): 599-604.

Chen S et al. Arsenic trioxide rescues structural p53 mutations through a cryptic allosteric site. Cancer cell, 2021, 39(2): 225-239.

Zhang S et al. Advanced Strategies for Therapeutic Targeting of Wild-Type and Mutant p53 in Cancer. Biomolecules. 2022, 12(4):548.

Martins C.P., Brown-Swigart L., Evan G.I. Modeling the Therapeutic Efficacy of p53 Restoration in Tumors. Cell. 2006; 127:1323-1334.

Joerger A C et al. Structural basis for understanding oncogenic p53 mutations and designing rescue drugs. Proc Natl Acad Sci, 2006, 103(41): 15056-15061.

Boeckler F M, et al. Targeted rescue of a destabilized mutant of p53 by an in silico screened drug. Proc Natl Acad Sci, 2008, 105(30): 10360-10365.

English translation of Chinese Priority Application No. 2023113669427.

English translation of Chinese Priority Application No. 2023117838674.

English translation of Chinese Priority Application No. 2024102622351.

English translation of Chinese Priority Application No. 2024112753956.

* cited by examiner

NITROGEN-CONTAINING FUSED HETEROCYCLIC COMPOUNDS OF N-SULFONAMIDE AND USE THEREOF

CROSS-REFERENCE TO RELATED APPLICATIONS

The present application is a Continuation-in-part Application of International Application No. PCT/CN2024/125849, filed on Oct. 18, 2024, which claims the right of the priorities of Chinese patent application 2023113669427 filed on Oct. 20, 2023, Chinese patent application 2023117838674 filed on Dec. 22, 2023, Chinese patent application 2024102622351 filed on Mar. 7, 2024, and Chinese patent application 2024112753956 filed on Sep. 11, 2024. The contents of the above Chinese patent applications are incorporated herein by reference in their entireties.

REFERENCE TO SEQUENCE LISTING

The present application contains Sequence Listing as an XML file entitled "P24417159US-CIP-2-SEQ" created date of Jan. 7, 2025, and having a size of 1794 bytes.

TECHNICAL FIELD

The present disclosure belongs to the pharmaceutical field, further belongs to the pharmaceutical field of p53 Y220C pocket binding agent with druggability, and particularly relates to a class of nitrogen-containing fused heterocyclic compounds of N-sulfonamide and the use thereof.

BACKGROUND

The protein product of TP53 gene (p53) is currently considered as one of the most important tumor suppressor factors. Unlike RB1, CDKN2A, and PTEN, which are lost in tumors through homozygous deletion, TP53 is often found to have somatic missense mutations (Alexandrova E M et al. "p53 loss-of-heterozygosity is a necessary prerequisite for mutant p53 stabilization and gain-of-function in vivo". *Cell Death Dis,* 2017, 8(3): e2661-e2661). However, so far, the targeting therapy of p53 mutations has not been validated in clinical treatment (Levine A J. "Targeting therapies for the p53 protein in cancer treatments". *Annu Rev Cancer Biol,* 2019, 3:21-34). Cells with TP53 mutations accumulate high levels of mutant p53 protein, which exerts dominant-negative effects on wild-type (WT) p53 and its homologous proteins p63 and p73, causing them to lose their normal regulatory functions on cell cycle and apoptosis (Boettcher S et al. "A dominant-negative effect drives selection of Tp53 missense mutations in myeloid malignancies". *Science,* 2019, 365(6453): 599-604). Experimental results of conditional regulation of p53 expression in mouse tissues indicated that restoration of p53 expression could inhibit lymphoma and sarcoma growth through apoptosis in different mouse models (Martins C. P., Brown-Swigart L., Evan G. I. "Modeling the therapeutic efficacy of p53 restoration in tumors". *Cell.* 2006; 127:1323-1334), providing a theoretical basis for leveraging the restoration of p53 normal function for tumor treatment. In addition to enhancing wild-type p53 activity in tumors with intact Tp53 genotypes, restoring wild-type protein function in tumors expressing mutant p53 is also a promising strategy for cancer treatment (Chen S et al. "Arsenic trioxide rescues structural p53 mutations through a cryptic allosteric site". *Cancer cell,* 2021, 39(2): 225-239. e8).

The core domain of wild-type p53 is unstable, with poor thermodynamic and kinetic stability, allowing for rapid transformation between folded and unfolded states. Mutation of p53 core region residues leads to enhanced thermodynamic and kinetic instability, thereby causing the core DNA-binding domain to lose DNA-binding activity. Such effects can be used to design ligands that selectively bind to the native state of p53 protein to reverse the thermodynamic and kinetic denaturation caused by these mutations (Zhang S et al. "Advanced strategies for therapeutic targeting of wild-type and mutant p53 in cancer". *Biomolecules.* 2022, 12(4): 548). It is worth noting that the special Y220C mutation mediates the formation of a surface pocket away from the core DNA-binding domain (Joerger A C et al. "Structural basis for understanding oncogenic p53 mutations and designing rescue drugs". *Proc Natl Acad Sci,* 2006, 103(41): 15056-15061), rendering it an ideal target for treating tumors harboring this mutation. So far, many Y220C pocket binding agents have been developed to stabilize this p53 mutant and reactivate its transcriptional activity, but with limited efficacy (Boeckler F M, et al. "Targeted rescue of a destabilized mutant of p53 by an in silico screened drug". *Proc Natl Acad Sci,* 2008, 105(30): 10360-10365). Therefore, for tumor patients with p53 Y220C mutation, there is an urgent need to develop p53 Y220C pocket binding agents with stronger affinity and better druggability.

BRIEF SUMMARY OF THE INVENTION

The technical issue to be solved by the present disclosure is the poor druggability of existing p53 Y220C pocket binding agents. For this reason, the present disclosure provides a class of nitrogen-containing fused heterocyclic compounds of N-sulfonamide and the use thereof. This class of compounds can promote the binding of p53 Y220C protein with DNA and possess better inhibitory activity against the proliferation of cancer cells represented by gastric cancer cells.

The present disclosure provides a nitrogen-containing compound of formula I, an isotope-labeled compound thereof, a solvate thereof, a pharmaceutically acceptable salt thereof, or a solvate of the pharmaceutically acceptable salt thereof,

I

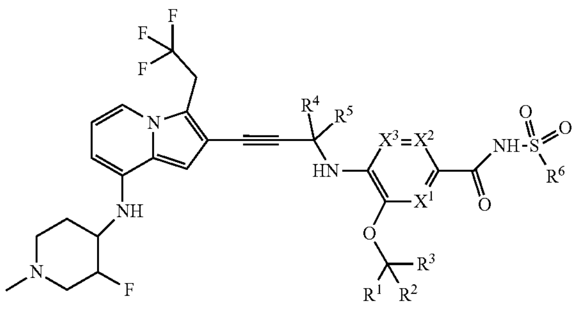

wherein

- $X^1$, $X^2$, and $X^3$ are each independently selected from CH and N;
- $R^1$, $R^2$, $R^3$, $R^4$, and $R^5$ are each independently selected from hydrogen and deuterium;

$R^6$ is —$(CH_2)$, $R^7$;

n is 0, 1, 2, or 3;

$R^7$ is selected from $C_1$-$C_6$ alkyl, deuterated $C_1$-$C_6$ alkyl, $C_1$-$C_6$ haloalkyl, and $C_3$-$C_6$ cycloalkyl.

As a preferred technical solution, the nitrogen-containing compound of formula I, the isotope-labeled compound thereof, the solvate thereof, the pharmaceutically acceptable salt thereof, or the solvate of the pharmaceutically acceptable salt thereof is a nitrogen-containing compound of formula Ia, an isotope-labeled compound thereof, a solvate thereof, a pharmaceutically acceptable salt thereof, a solvate of the pharmaceutically acceptable salt thereof;

Ia

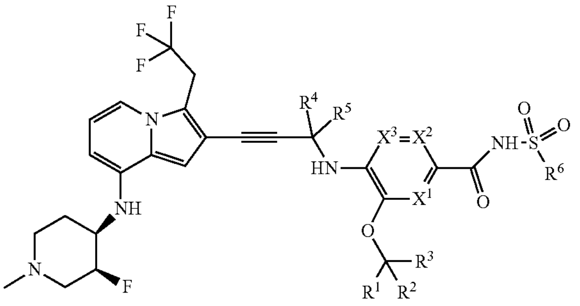

wherein $X^1$, $X^2$, and $X^3$ are each independently selected from CH and N;

$R^1$, $R^2$, $R^3$, $R^4$, and $R^5$ are each independently selected from hydrogen and deuterium;

$R^6$ is —$(CH_2)_nR^7$;

n is 0, 1, 2, or 3;

$R^7$ is selected from $C_1$-$C_6$ alkyl, deuterated $C_1$-$C_6$ alkyl, $C_1$-$C_6$ haloalkyl, and $C_3$-$C_6$ cycloalkyl.

As a preferred technical solution, $X^1$ is N; $X^2$ is CH or N; $X^3$ is CH.

As a preferred technical solution, $X^1$ is N; $X^2$ and $X^3$ are CH.

As a preferred technical solution, $R^6$ is —$(CH_2)_nR^7$; n is 0 or 1; $R^7$ is selected from $C_1$-$C_3$ alkyl, deuterated $C_1$-$C_3$ alkyl, $C_1$-$C_3$ haloalkyl, and $C_3$-$C_6$ cycloalkyl.

As a preferred technical solution, $R^6$ is —$(CH_2)_nR^7$; n is 0 or 1; $R^7$ is selected from —$CH_3$, —$CD_3$, —$CF_3$, and cyclopropyl.

As a preferred technical solution, $R^1$, $R^2$, $R^3$, $R^4$, and $R^5$ are each independently selected from hydrogen and deuterium, and at least one of them is deuterium.

As a preferred technical solution, $R^1$, $R^2$, and $R^3$ are deuterium; $R^4$ and $R^5$ are hydrogen.

As a preferred technical solution, $R^1$, $R^2$, and $R^3$ are hydrogen; $R^4$ and $R^5$ are deuterium.

As a preferred technical solution, the formula I is a formula Ib or Ic;

Ib

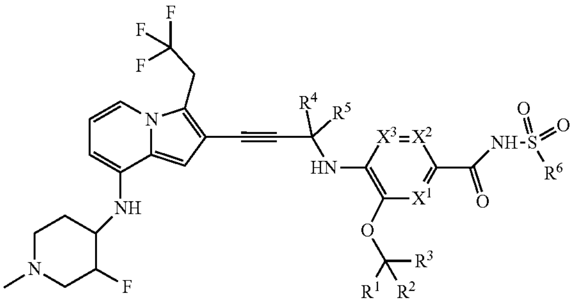

Ic

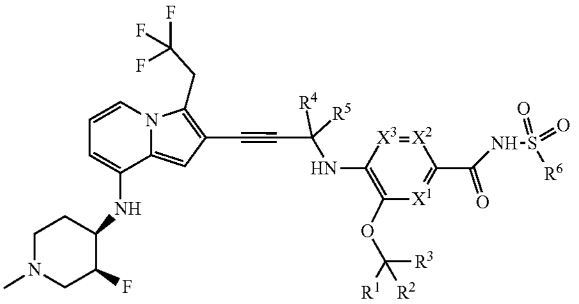

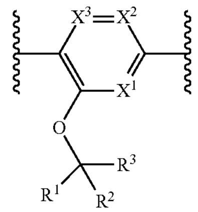

is

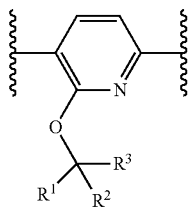

or

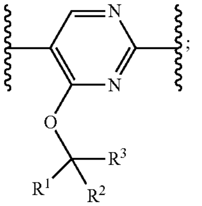

In formulas Ib and Ic, $R^1$, $R^2$, $R^3$, $R^4$, and $R^5$ are each independently selected from hydrogen and deuterium;

$R^6$ is —$(CH_2)_nR^7$;

n is 0 or 1;

$R^7$ is selected from $C_1$-$C_6$ alkyl, $C_1$-$C_6$ haloalkyl, and $C_3$-$C_6$ cycloalkyl.

Preferably,

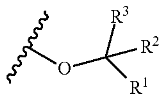

is selected from $—OCH_3$ and $—OCD_3$;
$R^4$ and $R^5$ are selected from hydrogen;
$R^6$ is $—(CH_2)_nR^7$; n is 0 or 1; $R^7$ is selected from $—CH_3$, $—CD_3$, $—CF_3$, and cyclopropyl.
As a preferred technical solution, the compound of formula I is selected from the following compounds:
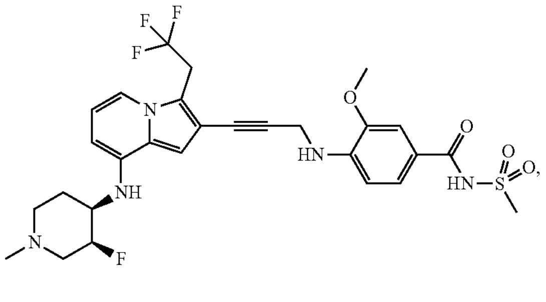
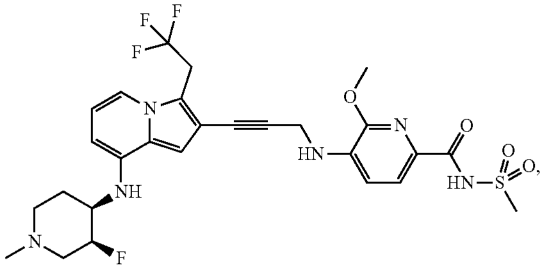
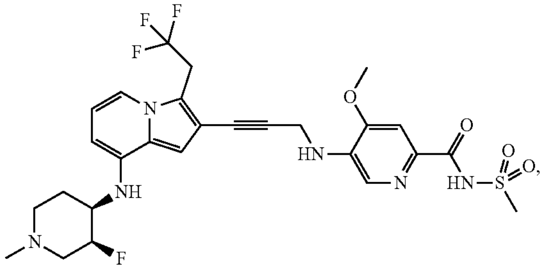
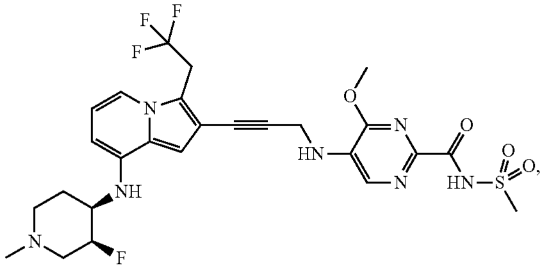
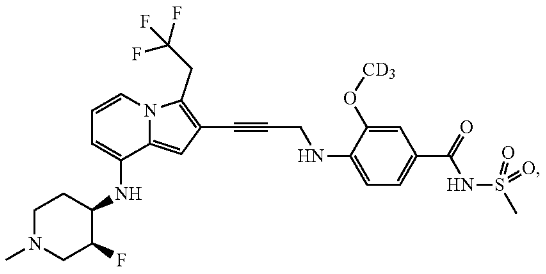
-continued
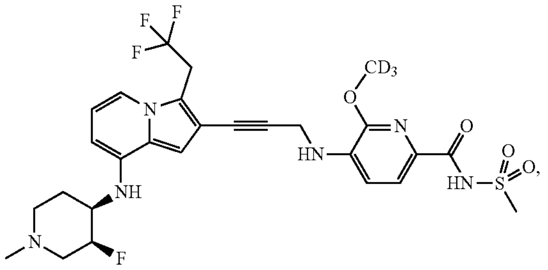
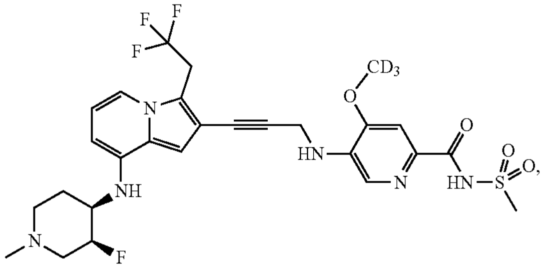
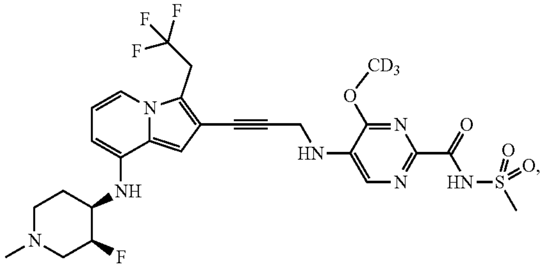
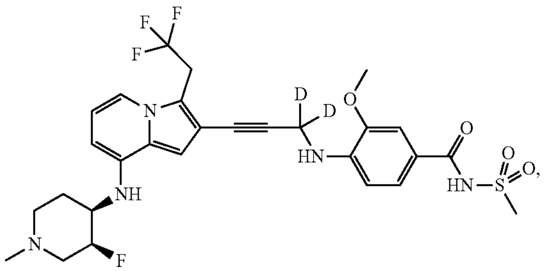
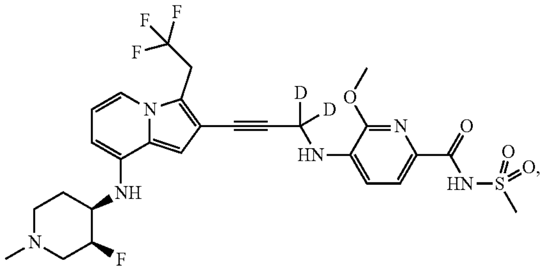
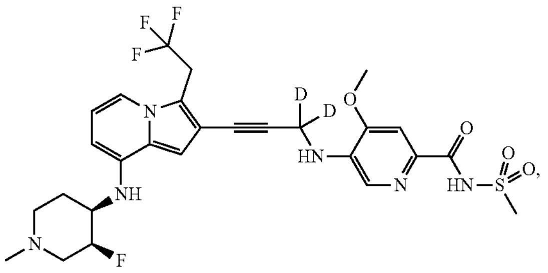

-continued
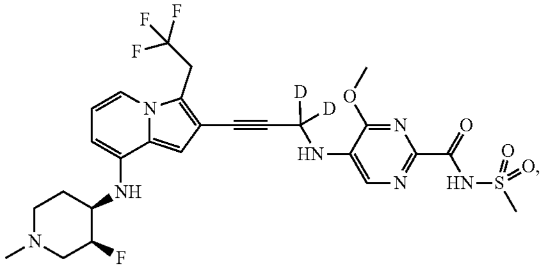,
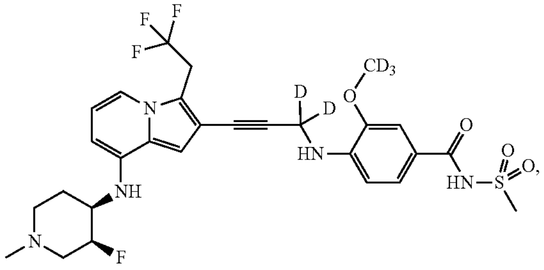,
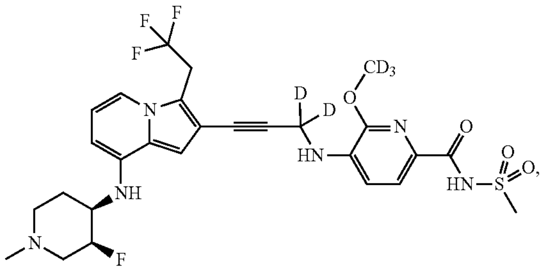,
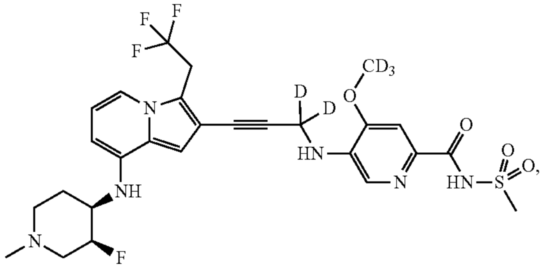,
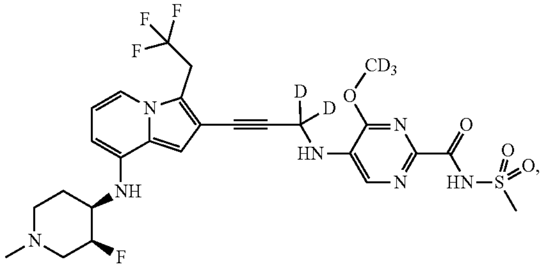,
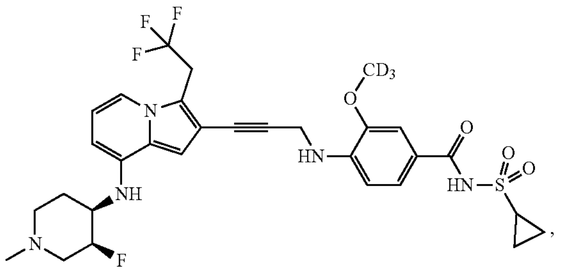,
-continued
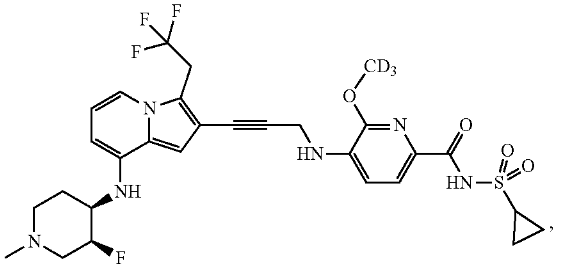,
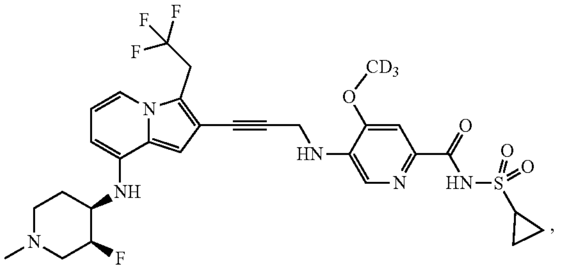,
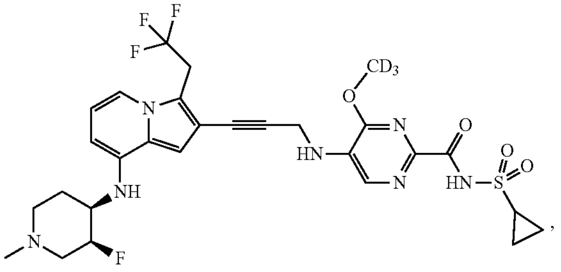,
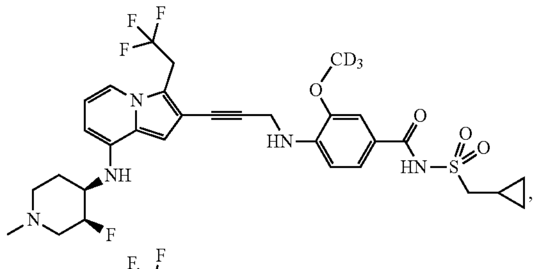,
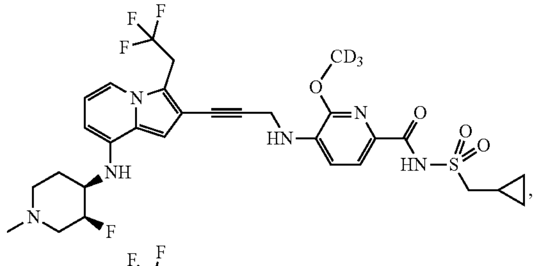,
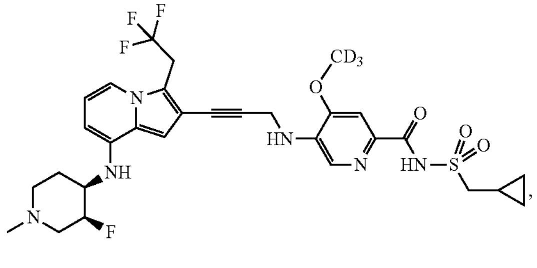, -continued

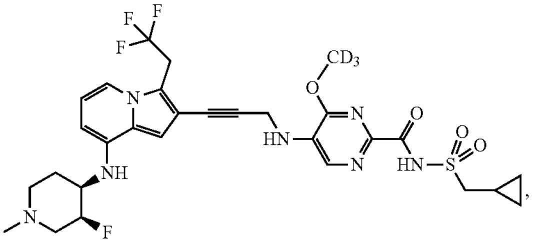

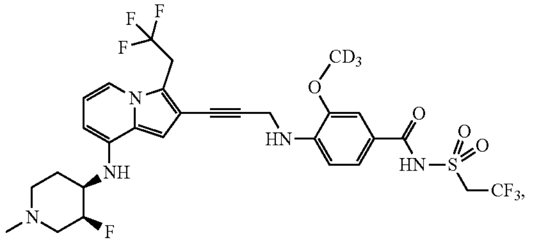

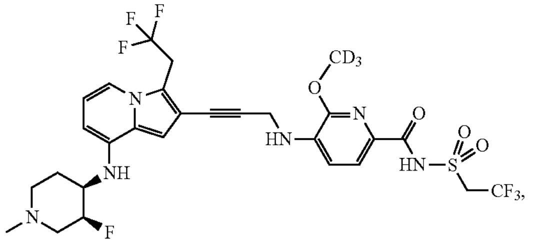

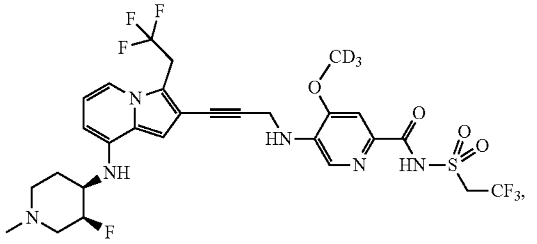

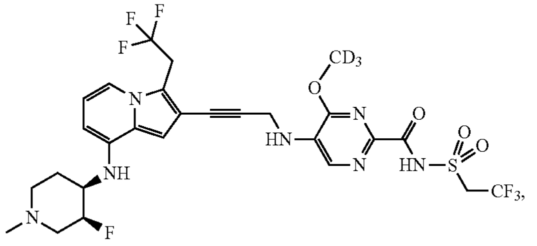

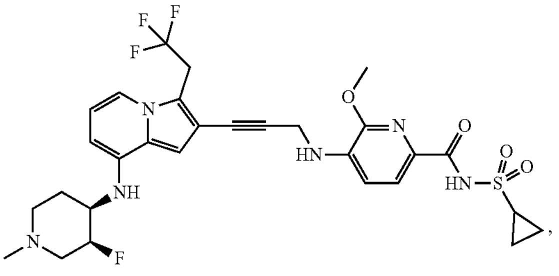

-continued

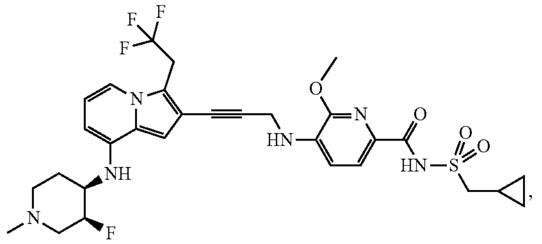

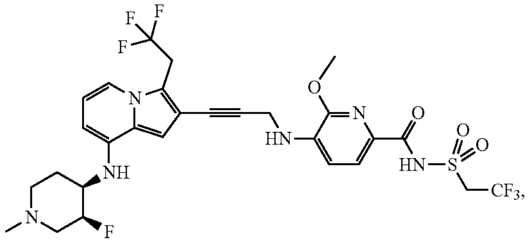

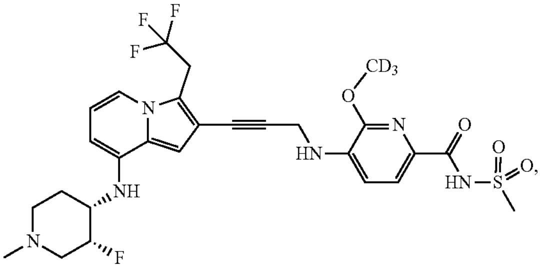

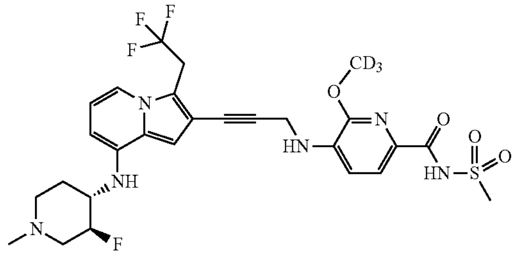

and

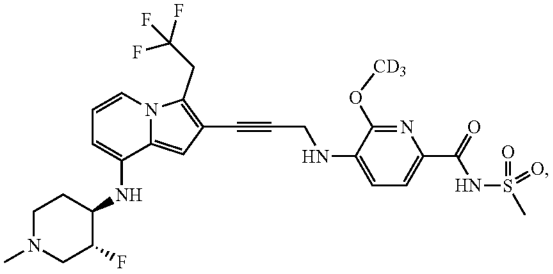

an enantiomer thereof, or a mixture of the two in any ratio (e.g., racemate).

The present disclosure further provides a preparation method for the compound of formula I, the isotope-labeled compound thereof, the solvate thereof, the pharmaceutically acceptable salt thereof, or the solvate of the pharmaceutically acceptable salt thereof. Comprising the following methods:

Method 1:
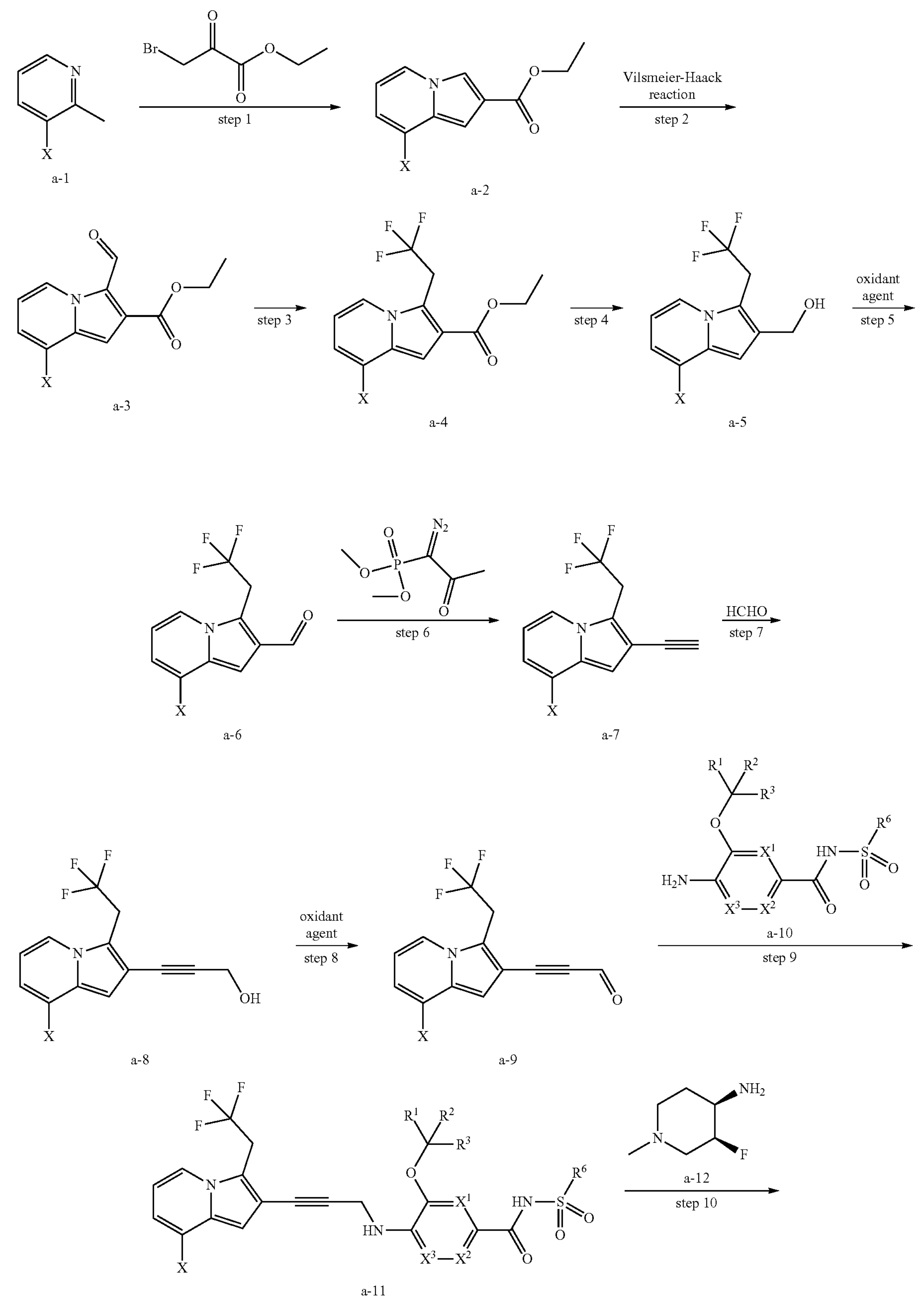
a-1 a-2 a-3 a-4 a-5 a-6 a-7 a-8 a-9 a-10 a-11 a-12

-continued

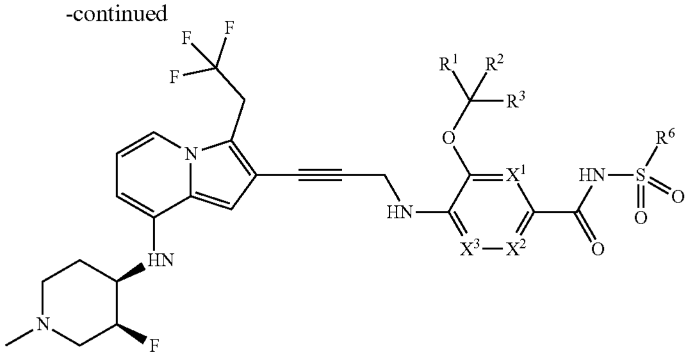

I-a

Step 1: Carrying out a cycloaromatization reaction between compound a-1 and ethyl bromopyruvate to obtain compound a-2; Wherein X is selected from Cl, Br, and I;

Step 2: Carrying out Vilsmeier-Haack reaction on compound a-2 to obtain compound a-3;

Step 3: Reacting compound a-3 with a fluorinating reagent to obtain compound a-4; Wherein the fluorinating reagent can be methyl fluorosulfonyldifluoroacetate, (triphenylphosphonio)difluoroacetate, or tetrabutylammonium fluoride;

Step 4: Carrying out a reduction reaction of the ester group on compound a-4 in the presence of a reducing agent to obtain compound a-5; Wherein the reducing agent can be sodium borohydride, lithium borohydride, lithium aluminum hydride, or diisobutylaluminium hydride;

Step 5: Oxidizing compound a-5 in the presence of an oxidizing agent to obtain compound a-6; Wherein the oxidizing agent can be Dess-Martin periodinane, Swern oxidation reagent, pyridinium chlorochromate, manganese dioxide, or sulfur trioxide/pyridine;

Step 6: Reacting compound a-6 with Gilbert reagent to generate compound a-7;

Step 7: Reacting compound a-7 with formaldehyde under the catalysis of a metal reagent to obtain compound a-8; Wherein the metal reagent can be a reagent containing Cu, such as tetrakis(acetonitrile)copper(I) hexafluorophosphate;

Step 8: Oxidizing compound a-8 into aldehyde a-9 in the presence of an oxidizing agent; Wherein the oxidizing agent can be Dess-Martin periodinane, Swern oxidation reagent, pyridinium chlorochromate, manganese dioxide, or sulfur trioxide/pyridine;

Step 9: Carrying out a reductive amination reaction between compound a-9 and compound a-10 to generate compound a-11; Wherein $R^1$, $R^2$, $R^3$, $R^6$, $X^1$, $X^2$, and $X^3$ are defined as above;

Step 10: Carrying out a metal reagent-catalyzed coupling reaction between compound a-11 and amine a-12 to obtain compound (I-a); Wherein the metal reagent can be a reagent containing Pd or Cu, such as Brettphos Pd G3, Brettphos Pd G4, or cuprous iodide.

Method 2:

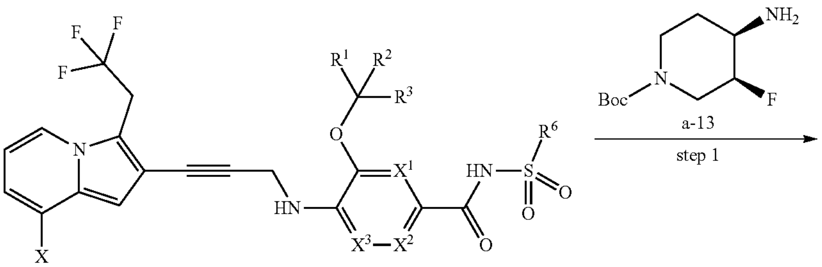

a-11

-continued
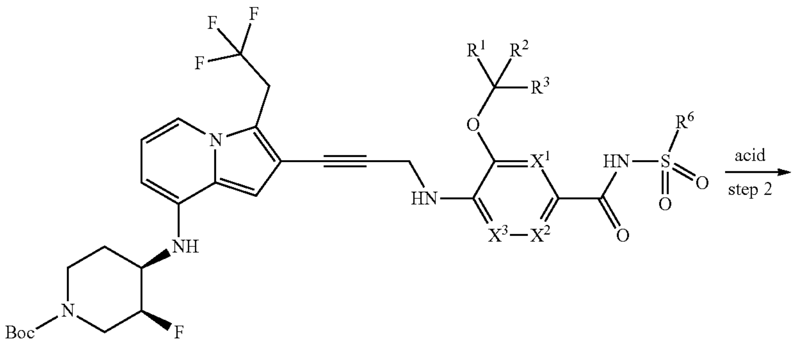
a-14
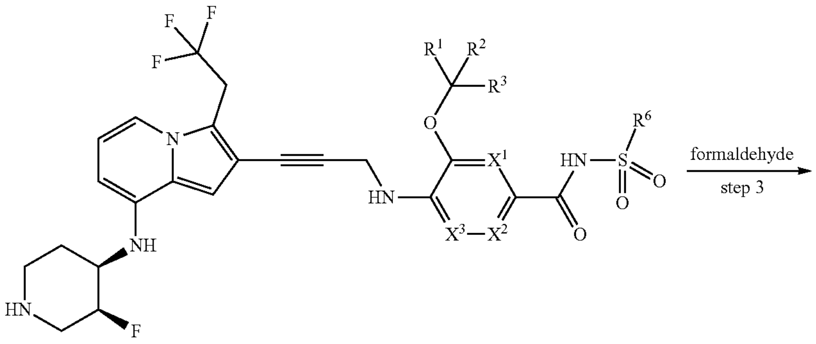
a-15
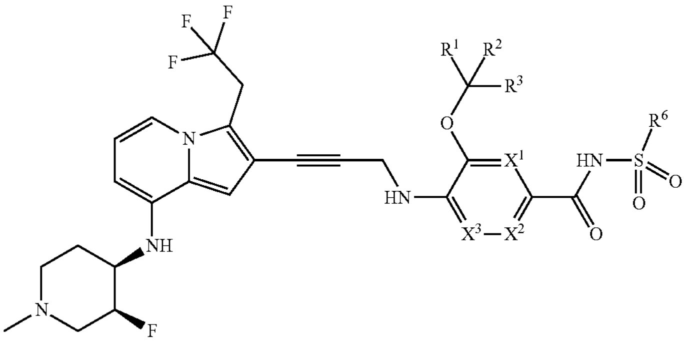
I-a

Step 1: Carrying out a metal reagent-catalyzed cross coupling reaction between compound a-11 and amine a-13 to obtain compound a-14; Wherein X is selected from Cl, Br, and I; $R^1$, $R^2$, $R^3$, $R^6$, $X^1$, $X^2$, and $X^3$ are defined as above; The metal reagent can be a reagent containing Pd or Cu, such as Brettphos Pd G3, Brettphos Pd G4, or cuprous iodide;

Step 2: Removing Boc protecting group form compound a-14 under acidic conditions to obtain compound a-15; Wherein the acidic conditions can be achieved in the presence of inorganic acids (e.g., HCl, HBr, or $H_2SO_4$), organic acids (e.g., trifluoroacetic acid), Lewis acids (e.g., zinc bromide), or other reagents (e.g., iodotrimethylsilane);

Step 3: Carrying out a reductive amination reaction between compound a-15 and formaldehyde to generate compound (I-a).

Method 3:

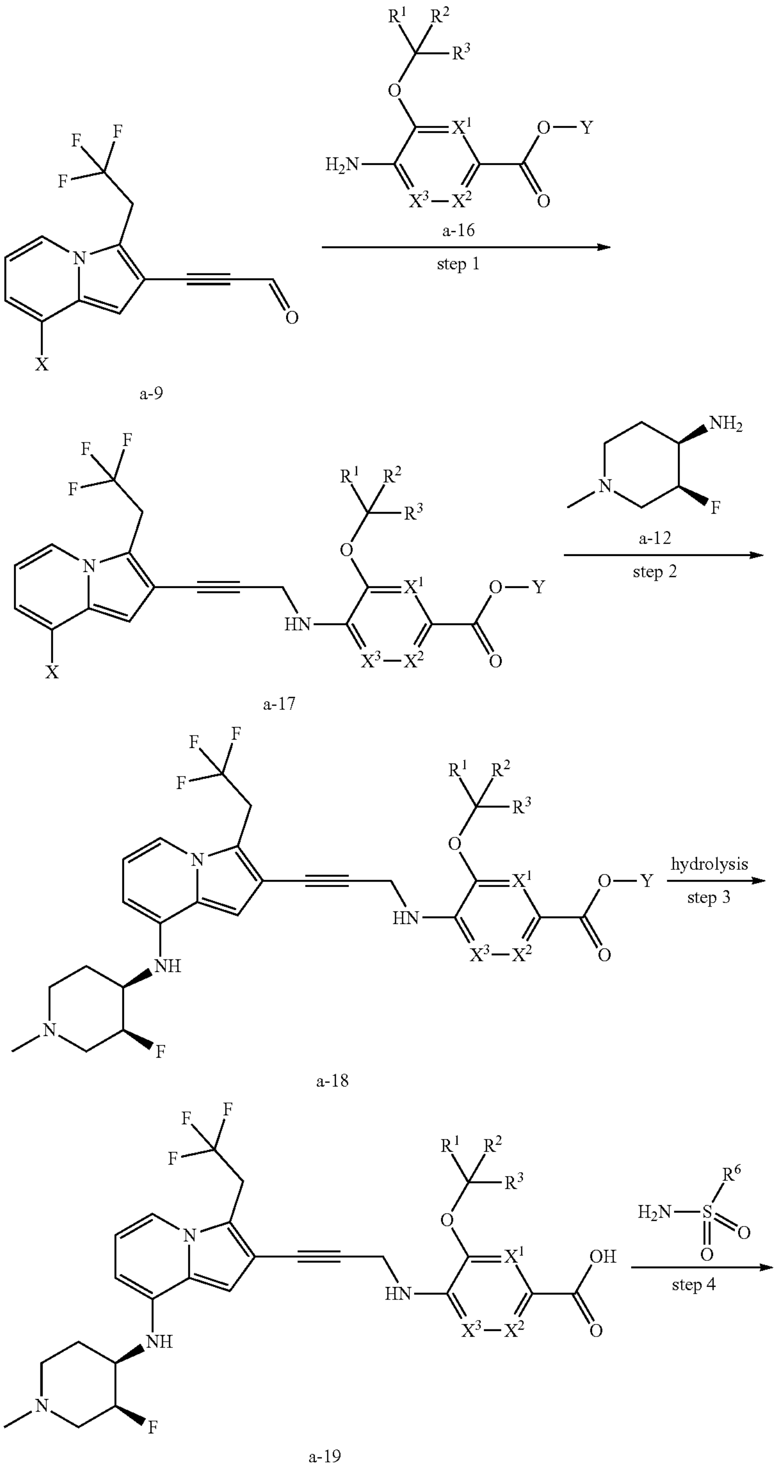

-continued

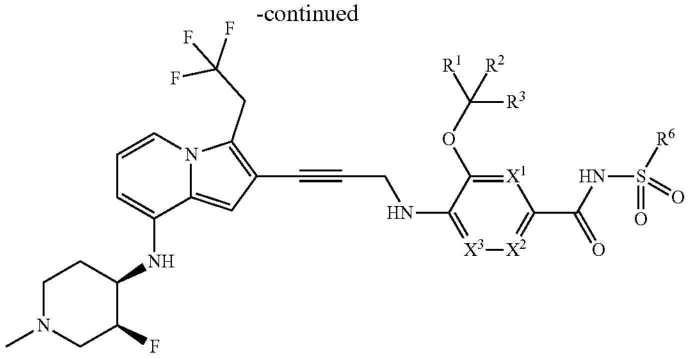

I-a

Step 1: Carrying out a reductive amination reaction between compound a-9 and compound a-16 to generate compound a-17; Wherein X is selected from Cl, Br, and I; Y is selected from $C_1$-$C_4$ alkyl; $R^1$, $R^2$, $R^3$, $X^1$, $X^2$, and $X^3$ are defined as above;

Step 2: Carrying out a metal reagent-catalyzed cross coupling reaction between compound a-17 and amine a-12 to obtain compound a-18; Wherein the metal reagent can be a reagent containing Pd or Cu, such as Brettphos Pd G3, Brettphos Pd G4, or cuprous iodide;

Step 3: Carrying out a hydrolysis reaction on compound a-18 to generate a-19 under acidic or basic conditions; Wherein the acidic conditions can be achieved in the presence of inorganic acids (e.g., HCl, HBr, or $H_2SO_4$) or organic acids (e.g., trifluoroacetic acid); The basic conditions can be achieved in the presence of inorganic bases (e.g., LiOH, NaOH, or KOH);

Step 4: Carrying out a condensation reaction between compound a-19 and sulfonamide $H_2NS(O)_2R^6$ to generate compound (I-a); Wherein $R^6$ is defined as above.

Method 4:

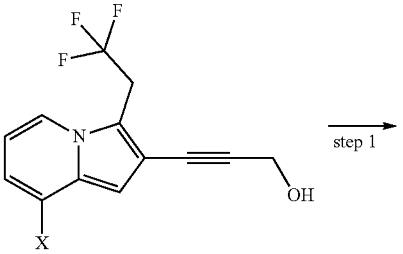

a-8

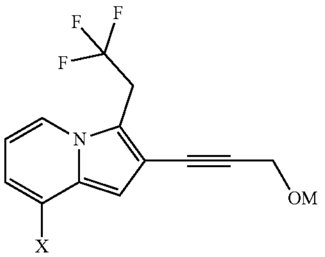

a-20

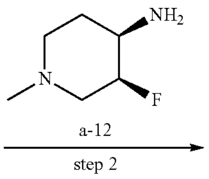

-continued

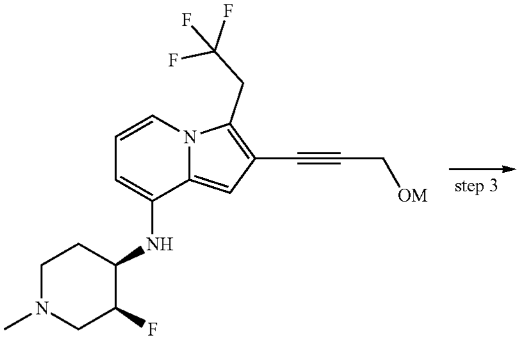

a-21

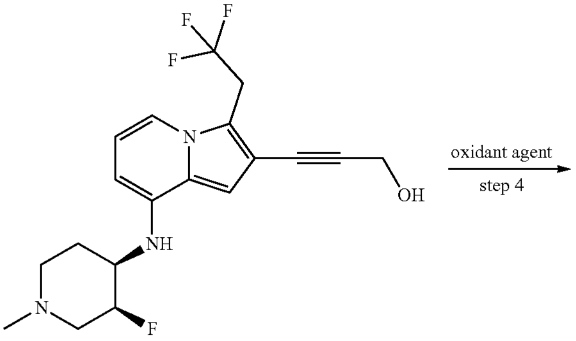

a-22

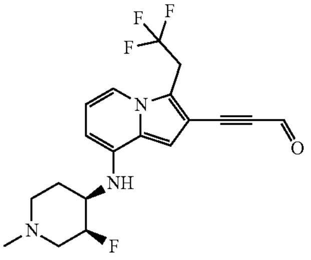

a-23

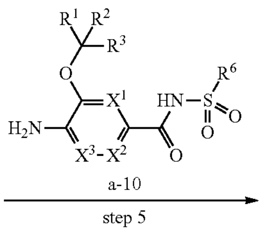

-continued

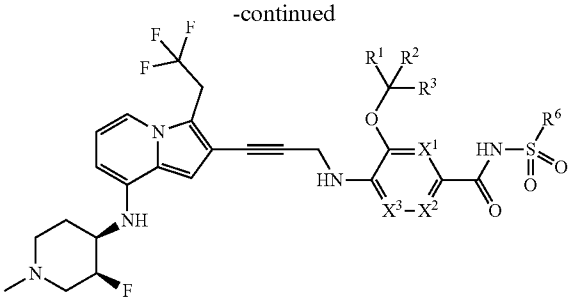

I-a

Step 1: Carrying out a hydroxyl protection reaction between compound a-8 and a suitable protecting agent to generate compound a-20; Wherein X is selected from Cl, Br, and I; M is a protecting group, such as trimethylsilyl, tert-butyldimethylsilyl, methoxymethyl, tert-butoxycarbonyl, or 2-tetrahydropyranyl; The protecting agent can be trimethylchlorosilane, tert-butyldimethylchlorosilane, chloromethyl methyl ether, di-tert-butyl dicarbonate, or 3,4-dihydro-2H-pyran;

Step 2: Carrying out a metal reagent-catalyzed cross coupling reaction between compound a-20 and amine a-12 to obtain compound a-21; Wherein the metal reagent can be a reagent containing Pd or Cu, such as Brettphos Pd G3, Brettphos Pd G4, or cuprous iodide;

Step 3: Removing the protecting group from compound a-21 to generate a-22 under acidic or basic conditions; Wherein the acidic conditions can be achieved in the presence of inorganic acids (e.g., HF, HCl, HBr, or $H_2SO_4$) or organic acids (e.g., trifluoroacetic acid); The basic conditions can be achieved in the presence of inorganic bases (e.g., LiOH, NaOH, or KOH) or organic bases (e.g., tetrabutylammonium fluoride);

Step 4: Carrying out an oxidation reaction on compound a-22 in the presence of an oxidizing agent to obtain compound a-23; Wherein the oxidizing agent can be Dess-Martin periodinane, Swern oxidation reagent, pyridinium chlorochromate, manganese dioxide, or sulfur trioxide/pyridine;

Step 5: Carrying out a reductive amination reaction between compound a-23 and sulfonamide a-10 to generate compound (I-a); Wherein $R^1$, $R^2$, $R^3$, $R^6$, $X^1$, $X^2$, and $X^3$ are defined as above;

Method 5:

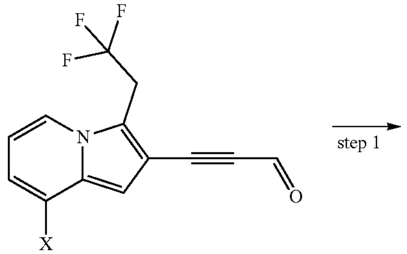

a-9

-continued

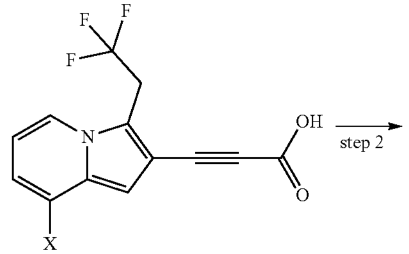

a-24

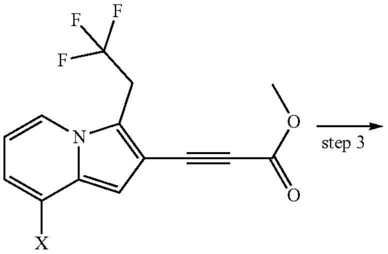

a-25

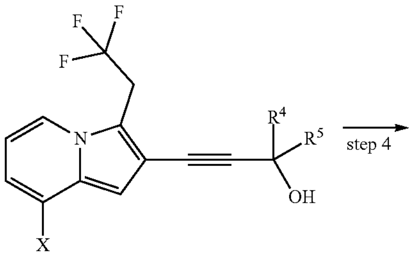

a-26

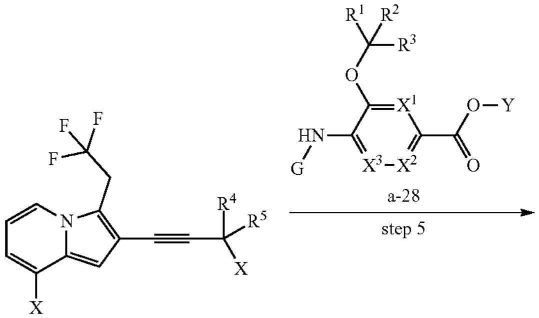

a-28 a-27

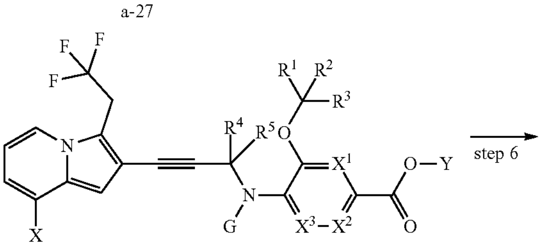

a-29

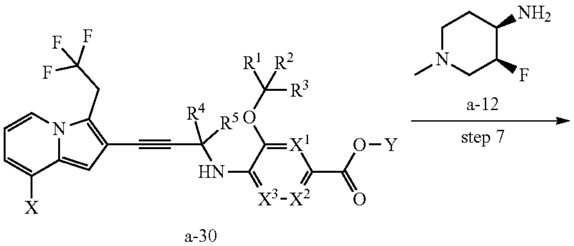

a-12 a-30

-continued

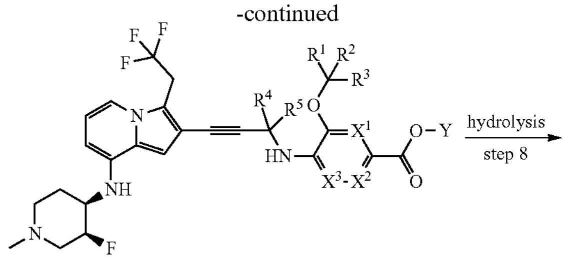

a-31

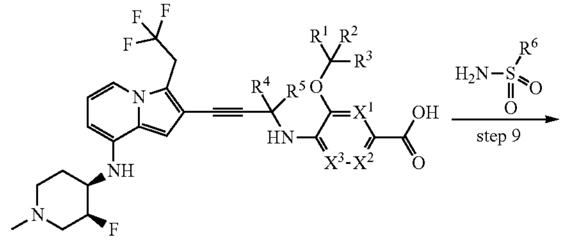

a-32

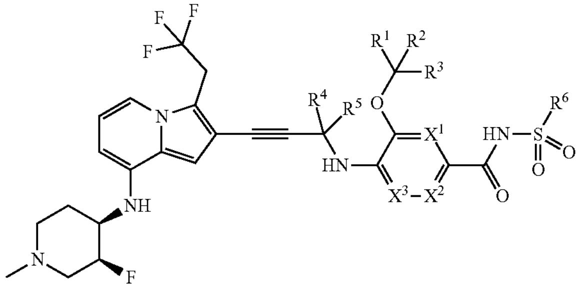

I

Step 1: Carrying out Pinnick oxidation reaction on compound a-9 to obtain compound a-24; Wherein X is selected from Cl, Br, and I;

Step 2: Carrying out an esterification reaction on compound a-24 to obtain compound a-25;

Step 3: Carrying out a reduction reaction on compound a-25 to obtain compound a-26; Wherein the reducing agent can be a reagent containing sodium (lithium) borohydride or lithium aluminum hydride, etc., as well as their deuterated reagents; $R^4$ and $R^5$ are defined as above;

Step 4: Carrying out a halogenation reaction on compound a-26 to obtain compound a-27; Wherein X is selected from Cl, Br, and I;

Step 5: Carrying out a nucleophilic substitution reaction between compounds a-27 and a-28 to obtain compound a-29; Wherein $R^1$, $R^2$, $R^3$, $X^1$, $X^2$, and $X^3$ are defined as above; G is a protecting group, such as p-toluenesulfonyl or tert-butoxycarbonyl; Y is selected from $C_1$-$C_4$ alkyl;

Step 6: Removing the protecting group G from compound a-29 to obtain a-30;

Step 7: Carrying out a metal reagent-catalyzed cross coupling reaction between compound a-30 and amine a-12 to obtain compound a-31; Wherein the metal reagent can be a reagent containing Pd or Cu, such as Brettphos Pd G3, Brettphos Pd G4, or cuprous iodide;

Step 8: Carrying out a hydrolysis reaction on compound a-31 to generate a-32 under acidic or basic conditions; Wherein the acidic conditions can be achieved in the presence of inorganic acids (e.g., HCl, HBr, or $H_2SO_4$) or organic acids (e.g., trifluoroacetic acid); The basic conditions can be achieved in the presence of inorganic bases (e.g., LiOH, NaOH, or KOH);

Step 9: Carrying out a condensation reaction between compound a-32 and sulfonamide $H_2NS(O)_2R^6$ to generate compound (I); Wherein $R^6$ is defined as above.

The present disclosure further provides a pharmaceutical composition comprising the compound of formula I, the isotope-labeled compound thereof, the solvate thereof, the pharmaceutically acceptable salt thereof, or the solvate of the pharmaceutically acceptable salt thereof (e.g., in an effective therapeutic amount), and a pharmaceutical excipient.

The present disclosure further provides a use of the compound of formula I, the isotope-labeled compound thereof, the solvate thereof, the pharmaceutically acceptable salt thereof, or the solvate of the pharmaceutically acceptable salt thereof, or the pharmaceutical composition in the manufacture of a p53 mutant pocket binding agent or a medicament for the treatment or prevention of a disease related to p53 mutants.

In a preferred technical solution, the described use meets one or more of the following conditions:

(1) The p53 mutant has a mutation at amino acid 220, such as p53 Y220C;

(2) The pocket binding agent promotes the binding of p53 mutants with DNA;

(3) The disease related to p53 mutants is cancer, such as breast cancer, gastric cancer, lung cancer, or ovarian cancer.

The present disclosure further provides a use of the compound of formula I, the isotope-labeled compound thereof, the solvate thereof, the pharmaceutically acceptable salt thereof, or the solvate of the pharmaceutically acceptable salt thereof, or the pharmaceutical composition in the manufacture of a medicament for the treatment or prevention of cancer.

The cancer is, for example, breast cancer, gastric cancer, lung cancer, or ovarian cancer.

The present disclosure further provides a method for the treatment or prevention of cancer, characterized in that the method comprises: Administering to a patient a therapeutically effective amount of the compound of formula I, the isotope-labeled compound thereof, the solvate thereof, the pharmaceutically acceptable salt thereof, or the solvate of the pharmaceutically acceptable salt thereof.

The cancer is defined as above.

The present disclosure further provides a compound of formula a-11 or a-32 (which can be used to prepare the above compound of formula I);

a-11

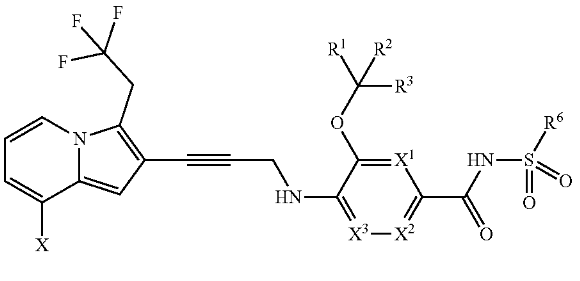

-continued a-33

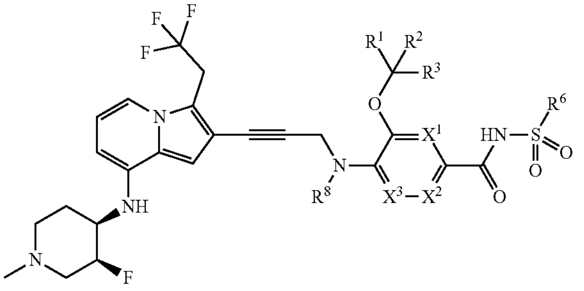

Wherein X is halogen (e.g., Br); $R^8$ is an amino protecting group (e.g., -Boc);

$X^1$, $X^2$, $X^3$, $R^1$, $R^2$, $R^3$, $R^4$, $R^5$, and $R^6$ are defined as above.

The compound of formula a-11 or a-32 is preferably any one of the following compounds;

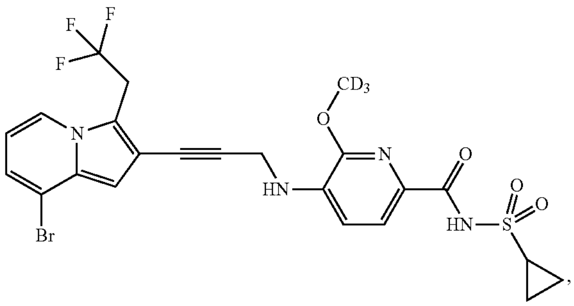

,

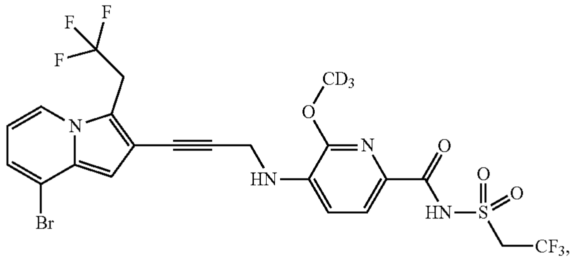

,

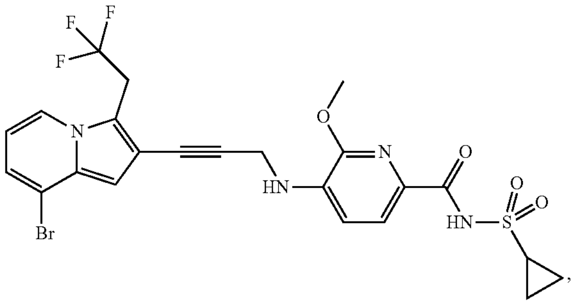

,

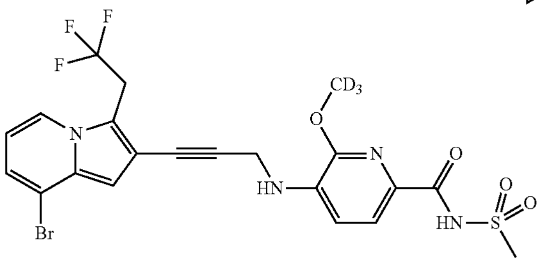

or

-continued

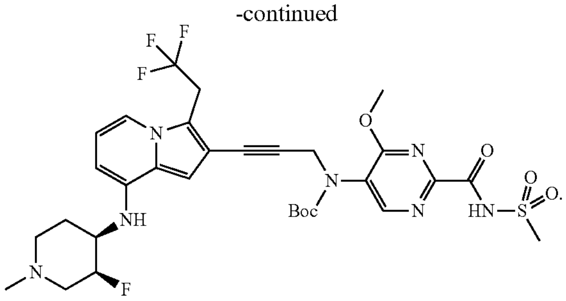

The term "pharmaceutically acceptable" refers to relatively nontoxic, safe, and suitable for patient use.

The term "pharmaceutically acceptable salt" refers to a salt obtained by reacting a compound with a pharmaceutically acceptable acid or base. When a compound contains relatively acidic functional groups, the corresponding base addition salt can be obtained by contacting a compound with a sufficient amount of pharmaceutically acceptable base in an appropriate inert solvent. When a compound contains relatively basic functional groups, the corresponding acid addition salt can be obtained by contacting a compound with a sufficient amount of pharmaceutically acceptable acid in an appropriate inert solvent. For details, see "Handbook of Pharmaceutical Salts: Properties, Selection, and Use" (P. Heinrich Stahl, Camille G. Wermuth, 2011, 2nd Revised Edition).

The term "solvate" refers to a substance formed by combining a compound with a solvent (including but not limited to: water, methanol, ethanol, etc.). Solvates are classified into stoichiometric solvates and non-stoichiometric solvates.

The term "solvate of the pharmaceutically acceptable salt" refers to a substance formed by combining a compound with a pharmaceutically acceptable acid or base and a solvent (including but not limited to: water, methanol, ethanol, etc.). The amount of solvent herein can be stoichiometric or non-stoichiometric.

The "-" at the end of a group indicates that the group is connected to the rest of the molecule through this site. For example, $CH_3$—C(═O)— refers to an acetyl group.

When the valence bond of a group is marked with a wavy line "〰", such as in

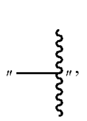

the wavy line indicates the point at which the group is connected to the rest of the molecule.

The term "halogen" refers to fluorine, chlorine, bromine, or iodine.

The term "alkyl" refers to a straight or branched, monovalent hydrocarbyl group with a specified number of carbon atoms (e.g., $C_1$-$C_6$). Alkyl groups include, but are not limited to: methyl, ethyl, n-propyl, isopropyl, n-butyl, isobutyl, sec-butyl, tert-butyl, n-pentyl, n-hexyl, etc.

The term "alkoxy" refers to the group $R^X$—O—, where $R^X$ is defined as in the term "alkyl". Alkoxy groups include, but are not limited to: methoxy, ethoxy, n-propoxy, isopropoxy, etc.

The term "therapeutically effective amount" refers to an amount administered to a patient that is sufficient to effectively treat a disease. The therapeutically effective amount will vary depending on the type of compound, type of disease, severity of the disease, patient's age, etc., but can be adjusted by those skilled in the art as required.

The term "pharmaceutical excipient" refers to all substances contained in pharmaceutical preparations, except active pharmaceutical ingredients, and is generally divided into two categories: vehicles and additives. For details, see "Pharmacopoeia of the People's Republic of China (2020 Edition)" and "Handbook of Pharmaceutical Excipients" (Paul J Sheskey, Bruno C Hancock, Gary P Moss, David J Goldfarb, 2020, 9th Edition).

The term "treat/treatment" refers to eliminating the cause of the disease or alleviating the symptoms.

The term "prevent/prevention" refers to reducing the risk of developing a disease.

The term "patient" refers to any animal, usually a mammal, such as a human, in need of treatment or prevention of disease. Mammals include, but are not limited to: cattle, horses, sheep, pigs, cats, dogs, mice, rats, rabbits, guinea pigs, monkeys, humans, etc.

The term "PG" refers to a protecting group, such as Boc protecting group.

In accordance with common knowledge in the art, the above various preferred conditions can be arbitrarily combined to obtain the various preferred embodiments of the present disclosure.

The reagents and raw materials used in the present disclosure are commercially available.

The positive and progressive effect of the present disclosure is that the compounds of the present disclosure can promote the binding of p53 Y220C with DNA and possess better inhibitory activity against the proliferation of cancer cells represented by gastric cancer cells.

DETAILED DESCRIPTION OF THE INVENTION

Figure 1:
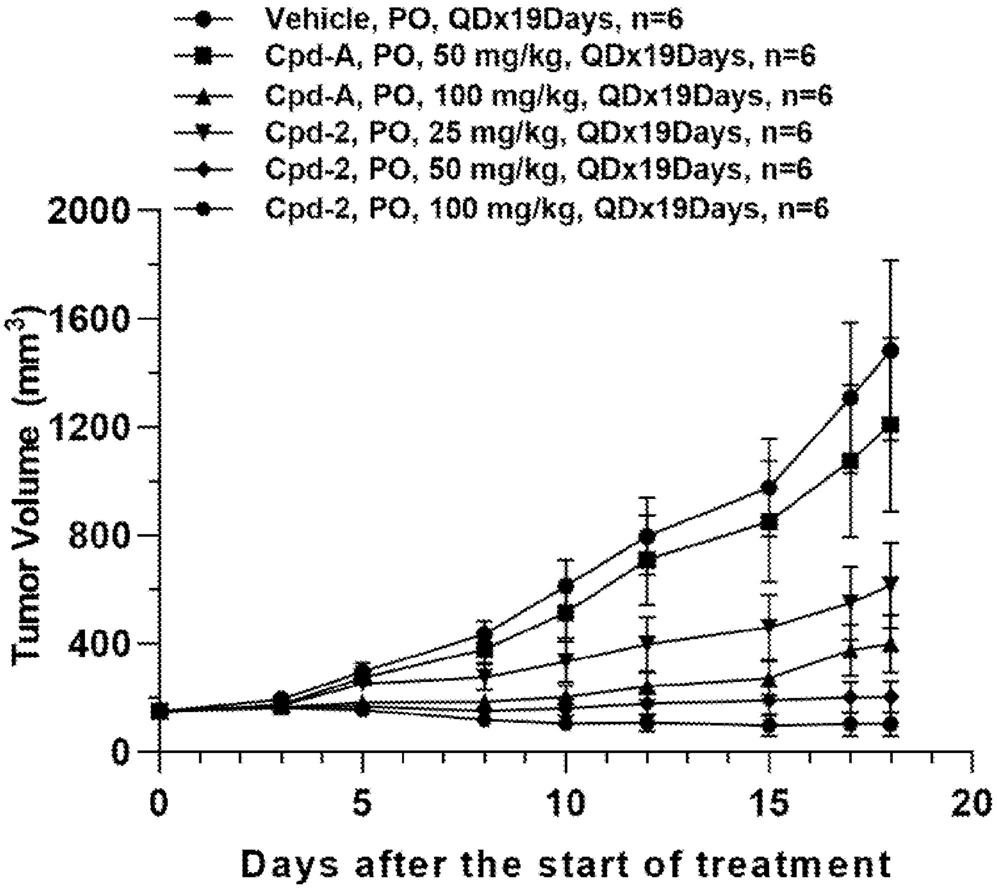
FIG. 1 shows the tumor growth curves of the control group and each treatment group in the efficacy study of NUGC-3 human gastric cancer xenograft mice model described in test example IX.

The present disclosure is further described through examples below, but is not limited to the scope of the examples provided. Unless otherwise stated, the actual operations disclosed in the present disclosure will adopt conventional techniques of organic synthesis, cell biology, cell culture, and molecular biology within the technical scope of the art.

In each example, $^1$HNMR was recorded by a BRUKER AVANCE NEO 400 MHZ, JNM-ECZ400s nuclear magnetic resonance instrument, and the chemical shift was expressed in δ (ppm); Liquid chromatography-mass spectrometry (LCMS) was recorded by a Shimadzu LC-20AD, Agilent 1260, and Agilent 1200 mass spectrometer; Preparative HPLC separation was performed using a WATERS Autop, Shimadzu LC20AR liquid chromatograph.

| | |
|---|---|
| BrettPhos Pd G3 | Methanesulfonato(2-Dicyclohexylphosphino-3,6-dimethoxy-2',4',6'-tri-i-propyl-1,1'-bipheny)(2'-amino-1,1'-biphenyl-2-yl)palladium(II) |
| BrettPhos Pd G4 | Methanesulfonato(2-Dicyclohexylphosphino-3,6-dimethoxy-2',4',6'-tri-i-propyl-1,1'-biphenyl)(2'-methylamino-1,1'-biphenyl-2-yl)palladium(II) |
| CDI | N,N'-Carbonyldiimidazole |
| DBU | 1,8-Diazabicyclo[5,4,0]undec-7-ene |
| DCM | Dichloromethane |
| DIBAL-H | Diisobutylaluminium hydride |
| DMF | N,N-Dimethylformamide |
| DMP | Dess-Martin periodinane |
| DMSO | Dimethyl sulfoxide |
| EtOAc | Ethyl acetate |
| EDCI | 1-Ethyl-(3-dimethylaminopropyl)carbonyldiimide hydrochloride |
| HATU | 2-(7-Azabenzotriazol-1-yl)-N,N,N',N'-tetramethyluronium hexafluorophosphate |
| MTBE | tert-Butyl methyl ether |
| MeOH | Methanol |
| $NaBH_3CN$ | Sodium cyanoborohydride |
| $Na_2SO_4$ | Sodium sulfate |
| NMP | N-Methyl pyrrolidone |
| $Pd(dppf)Cl_2$ | [1,1'-Bis(diphenylphosphino) ferrocene]dichloropalladium(II) |
| PE | Petroleum ether |
| Ruphos | 2-Dicyclohexylphosphino-2',6'-di-iso-propoxy-1,1'-biphenyl |
| SGC | Silica gel column chromatography |
| TBAF | Tetrabutylammonium fluoride |
| TEA | Triethylamine |
| THF | Tetrahydrofuran |

Preparation of Intermediates Int-1 and Int-1-7

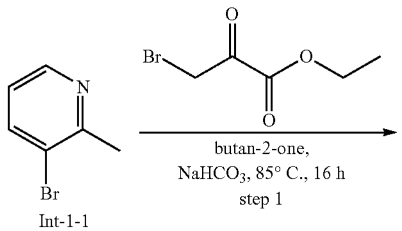

Int-1-1

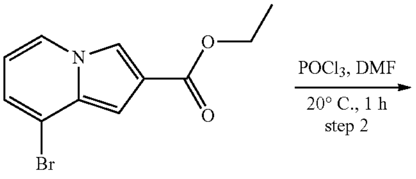

Int-1-2

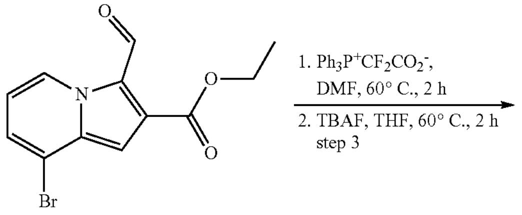

Int-1-3

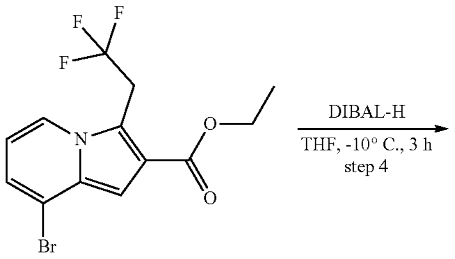

Int-1-4

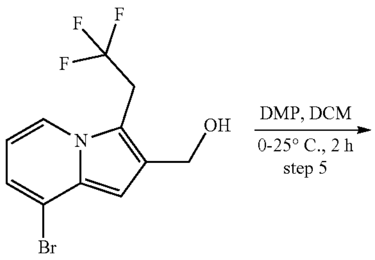

Int-1-5

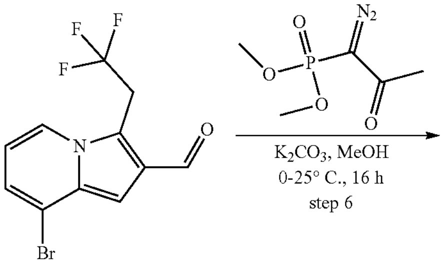

Int-1-6

-continued

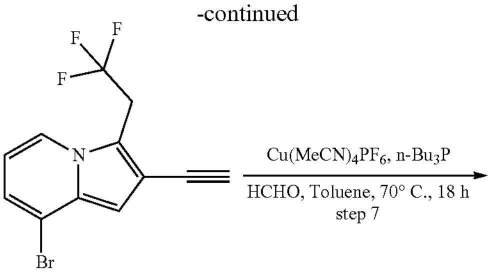

Int-1

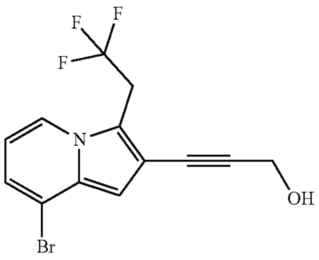

Int-1-7

Step 1: Ethyl 8-bromoindolizine-2-carboxylate

A mixture of 3-bromo-2-methylpyridine Int-1-1 (500 mg, 2.91 mmol), ethyl 3-bromopyruvate (850 mg, 4.36 mmol), and sodium bicarbonate (561 mg, 6.69 mmol) in butanone (5 mL) was stirred at 85° C. for 16 hours, then concentrated to dryness, and purified by SGC (0 to 10% EtOAc added to PE) method to obtain ethyl 8-bromoindolizine-2-carboxylate Int-1-2 (190 mg, 24.4% yield) as a gray solid. LCMS calculated for $C_{11}H_{11}BrNO_2$ $[M+H]^+$: m/z=268.0/270.0; found: 267.9/269.9; $^1H$ NMR (400 MHZ, $CDCl_3$) δ 7.88 (d, J=1.6 Hz, 1H), 7.87-7.83 (m, 1H), 7.03-6.99 (m, 1H), 6.95 (d, J=6.8 Hz, 1H), 6.43 (t, J=7.2 Hz, 1H), 4.37 (q, J=7.2 Hz, 2H), 1.40 (t, J=6.8 Hz, 3H).

Step 2: Ethyl 8-bromo-3-formylindolizine-2-carboxylate

A solution of ethyl 8-bromoindolizine-2-carboxylate Int-1-2 (5.34 g, 19.9 mmol) in DCM (130 mL) was added dropwise to a solution of phosphorus oxychloride (5.19 g, 33.8 mmol) in DMF (130 mL) at 0° C. The mixture was stirred at 20° C. for 1 hour, then was slowly quenched with saturated sodium bicarbonate aqueous solution (300 mL) and extracted with DCM (200 mL). The separated organic layers were combined, dried over $Na_2SO_4$, filtered, and concentrated to dryness. The residue was purified by SGC (0 to 10% EtOAc added to PE) to obtain ethyl 8-bromo-3-formylindolizine-2-carboxylate Int-1-3 (10.6 g, crude product) as a yellow colloid. LCMS calculated for $C_{12}H_{11}BrNO_3$ $[M+H]^+$: m/z=296.0/298.0; found: 295.9/297.9.

Step 3: Ethyl 8-bromo-3-(2,2,2-trifluoroethyl)indolizine-2-carboxylate

A mixture of ethyl 8-bromo-3-formylindolizine-2-carboxylate Int-1-3 (8.50 g, 15.8 mmol) and 2,2-difluoro-2-triphenylphosphaniumylacetate (11.2 g, 31.5 mmol) in DMF (120 mL) was stirred for 2 hours at 60° C. TBAF (47.3 mL, 47.3 mmol, 1M in THF) was added to the mixture. The reaction mixture was stirred at 60° C. for 2 hours, then diluted with water (100 mL) and extracted with MTBE (100 mL×3). The organic layers were combined, dried over $Na_2SO_4$, filtered, and concentrated to dryness under reduced pressure. The residue was purified by SGC (0 to 5% EtOAc added to PE) method to obtain ethyl 8-bromo-3-(2,2,2-trifluoroethyl)indolizine-2-carboxylate Int-1-4 (2.40 g, 43.4% yield) as a white solid. LCMS calculated for $C_{13}H_{12}BrF_3NO_2$ $[M+H]^+$: m/z=350.0/352.0; found: 349.9/351.9; $^1H$ NMR (400 MHZ, $CDCl_3$) δ 7.89 (d, J=7.2 Hz, 1H), 7.12 (s, 1H), 7.05 (d, J=6.8 Hz, 1H), 6.56 (t, J=7.2 Hz, 1H), 4.40 (q, J=7.2 Hz, 2H), 4.25 (q, J=10.0 Hz, 2H), 1.42 (t, J=7.2 Hz, 3H).

Step 4: (8-Bromo-3-(2,2,2-trifluoroethyl)indolizin-2-yl)methanol

DIBAL-H (35.1 mL, 35.1 mmol, 1M in toluene) was added to a mixture of ethyl 8-bromo-3-(2,2,2-trifluoroethyl) indolizine-2-carboxylate Int-1-4 (4.10 g, 11.7 mmol) in THF (120 mL). The reaction mixture was stirred at −10° C. for 3 hours to obtain a yellow solution. The reaction mixture was poured into saturated ammonium chloride aqueous solution (200 mL), then water (200 mL) was added thereto, and the mixture was extracted with EtOAc (150 mL×3). The organic layers were combined, dried over $Na_2SO_4$, filtered, and concentrated to dryness under reduced pressure. The residue was purified by SGC (0 to 5% EtOAc added to PE) method to obtain (8-bromo-3-(2,2,2-trifluoroethyl)indolizin-2-yl) methanol Int-1-5 (3.55 g, 98.4% yield) as a white solid. LCMS calculated for $C_{11}H_{10}BrF_3NO$ $[M+H]^+$: m/z=308.0/310.0; found: 307.9/309.9; $^1H$ NMR (400 MHZ, $CDCl_3$) δ 7.85 (d, J=7.2 Hz, 1H), 7.00 (d, J=6.8 Hz, 1H), 6.70 (br s, 1H), 6.50 (t, J=7.2 Hz, 1H), 4.84 (s, 2H), 3.83 (q, J=10.4 Hz, 2H).

Step 5: 8-Bromo-3-(2,2,2-trifluoroethyl)indolizine-2-carbaldehyde

DMP (7.33 g, 17.2 mmol) was added to a solution of (8-bromo-3-(2,2,2-trifluoroethyl)indolizin-2-yl)methanol Int-1-5 (3.55 g, 11.5 mmol) in DCM (400 mL) at 0° C. The reaction system was warmed to room temperature and stirred for 2 hours. The reaction mixture was poured into saturated sodium bicarbonate aqueous solution (20 mL), then was added with water (200 mL) and extracted with DCM (100 mL×3). The organic layers were combined, dried over $Na_2SO_4$, filtered, and concentrated to dryness under reduced pressure. The residue was purified by SGC (0 to 7% EtOAc added to PE) method to obtain 8-bromo-3-(2,2,2-trifluoroethyl)indolizine-2-carbaldehyde Int-1-6 (2.70 g, 76.5% yield) as a white solid. LCMS calculated for $C_{11}H_8BrF_3NO$ $[M+H]^+$: m/z=306.0/308.0; found: 305.9/307.9.

Step 6: 8-Bromo-2-ethynyl-3-(2,2,2-trifluoroethyl) indolizine

At 0° C., 8-bromo-3-(2,2,2-trifluoroethyl)indolizine-2-carbaldehyde Int-1-6 (500 mg, 1.63 mmol) was added to a mixture of dimethyl (1-diazo-2-oxopropyl)phosphonate (470 mg, 2.45 mmol) and potassium carbonate (451 mg, 3.27 mmol) in methanol (15 mL). The reaction system was warmed to room temperature and stirred for 16 hours. The reaction mixture was diluted with water (50 mL) and extracted with EtOAc (50 mL×3). The organic layers were combined, dried over $Na_2SO_4$, filtered, and concentrated to dryness under reduced pressure. The residue was purified by SGC (0 to 3% EtOAc added to PE) method to obtain 8-bromo-2-ethynyl-3-(2,2,2-trifluoroethyl)indolizine Int-1 (380 mg, 77.0% yield) as a white solid. LCMS calculated for $C_{12}H_8BrF_3N$ $[M+H]^+$: m/z=302.0/304.0; found: 301.9/303.9; $^1H$ NMR (400 MHZ, $CDCl_3$) δ 7.81 (d, J=7.2 Hz, 1H), 7.03 (d, J=7.2 Hz, 1H), 6.79 (s, 1H), 6.52 (t, J=7.2 Hz, 1H), 3.83 (q, J=10.0 Hz, 2H), 3.25 (s, 1H).

Step 7: 3-(8-Bromo-3-(2,2,2-trifluoroethyl)indolizin-2-yl)prop-2-yn-1-ol

Under nitrogen atmosphere, tetrakis(acetonitrile)copper (I) hexafluorophosphate (123 mg, 0.33 mmol) and tributylphosphine (268 mg, 1.32 mmol) were dissolved in toluene (15 mL), and the reaction mixture was stirred at 70° C. for 30 minutes. Then 8-bromo-2-ethynyl-3-(2,2,2-trifluoroethyl)indolizine Int-1 (1.00 g, 3.31 mmol) and formaldehyde aqueous solution (0.18 mL, 6.62 mmol, 36% to 38% content) were added thereto. The mixture was stirred at 70° C. overnight. After the completion of the reaction detected by TLC, the mixture was concentrated under vacuum. The residue was purified by SGC (0 to 15% EtOAc added to PE) method to obtain 3-(8-bromo-3-(2,2,2-trifluoroethyl)indolizin-2-yl)prop-2-yn-1-ol Int-1-7 (843 mg, 76.7% yield) as a white solid. LCMS calculated for $C_{13}H_{10}BrF_3NO$ $[M+H]^+$: m/z=332.0/334.0; found: 332.3/334.3; $^1H$ NMR (400 MHZ, DMSO-$d_6$) δ 8.38 (d, J=7.1 Hz, 1H), 7.19 (d, J=7.1 Hz, 1H), 6.68 (t, J=7.1 Hz, 1H), 6.61 (s, 1H), 5.34 (t, J=6.0 Hz, 1H), 4.34 (d, J=6.0 Hz, 2H), 4.20-4.11 (m, 2H).

Cpd-C: 4-((3-(8-(((3S,4R)-3-Fluoro-1-methylpiperidin-4-yl)amino)-3-(2,2,2-trifluoroethyl)indolizin-2-yl)prop-2-yn-1-yl)amino)-3-methoxy-N-methylbenzamide

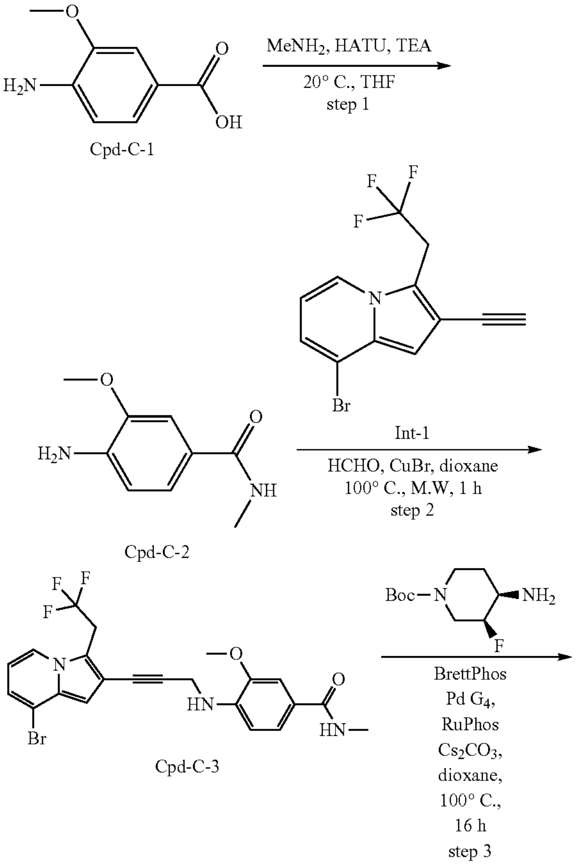

-continued

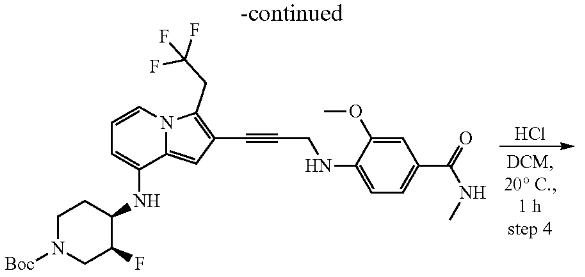

Cpd-C-4

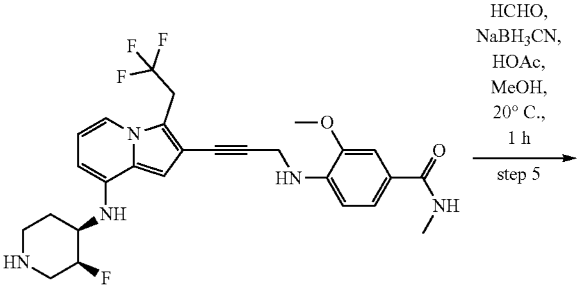

Cpd-C-5

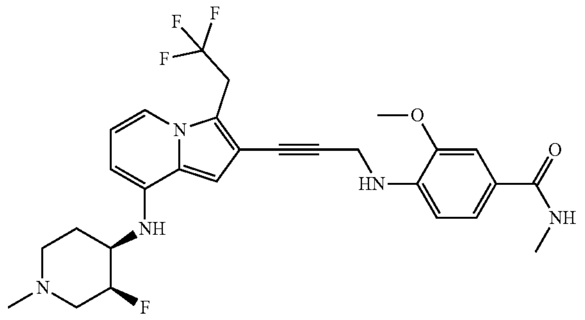

Cpd-C

Step 1: 4-Amino-3-methoxy-N-methylbenzamide

HATU (18.8 g, 49.5 mmol) was added to a solution of 4-amino-3-methoxybenzoic acid Cpd-C-1 (7.52 g, 45.0 mmol), methylamine solution (6.71 g, 54.0 mmol, 25% content), and triethylamine (18.8 mL, 135 mmol) in THF (45 mL) at 0° C. The reaction was stirred at 20° C. for 2 hours. The reaction mixture was concentrated under reduced pressure. The residue was purified by SGC (0 to 4% MeOH added to DCM) method to obtain 4-amino-3-methoxy-N-methylbenzamide Cpd-C-2 (6.08 g, 75.0% yield) as a white solid. LCMS calculated for $C_9H_{13}N_2O_2$ $[M+H]^+$: m/z=181.1; found: 181.2.

Step 2: 4-((3-(8-Bromo-3-(2,2,2-trifluoroethyl)indolizin-2-yl)prop-2-yn-1-yl)amino)-3-methoxy-N-methylbenzamide Formaldehyde aqueous solution (497 mg, 5.96 mmol, 36% to 38% content) and cuprous bromide (567 mg, 3.97 mmol) were added to a mixture of 8-bromo-2-ethynyl-3-(2,2,2-trifluoroethyl)indolizine Int-1 (600 mg, 1.99 mmol) and 4-amino-3-methoxy-N-methylbenzamide Cpd-C-2 (716 mg, 3.97 mmol) in 1,4-dioxane (12 mL). The reaction was stirred under microwave irradiation at 100° C. for 1 hour. The residue was purified by SGC (0 to 30% EtOAc added to DCM) method to obtain 4-((3-(8-bromo-3-(2,2,2-trifluoroethyl)indolizin-2-yl)prop-2-yn-1-yl)amino)-3-methoxy-N-methylbenzamide Cpd-C-3 (480 mg, 48.9% yield) as a yellow solid. LCMS calculated for $C_{22}H_{20}BrF_3N_3O_2$ $[M+H]^+$: m/z=494.1/496.1; found: 494.2/496.2.

Step 3: tert-Butyl (3S,4R)-3-fluoro-4-((2-(3-((2-methoxy-4-(methylcarbamoyl)phenyl)amino)prop-1-yn-1-yl)-3-(2,2,2-trifluoroethyl)indolizin-8-yl)amino)piperidine-1-carboxylate Under argon atmosphere, a mixture of 4-((3-(8-bromo-3-(2,2,2-trifluoroethyl)indolizin-2-yl)prop-2-yn-1-yl)amino)-3-methoxy-N-methylbenzamide Cpd-C-3 (1.35 g, 2.73 mmol), tert-butyl (3S,4R)-4-amino-3-fluoropiperidine-1-carboxylate (1.19 g, 5.46 mmol), BrettPhos Pd G4 (0.50 g, 0.55 mmol), Ruphos (0.25 g, 0.55 mmol), and cesium carbonate (1.78 g, 5.46 mmol) in 1,4-dioxane (50 mL) was stirred at 100° C. for 16 hours. The reaction mixture was diluted with EtOAc (200 mL), washed with water (100 mL) and saturated brine (100 mL), dried over anhydrous $Na_2SO_4$, filtered, and concentrated under reduced pressure. The residue was purified by SGC (0 to 50% EtOAc added to DCM) to obtain tert-butyl (3S,4R)-3-fluoro-4-((2-(3-((2-methoxy-4-(methylcarbamoyl)phenyl)amino)prop-1-yn-1-yl)-3-(2,2,2-trifluoroethyl)indolizin-8-yl)amino)piperidine-1-carboxylate Cpd-C-4 (1.00 g, 58.0% yield) as a yellow solid. LCMS calculated for $C_{32}H_{38}F_4N_5O_4$ $[M+H]^+$: m/z=632.3; found: 632.5.

Step 4: 4-((3-(8-(((3S,4R)-3-Fluoropiperidin-4-yl)amino)-3-(2,2,2-trifluoroethyl)indolizin-2-yl)prop-2-yn-1-yl)amino)-3-methoxy-N-methylbenzamide HCl (7.92 mL, 31.7 mmol, 4N in 1,4-dioxane) was added to a solution of tert-butyl (3S,4R)-3-fluoro-4-((2-(3-((2-methoxy-4-(methylcarbamoyl)phenyl)amino)prop-1-yn-1-yl)-3-(2,2,2-trifluoroethyl)indolizin-8-yl)amino)piperidine-1-carboxylate Cpd-C-4 (1.00 g, 1.58 mmol) in DCM (16 mL) at 0° C. The mixture was warmed to room temperature and stirred for 1 hour. The mixture was concentrated to dryness, diluted with water (30 mL), and the pH was adjusted to 7 to 8 with saturated sodium bicarbonate solution. The aqueous phase was extracted with DCM (100 mL×2), and the combined organic phases were dried over anhydrous $Na_2SO_4$, filtered, and concentrated to obtain 4-((3-(8-(((3S,4R)-3-fluoropiperidin-4-yl)amino)-3-(2,2,2-trifluoroethyl)indolizin-2-yl)prop-2-yn-1-yl)amino)-3-methoxy-N-methylbenzamide Cpd-C-5 (450 mg, crude product) as a yellow solid. The crude product was used directly in the next step reaction. LCMS calculated for $C_{27}H_{30}F_4N_5O_2$ $[M+H]^+$: m/z=532.2; found: 532.4.

Step 5: 4-((3-(8-(((3S,4R)-3-Fluoro-1-methylpiperidin-4-yl)amino)-3-(2,2,2-trifluoroethyl)indolizin-2-yl)prop-2-yn-1-yl)amino)-3-methoxy-N-methylbenzamide Sodium cyanoborohydride (160 mg, 2.54 mmol) was added to a solution of 4-((3-(8-(((3S,4R)-3-fluoropiperidin-4-yl)amino)-3-(2,2,2-trifluoroethyl)indolizin-2-yl)prop-2-yn-1-yl)amino)-3-methoxy-N-methylbenzamide Cpd-C-5 (450 mg, 0.85 mmol), acetic acid (0.02 mL, 0.42 mmol), and formaldehyde aqueous solution (212 mg, 2.54 mmol, 36% to 38% content) in methanol (20 mL) at room temperature, and the reaction mixture was stirred for 1 hour at room temperature. The pH was adjusted to 7 to 8 by dropwise adding saturated sodium bicarbonate solution to the reaction mixture. The aqueous phase was extracted with EtOAc (100 mL×3). The organic phases were combined and washed with saturated brine (50 mL×3), dried over anhydrous $Na_2SO_4$, filtered, and concentrated. The residue was subjected to preparative purification to obtain 4-((3-(8-(((3S,4R)-3-fluoro-1-methylpiperidin-4-yl)amino)-3-(2,2,2-trifluoroethyl)indolizin-2-yl)prop-2-yn-1-yl)amino)-3-methoxy-N-methylbenzamide Cpd-C (119 mg, 25.2% yield) as a white solid. LCMS calculated for $C_{28}H_{32}F_4N_5O_2$ $[M+H]^+$: m/z=546.2; found: 546.2; $^1H$ NMR (400 MHZ, DMSO-$d_6$) δ 8.08 (d, J=4.6 Hz, 1H), 7.57 (d, J=6.9 Hz, 1H), 7.41 (dd, J=8.2, 1.7 Hz, 1H), 7.34 (d, J=1.7 Hz, 1H), 6.91 (s, 1H), 6.74 (d, J=8.3 Hz, 1H), 6.51 (t, J=7.2 Hz, 1H), 5.90 (t, J=6.2 Hz, 1H), 5.85 (d, J=7.5 Hz, 1H), 5.54 (d, J=8.4 Hz, 1H), 4.81 (d, J=49.8 Hz, 1H), 4.23 (d, J=6.2 Hz, 2H), 3.92 (q, J=10.7 Hz, 2H), 3.83 (s, 3H), 3.54 (d, J=27.9 Hz, 1H), 3.02 (t, J=10.5 Hz, 1H), 2.80 (d, J=11.3 Hz, 1H), 2.75 (d, J=4.5 Hz, 3H), 2.28-2.14 (m, 4H), 2.07 (t, J=11.2 Hz, 1H), 1.97 (ddd, J=24.0, 12.0, 3.2 Hz, 1H), 1.67 (dd, J=12.7, 2.7 Hz, 1H).

Example 1: 5-((3-(8-(((3S,4R)-3-Fluoro-1-methylpiperidin-4-yl)amino)-3-(2,2,2-trifluoroethyl)indolizin-2-yl)prop-2-yn-1-yl)amino)-6-methoxy-N-(methylsulfonyl)picolinamide (Cpd-1, i.e., Compound 1)

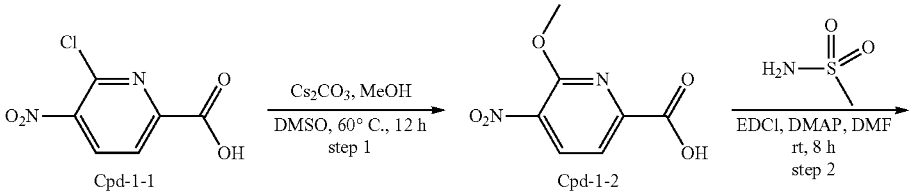

Cpd-1-1 Cpd-1-2

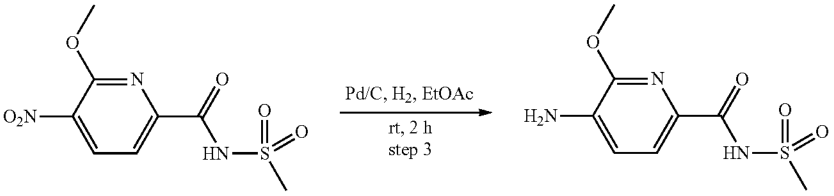

Cpd-1-3 Cpd-1-4

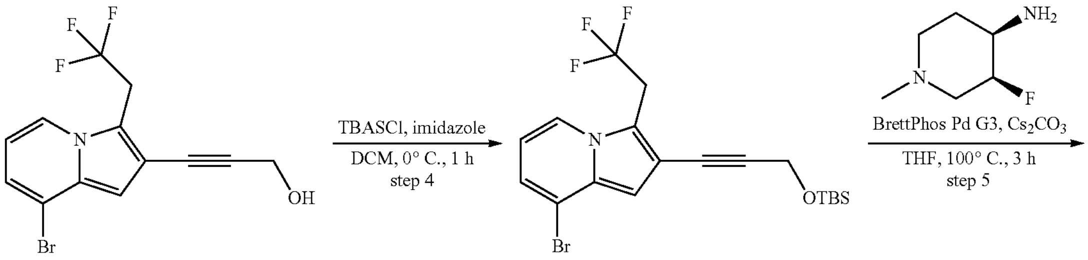

Int-1-7 Cpd-1-5

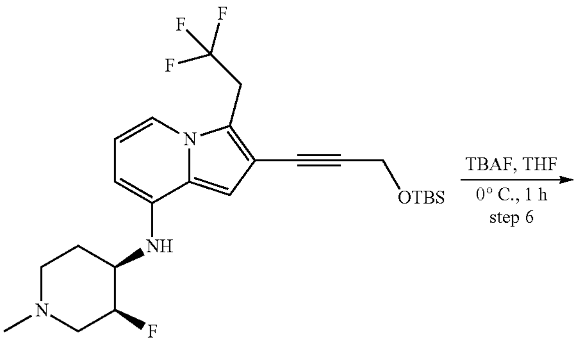

Cpd-1-6

-continued

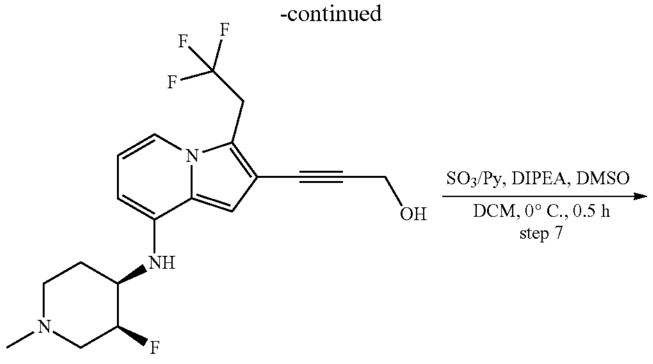

Cpd-1-7

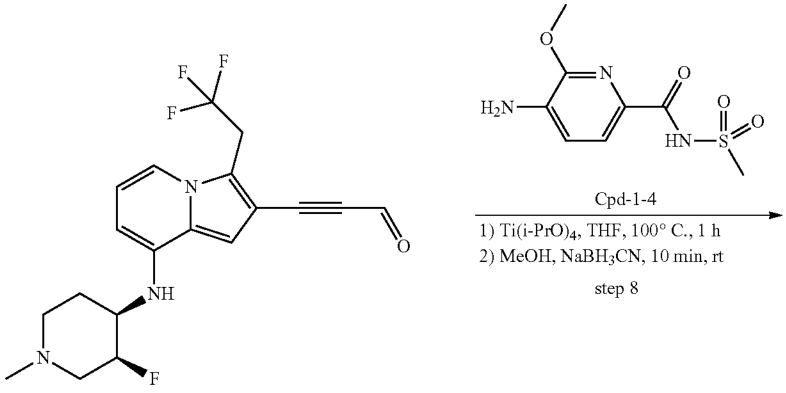

Cpd-1-8

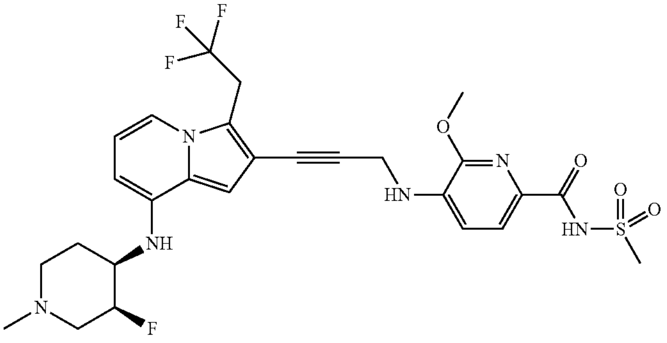

Cpd-1

Step 1: 6-Methoxy-5-nitropicolinic acid

A mixture of 6-chloro-5-nitropicolinic acid Cpd-1-1 (4.00 g, 19.7 mmol) and cesium carbonate (12.8 g, 39.4 mmol) in DMSO/MeOH (40 mL, 1:1) was stirred at 60° C. for 12 hours. LCMS detection showed that the starting material was completely consumed and the desired compound was detected. The reaction mixture was poured into icy water (50 mL), adjusted to pH=5 with 1N HCl, and extracted with EtOAc (30 mL×3). The organic layers were combined, dried over anhydrous $Na_2SO_4$, filtered, and concentrated to dryness under reduced pressure. The residue was purified by SGC (0 to 5% MeOH added to DCM) method to obtain 6-methoxy-5-nitropicolinic acid Cpd-1-2 (2.80 g, 71.7% yield, yellow solid). LCMS calculated for $C_7H_7N_2O_5$ $[M+H]^+$: m/z=199.0; found: 199.1.

Step 2: 6-Methoxy-N-(methylsulfonyl)-5-nitropicolinamide

A mixture of 6-methoxy-5-nitropicolinic acid Cpd-1-2 (3.20 g, 16.2 mmol), methanesulfonamide (1.54 g, 16.2 mmol), EDCI (4.65 g, 24.3 mmol), and 4-dimethylamino-pyridine (3.94 g, 32.4 mmol) in DMF (30 mL) was stirred at room temperature for 8 hours. LCMS detection showed that the starting material was completely consumed and the desired compound was detected. The reaction mixture was poured into water (100 mL) and extracted with EtOAc (30 mL×3). The organic layers were combined, washed with saturated brine (30 mL), dried over anhydrous $Na_2SO_4$, filtered, and concentrated to dryness under reduced pressure. The residue was purified by SGC (0 to 5% MeOH added to DCM) method to obtain 6-methoxy-N-(methylsulfonyl)-5-nitropicolinamide Cpd-1-3 (2.20 g, 49.5% yield, yellow solid). LCMS calculated for $C_8H_{10}N_3O_6S$ $[M+H]^+$: m/z=276.0; found: 276.1.

Step 3: 5-Amino-6-methoxy-N-(methylsulfonyl)picolinamide

Under hydrogen atmosphere, a mixture of palladium on carbon (1.60 g, 5% content) and 6-methoxy-N-(methylsulfonyl)-5-nitropicolinamide Cpd-1-3 (800 mg, 2.91 mmol) in EtOAc (15 mL) was stirred at room temperature for 2 hours. LCMS detection showed that the starting material was completely consumed and the desired compound was detected. The reaction mixture was filtered and concentrated to dryness under reduced pressure. The residue was purified by SGC (0 to 5% MeOH added to DCM) method to obtain 5-amino-6-methoxy-N-(methylsulfonyl)picolinamide Cpd-1-4 (500 mg, 70.1% yield, yellow solid). LCMS calculated for $C_8H_{12}N_3O_4S$ $[M+H]^+$: m/z=246.1; found: 246.0.

Step 4: 8-Bromo-2-(3-((tert-butyldimethylsilyl)oxy)prop-1-yn-1-yl)-3-(2,2,2-trifluoroethyl)indolizine tert-Butyldimethylchlorosilane (68.0 mg, 451 μmol) was added portionwise to a solution of 3-(8-bromo-3-(2,2,2-trifluoroethyl)indolizin-2-yl)prop-2-yn-1-ol Int-1-7 (100 mg, 302 μmol) and imidazole (61.3 mg, 901 μmol) in DCM (5 mL) at 0° C. The reaction mixture was stirred at 0° C. for 1 hour and then filtered to remove the solid. The filtrate was concentrated under reduced pressure to obtain a residue, which was purified by SGC (0 to 30% EtOAc added to PE) method to obtain 8-bromo-2-(3-((tert-butyldimethylsilyl)oxy)prop-1-yn-1-yl)-3-(2,2,2-trifluoroethyl)indolizine Cpd-1-5 (134 mg, 99.7% yield, yellow solid). LCMS calculated for $C_{19}H_{24}BrF_3NOSi$ $[M+H]^+$: m/z=446.1/448.1; found: 446.0/448.0.

Step 5: 2-(3-((tert-Butyldimethylsilyl)oxy)prop-1-yn-1-yl)-N-((3S,4R)-3-fluoro-1-methylpiperidin-4-yl)-3-(2,2,2-trifluoroethyl)indolizin-8-amine Under argon atmosphere, a mixture of 8-bromo-2-(3-((tert-butyldimethylsilyl)oxy)prop-1-yn-1-yl)-3-(2,2,2-trifluoroethyl)indolizine Cpd-1-5 (134 mg, 301 μmol), (3S,4R)-3-fluoro-1-methylpiperidin-4-amine (79.3 mg, 601 μmol), BrettPhos Pd G3 (54.4 mg, 60.0 μmol), and cesium carbonate (195 mg, 598 μmol) in THF (10 mL) was stirred at 100° C. for 3 hours. The reaction mixture was cooled to room temperature, filtered, and concentrated under reduced pressure. The residue was purified by SGC (0 to 7% methanol added to DCM) method to obtain 2-(3-((tert-butyldimethylsilyl)oxy)prop-1-yn-1-yl)-N-((3S,4R)-3-fluoro-1-methylpiperidin-4-yl)-3-(2,2,2-trifluoroethyl)indolizin-8-amine Cpd-1-6 (82.1 mg, 54.9% yield, white solid). LCMS calculated for $C_{25}H_{36}F_4N_3OSi$ $[M+H]^+$: m/z=498.3; found: 498.0.

Step 6: 3-(8-(((3S,4R)-3-Fluoro-1-methylpiperidin-4-yl)amino)-3-(2,2,2-trifluoroethyl)indolizin-2-yl)prop-2-yn-1-ol TBAF (0.20 mL, 0.20 mmol, 1M in THF) was added dropwise to a solution of 2-(3-((tert-butyldimethylsilyl)oxy)prop-1-yn-1-yl)-N-((3S,4R)-3-fluoro-1-methylpiperidin-4-yl)-3-(2,2,2-trifluoroethyl)indolizin-8-amine Cpd-1-6 (82.1 mg, 165 μmol) in THF (5 mL) at 0° C. The reaction mixture was stirred at 0° C. for 1 hour. LCMS detection showed that the starting material was completely consumed and the desired compound was detected. The reaction mixture was quenched with saturated sodium bicarbonate aqueous solution (50 mL) and extracted with EtOAc (50 mL×3). The organic layers were combined, dried over $Na_2SO_4$, filtered, and concentrated to dryness under reduced pressure. The residue was purified by SGC (0 to 5% MeOH added to DCM) method to obtain 3-(8-(((3S,4R)-3-fluoro-1-methylpiperidin-4-yl)amino)-3-(2,2,2-trifluoroethyl)indolizin-2-yl)prop-2-yn-1-ol Cpd-1-7 (57.0 mg, 90.2% yield, white solid). LCMS calculated for $C_{19}H_{22}F_4N_3O$ $[M+H]^+$: m/z=384.2; found: 384.1.

Step 7: 3-(8-(((3S,4R)-3-Fluoro-1-methylpiperidin-4-yl)amino)-3-(2,2,2-trifluoroethyl)indolizin-2-yl)propiolaldehyde A solution of pyridine sulfur trioxide (780 mg, 4.90 mmol) in DMSO (1 mL) was added dropwise to a solution of 3-(8-(((3S,4R)-3-fluoro-1-methylpiperidin-4-yl)amino)-3-(2,2,2-trifluoroethyl)indolizin-2-yl)prop-2-yn-1-ol Cpd-1-7 (625 mg, 1.63 mmol), DMSO (1.20 mL, 16.3 mmol), and diisopropylethylamine (1.50 mL, 8.15 mmol) in DCM (20 mL) at 0° C. The reaction mixture was stirred at 0° C. for 0.5 hours. LCMS detection showed that the starting material was completely consumed and the desired compound was detected. The reaction mixture was quenched with saturated sodium bicarbonate aqueous solution (100 mL) and extracted with EtOAc (100 mL×3). The organic layers were combined, dried over $Na_2SO_4$, filtered, and concentrated to dryness under reduced pressure. The residue was purified by SGC (0 to 5% MeOH added to DCM) method to obtain 3-(8-(((3S,4R)-3-fluoro-1-methylpiperidin-4-yl)amino)-3-(2,2,2-trifluoroethyl)indolizin-2-yl)propiolaldehyde Cpd-1-8 (550 mg, 88.6% yield, yellow solid). LCMS calculated for $C_{19}H_{20}F_4N_3O$ $[M+H]^+$: m/z=382.2; found: 382.1.

Step 8: 5-((3-(8-(((3S,4R)-3-Fluoro-1-methylpiperidin-4-yl)amino)-3-(2,2,2-trifluoroethyl)indolizin-2-yl)prop-2-yn-1-yl)amino)-6-methoxy-N-(methylsulfonyl)picolinamide A mixture of 3-(8-(((3S,4R)-3-fluoro-1-methylpiperidin-4-yl)amino)-3-(2,2,2-trifluoroethyl)indolizin-2-yl)propiolaldehyde Cpd-1-8 (50.0 mg, 131 μmol), 5-amino-6-methoxy-N-(methylsulfonyl)picolinamide Cpd-1-4 (38.6 mg, 157 μmol), and tetraisopropyl titanate (112 mg, 393 μmol) in THF (1 mL) was stirred at 100° C. for 1 hour. The mixed solution was then cooled to 0° C., slowly added with MeOH (0.5 mL) and sodium cyanoborohydride (12.4 mg, 197 μmol), and the reaction mixture was warmed to room temperature and stirred for another 10 minutes. LCMS detection showed that the starting material was completely consumed and the desired compound was detected. The reaction mixture was poured into icy water (5 mL) and extracted with EtOAc (20 mL×3). The organic layers were combined, washed with saturated sodium bicarbonate aqueous solution (20 mL), dried over anhydrous $Na_2SO_4$, filtered, and concentrated under reduced pressure. The residue was purified by SGC (0 to 3% MeOH added to DCM) method to obtain a crude product as a yellow solid, which was subjected to preparative purification to obtain 5-((3-(8-(((3S,4R)-3-fluoro-1-methylpiperidin-4-yl)amino)-3-(2,2,2-trifluoroethyl)indolizin-2-yl)prop-2-yn-1-yl)amino)-6-methoxy-N-(methylsulfonyl)picolinamide Cpd-1 (14.8 mg, 18.5% yield, yellow solid). LCMS calculated for $C_{27}H_{31}F_4N_6O_4S$ $[M+H]^+$: m/z=611.2; found: 611.9; $^1H$ NMR (400 MHZ, $CDCl_3$) δ 9.70 (s, 1H), 7.85 (d, J=8.0 Hz, 1H), 7.32 (d, J=7.0 Hz, 1H), 6.98 (d, J=8.0 Hz, 1H), 6.53 (t, J=7.2 Hz, 1H), 6.48 (s, 1H), 5.81 (d, J=7.3 Hz, 1H), 5.18 (t, J=5.9 Hz, 1H), 4.85 (d, J=49.1 Hz, 1H), 4.29 (d, J=6.0 Hz, 2H), 4.16 (d, J=9.4 Hz, 1H), 4.03 (s, 3H), 3.68 (q, J=10.1 Hz, 2H), 3.59-3.43 (m, 1H), 3.41 (s, 3H), 3.24 (t, J=11.0 Hz, 1H), 2.94 (d, J=11.0 Hz, 1H), 2.37-2.21 (m, 4H), 2.16 (t, J=11.1 Hz, 1H), 2.02 (d, J=10.0 Hz, 1H), 1.93 (td, J=12.2, 3.5 Hz, 1H).

Example 2: 5-((3-(8-(((3S,4R)-3-Fluoro-1-methylpiperidin-4-yl)amino)-3-(2,2,2-trifluoroethyl)indolizin-2-yl)prop-2-yn-1-yl)amino)-6-(methoxy-$d_3$)-N-(methylsulfonyl)picolinamide (Cpd-2, i.e., Compound 2)

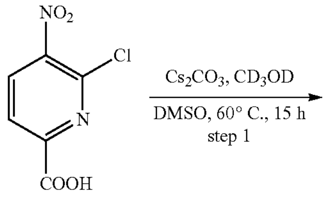

Int-1-1

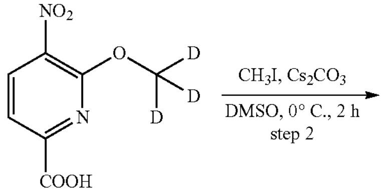

Cpd-2-1

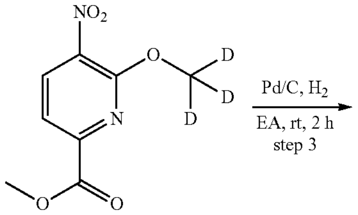

Cpd-2-2

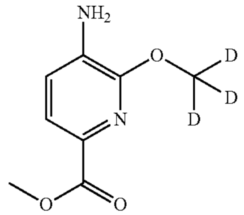

Cpd-2-3

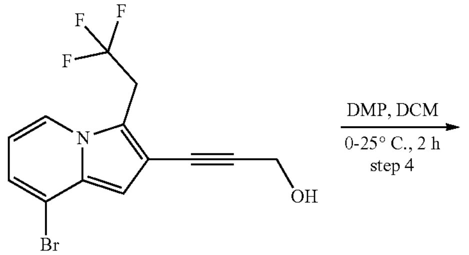

Int-1-7

-continued

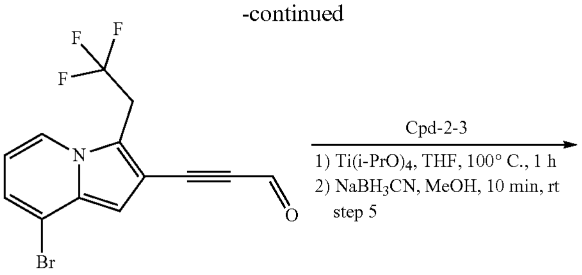

Int-2

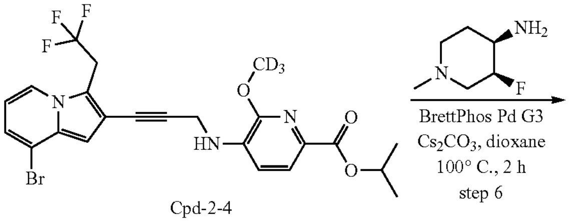

Cpd-2-4

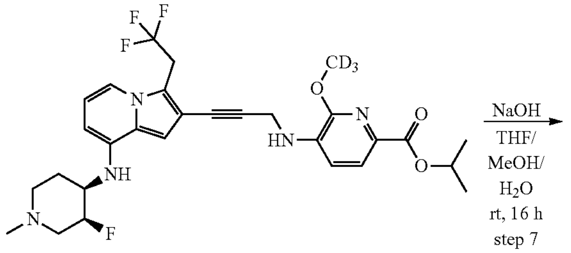

Cpd-2-5

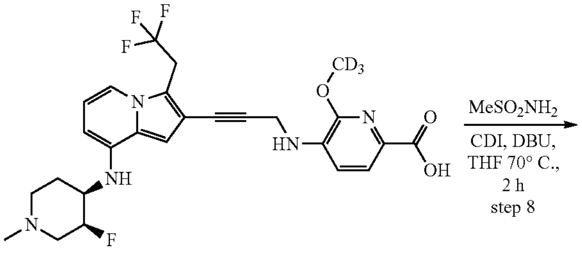

Cpd-2-6

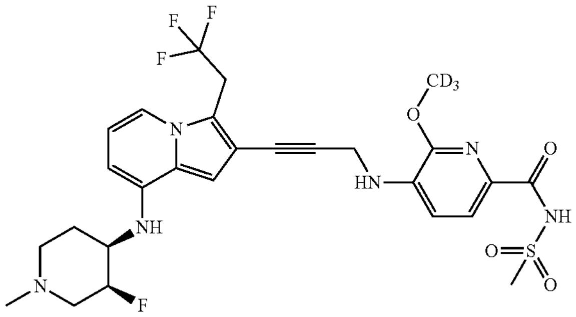

Cpd-2

Step 1: 6-(Methoxy-$d_3$)-5-nitropicolinic acid

Under nitrogen atmosphere, a mixture of 6-chloro-5-nitropicolinic acid Cpd-1-1 (20.0 g, 98.7 mmol), cesium carbonate (96.5 g, 296 mmol), and deuterated methanol (4.27 g, 118 mmol) in DMSO (200 mL) was stirred at 60° C. for 16 hours. After the completion of the reaction detected by LCMS, the mixture was diluted with water (100 mL) and the pH was adjusted to 3 with 1N HCl. The mixture was filtered to collect the precipitate, and the filter cake was dried under vacuum to obtain 6-(methoxy-$d_3$)-5-nitropicolinic acid Cpd-2-1 (12.0 g, crude product, yellow solid). The crude product was used directly in the next step reaction. LCMS calculated for $C_7H_4D_3N_2O_5$ $[M+H]^+$: m/z=202.1; found: 201.9.

Step 2: Methyl 6-(methoxy-$d_3$)-5-nitropicolinate

Under nitrogen atmosphere, a mixture of 6-(methoxy-$d_3$)-5-nitropicolinic acid Cpd-2-1 (12.0 g, 59.7 mmol) and cesium carbonate (58.4 g, 179 mmol) in DMSO (120 mL) was stirred at 0° C. for 0.5 hours. Iodomethane (9.32 g, 179 mmol) was then added, and the resulting reaction mixture was stirred at 0° C. for 2 hours. After the completion of the reaction detected by LCMS, the reaction mixture was poured into icy ammonium chloride aqueous solution (1000 mL) and extracted with EtOAc (1000 mL×2). The combined organic layers were dried over anhydrous $Na_2SO_4$, filtered, and concentrated to obtain a crude product. The residue was purified by SGC (0 to 20% EtOAc added to PE) method to obtain methyl 6-(methoxy-$d_3$)-5-nitropicolinate Cpd-2-2 (10.0 g, 70.1% yield, yellow solid). LCMS calculated for $CH_6D_3N_2O_5$ $[M+H]^+$: m/z=216.1; found: 215.9.

Step 3: Methyl 5-amino-6-(methoxy-$d_3$)picolinate

Methyl 6-(methoxy-$d_3$)-5-nitropicolinate Cpd-2-2 (10.0 g, 46.5 mmol) was dissolved in EtOAc (100 mL), then palladium on carbon (9.90 g, 5% content) was added thereto, and the resulting mixture was stirred for 2 hours at room temperature under hydrogen atmosphere. LCMS detection showed that the starting material was completely consumed and the desired compound was detected. The reaction mixture was filtered and concentrated to obtain methyl 5-amino-6-(methoxy-$d_3$)picolinate Cpd-2-3 (8.20 g, 90.5% yield, yellow solid). LCMS calculated for $C_8H_8D_3N_2O_3$ $[M+H]^+$: m/z=186.1; found: 186.2; $^1$H NMR (400 MHZ, DMSO-$d_6$) δ 7.53 (d, J=8.0 Hz, 1H), 6.85 (d, J=8.0 Hz, 1H), 5.88 (s, 2H), 3.75 (s, 3H).

Step 4: 3-(8-Bromo-3-(2,2,2-trifluoroethyl)indolizin-2-yl)propiolaldehyde

DMP (17.4 g, 41.0 mmol) was slowly added portionwise to a solution of 3-(8-bromo-3-(2,2,2-trifluoroethyl)indolizin-2-yl)prop-2-yn-1-ol Int-1-7 (6.80 g, 20.5 mmol) in DCM (120 mL) in an ice bath. Then the mixture was stirred at room temperature for 2 hours. The reaction was quenched with saturated sodium bicarbonate aqueous solution (50 mL) and extracted with DCM (30 mL×3). The organic phases were combined and concentrated under vacuum. The residue was purified by SGC (0 to 15% EtOAc added to PE) method to obtain 3-(8-bromo-3-(2,2,2-trifluoroethyl)indolizin-2-yl) propiolaldehyde Int-2 (5.70 g, 84.3% yield, gray solid). LCMS calculated for $C_{13}H_8BrF_3NO$ $[M+H]^+$: m/z=330.0/332.0; found: 330.2/332.2; $^1$H NMR (400 MHz, DMSO-$d_6$) δ 9.47 (s, 1H), 8.49 (d, J=7.1 Hz, 1H), 7.28 (d, J=7.1 Hz, 1H), 6.90 (s, 1H), 6.78 (t, J=7.1 Hz, 1H), 4.31 (q, J=10.7 Hz, 2H).

Step 5: Isopropyl 5-((3-(8-bromo-3-(2,2,2-trifluoroethyl)indolizin-2-yl)prop-2-yn-1-yl)amino)-6-(methoxy-$d_3$)picolinate Under nitrogen atmosphere, a solution of 3-(8-bromo-3-(2,2,2-trifluoroethyl)indolizin-2-yl)propiolaldehyde Int-2 (200 mg, 606 µmol), methyl 5-amino-6-(methoxy-$d_3$)picolinate Cpd-2-3 (135 mg, 730 µmol), and tetraisopropyl titanate (517 mg, 1.82 mmol) in THF (2 mL) was stirred at 100° C. for 1 hour. The reaction mixture was cooled to 25° C., then added with MeOH (2 mL) and sodium cyanoborohydride (57.1 mg, 0.91 mmol), and stirred for another 10 minutes. LCMS detection showed that the starting material was completely consumed and the desired compound was detected. The reaction mixture was diluted with water (20 mL) and extracted with EtOAc (20 mL×3). The combined organic layers were washed with saturated brine (50 mL), dried over anhydrous $Na_2SO_4$, filtered, and concentrated. The residue was purified by SGC (0 to 25% EtOAc added to PE) method to obtain isopropyl 5-((3-(8-bromo-3-(2,2,2-trifluoroethyl)indolizin-2-yl)prop-2-yn-1-yl)amino)-6-(methoxy-$d_3$)picolinate Cpd-2-4 (190 mg, 59.4% yield, yellow solid). LCMS calculated for $C_{23}H_{19}D_3BrF_3N_3O_3$ $[M+H]^+$: m/z=527.1/529.1; found: 526.9/529.0.

Step 6: Isopropyl 5-((3-(8-(((3S,4R)-3-fluoro-1-methylpiperidin-4-yl)amino)-3-(2,2,2-trifluoroethyl)indolizin-2-yl)prop-2-yn-1-yl)amino)-6-(methoxy-$d_3$)picolinate Under nitrogen atmosphere, a solution of isopropyl 5-((3-(8-bromo-3-(2,2,2-trifluoroethyl)indolizin-2-yl)prop-2-yn-1-yl)amino)-6-(methoxy-$d_3$)picolinate Cpd-2-4 (170 mg, 322 µmol), (3S,4R)-3-fluoro-1-methylpiperidin-4-amine (85.1 mg, 645 µmol), Brettphos Pd G3 (58.3 mg, 64.3 µmol), and cesium carbonate (210 mg, 644 µmol) in 1,4-dioxane (2 mL) was stirred at 100° C. for 2 hours in a sealed tube. LCMS detection showed that the starting material was completely consumed and the desired compound was detected. The reaction mixture was filtered, and the filtrate was concentrated under reduced pressure. The crude product was subjected to preparative purification to obtain isopropyl 5-((3-(8-(((3S,4R)-3-fluoro-1-methylpiperidin-4-yl)amino)-3-(2,2,2-trifluoroethyl)indolizin-2-yl)prop-2-yn-1-yl)amino)-6-(methoxy-$d_3$)picolinate Cpd-2-5 (90.0 mg, 48.1% yield, yellow solid). LCMS calculated for $C_{29}H_{31}D_3F_4NO_3$ $[M+H]^+$: m/z=579.3; found: 579.0.

Step 7: 5-((3-(8-(((3S,4R)-3-Fluoro-1-methylpiperidin-4-yl)amino)-3-(2,2,2-trifluoroethyl)indolizin-2-yl)prop-2-yn-1-yl)amino)-6-(methoxy-$d_3$)picolinic acid A mixture of isopropyl 5-((3-(8-(((3S,4R)-3-fluoro-1-methylpiperidin-4-yl)amino)-3-(2,2,2-trifluoroethyl)indolizin-2-yl)prop-2-yn-1-yl)amino)-6-(methoxy-$d_3$)picolinate Cpd-2-5 (40.0 mg, 69.2 µmol) and sodium hydroxide (8.28 mg, 207 µmol) in THF (0.4 mL), MeOH (0.2 mL), and water (0.1 mL) was stirred at room temperature for 16 hours. LCMS detection showed that the starting material was completely consumed and the desired compound was detected. The reaction mixture was concentrated under reduced pressure, diluted with water, adjusted to pH=5 with diluted HCl, and filtered. The residue was purified by SGC (0 to 3% MeOH added to DCM) method to obtain a crude product, which was then subjected to preparative purification to obtain 5-((3-(8-(((3S,4R)-3-fluoro-1-methylpiperidin-4-yl)amino)-3-(2,2,2-trifluoroethyl)indolizin-2-yl)prop-2-yn-1-yl)amino)-6-(methoxy-$d_3$)picolinic acid Cpd-2-6 (5.50 mg, 15.0% yield, white solid). LCMS calculated for $C_{26}H_{25}D_3F_4N_5O_3$ $[M+H]^+$: m/z=537.2; found: 537.0; $^1$H NMR (400 MHz, $CD_3OD$) δ 7.64 (d, J=7.3 Hz, 1H), 7.36 (d, J=6.9 Hz, 1H), 6.94 (d, J=7.8 Hz, 1H), 6.56 (s, 1H), 6.42 (t, J=7.2 Hz, 1H), 5.79 (d, J=7.3 Hz, 1H), 4.90 (s, 1H), 4.19 (s, 2H), 3.69 (q, J=10.5 Hz, 2H), 3.62-3.54 (m, 1H), 3.32-3.23 (m, 1H), 3.01 (d, J=12.2 Hz, 1H), 2.62-2.48 (m, 1H), 2.46-2.39 (m, 1H), 2.37 (s, 3H), 2.00-1.87 (m, 2H).

Step 8: 5-((3-(8-(((3S,4R)-3-Fluoro-1-methylpiperidin-4-yl)amino)-3-(2,2,2-trifluoroethyl)indolizin-2-yl)prop-2-yn-1-yl)amino)-6-(methoxy-$d_3$)-N-(methylsulfonyl)picolinamide A solution of 5-((3-(8-(((3S,4R)-3-fluoro-1-methylpiperidin-4-yl)amino)-3-(2,2,2-trifluoroethyl)indolizin-2-yl)prop-2-yn-1-yl)amino)-6-(methoxy-$d_3$)picolinic acid Cpd-2-6 (210 mg, 392 μmol) and CDI (127 mg, 784 μmol) in THF (8 mL) was stirred at 70° C. for 1 hour under argon atmosphere and then cooled to room temperature. Methanesulfonamide (74.5 mg, 784 μmol) was added to the reaction mixture and stirred for 10 minutes, then DBU (120 μL, 789 μmol) was added thereto and stirred for another 1 hour at 70° C. The mixture was concentrated, then water (30 mL) was added, and the aqueous phase was extracted with EtOAc (50 mL×3). The combined organic phases were washed with brine (50 mL×3), dried over anhydrous $Na_2SO_4$, filtered, and the filtrate was concentrated under vacuum. The residue was subjected to preparative purification to obtain 5-((3-(8-(((3S,4R)-3-fluoro-1-methylpiperidin-4-yl)amino)-3-(2,2,2-trifluoroethyl)indolizin-2-yl)prop-2-yn-1-yl)amino)-6-(methoxy-$d_3$)-N-(methylsulfonyl)picolinamide Cpd-2 (50.0 mg, 20.8% yield, white solid). LCMS calculated for $C_{27}H_{28}D_3F_4N_6O_4S$ $[M+H]^+$: m/z=614.2; found: 614.4; $^1H$ NMR (400 MHZ, DMSO-$d_6$) δ 10.85 (s, 1H), 7.67 (d, J=8.0 Hz, 1H), 7.58 (d, J=6.9 Hz, 1H), 7.07 (d, J=8.1 Hz, 1H), 6.91 (s, 1H), 6.74 (s, 1H), 6.51 (t, J=7.2 Hz, 1H), 5.86 (d, J=7.5 Hz, 1H), 5.56 (d, J=8.4 Hz, 1H), 4.83 (d, J=49.6 Hz, 1H), 4.28 (d, J=6.0 Hz, 2H), 4.05 (s, 1H), 3.95 (q, J=10.7 Hz, 2H), 3.65-3.46 (m, 1H), 3.06 (t, J=11.0 Hz, 1H), 2.84 (d, J=11.5 Hz, 1H), 2.37-2.23 (m, 1H), 2.22 (s, 3H), 2.13 (t, J=11.3 Hz, 1H), 2.04-1.92 (m, 1H), 1.75-1.64 (m, 1H).

Example 3: 5-((3-(8-(((3S,4R)-3-Fluoro-1-methylpiperidin-4-yl)amino)-3-(2,2,2-trifluoroethyl)indolizin-2-yl)prop-2-yn-1-yl)amino)-4-methoxy-N-(methylsulfonyl)pyrimidine-2-carboxamide (Cpd-3, i.e., Compound 3)

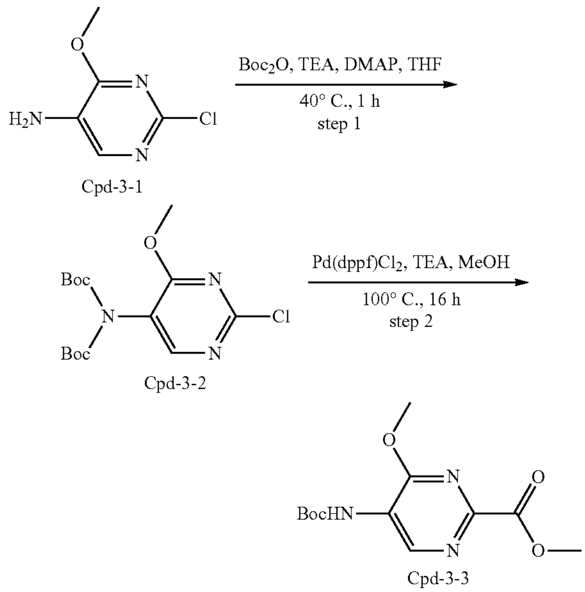

Cpd-3-1

Cpd-3-2

Cpd-3-3

-continued

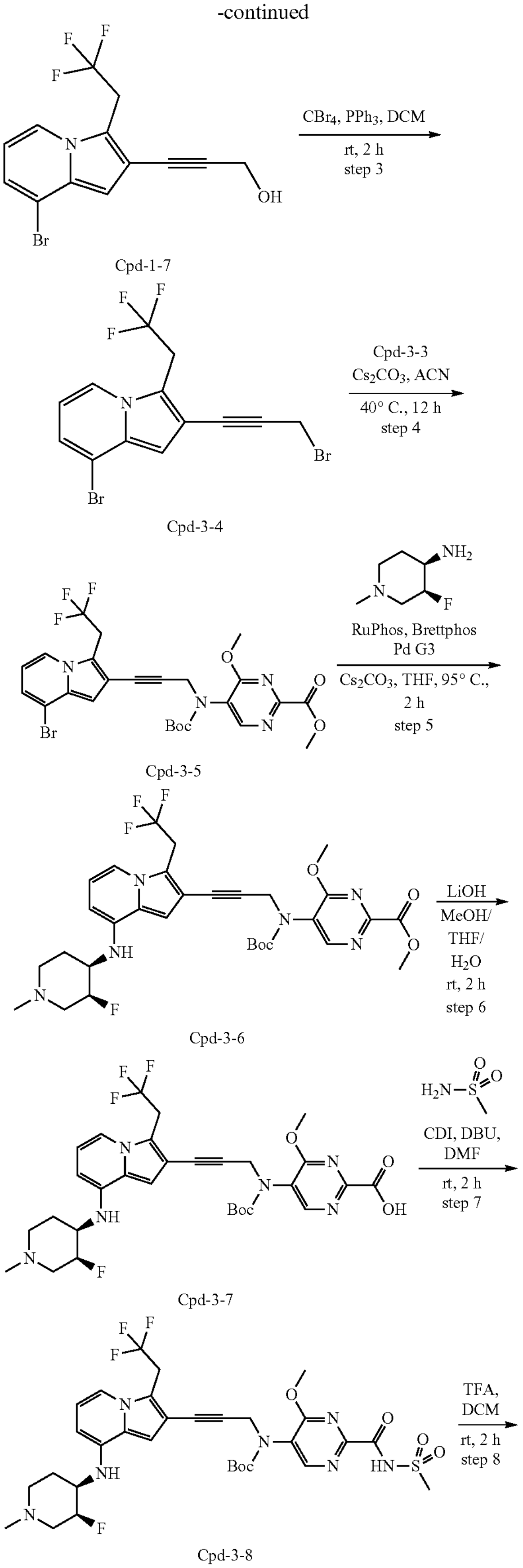

Cpd-1-7

Cpd-3-4

Cpd-3-5

Cpd-3-6

Cpd-3-7

Cpd-3-8

-continued

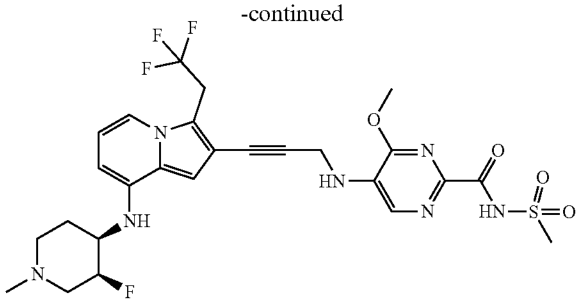

Cpd-3

Step 1: tert-Butyl (tert-butoxycarbonyl)(2-chloro-4-methoxypyrimidin-5-yl)carbamate Under nitrogen atmosphere, a mixture of 2-chloro-4-methoxypyrimidin-5-amine Cpd-3-1 (5.00 g, 3.13 mmol), di-tert-butyl dicarbonate (14.4 g, 6.57 mmol), triethylamine (15.8 g, 15.7 mmol), and 4-dimethylaminopyridine (383 mg, 3.13 mmol) in THF (50 mL) was stirred at 40° C. for 1 hour. LCMS detection showed that the starting material was completely consumed and the desired compound was detected. The reaction mixture was diluted with water (100 mL) and extracted with EtOAc (50 mL×3). The combined organic layers were washed with saturated brine (50 mL), dried over anhydrous $Na_2SO_4$, filtered, and concentrated. The residue was purified by SGC (0 to 5% EtOAc added to PE) method to obtain tert-butyl (tert-butoxycarbonyl)(2-chloro-4-methoxypyrimidin-5-yl)carbamate Cpd-3-2 (4.80 g, 42.5% yield, white solid). LCMS calculated for $C_{15}H_{23}ClN_3O_5$ $[M+H]^+$: m/z=360.1; found: 360.2.

Step 2: Methyl 5-((tert-butoxycarbonyl)amino)-4-methoxypyrimidine-2-carboxylate

Under carbon monoxide atmosphere, a mixture of tert-butyl (tert-butoxycarbonyl)(2-chloro-4-methoxypyrimidin-5-yl)carbamate Cpd-3-2 (4.30 g, 11.9 mmol), Pd(dppf)$Cl_2$ (1.72 g, 2.38 mmol), and triethylamine (3.61 g, 35.7 mmol) in MeOH (43 mL) was stirred at 100° C. for 16 hours. LCMS detection showed that the starting material was completely consumed and the desired compound was detected. The reaction mixture was filtered and concentrated under reduced pressure. The residue was diluted with water (100 mL) and extracted with EtOAc (100 mL×3). The combined organic layers were washed with saturated brine (50 mL), dried over anhydrous $Na_2SO_4$, filtered, and concentrated. The residue was purified by SGC (0 to 20% EtOAc added to PE) method to obtain methyl 5-((tert-butoxycarbonyl)amino)-4-methoxypyrimidine-2-carboxylate Cpd-3-3 (2.00 g, 59.0% yield, white solid). LCMS calculated for $C_{12}H_{18}N_3O_5$ $[M+H]^+$: m/z=284.1; found: 284.1.

Step 3: 8-Bromo-2-(3-bromoprop-1-yn-1-yl)-3-(2,2,2-trifluoroethyl)indolizine

At room temperature, 3-(8-bromo-3-(2,2,2-trifluoroethyl)indolizin-2-yl)prop-2-yn-1-ol Cpd-1-7 (2.00 g, 6.02 mmol) and triphenylphosphine (3.16 g, 12.0 mmol) were dissolved in DCM (30 mL) and stirred for 10 minutes, then carbon tetrabromide (3.00 g, 9.03 mmol) was added thereto. The reaction mixture was stirred at room temperature for 2 hours. LCMS detection showed that the starting material was completely consumed and the desired compound was detected. The reaction mixture was diluted with water (50 mL) and extracted with EtOAc (50 mL×3). The combined organic layers were washed with saturated brine (50 mL), dried over anhydrous $Na_2SO_4$, filtered, and concentrated. The residue was purified by SGC (0 to 10% EtOAc added to PE) method to obtain 8-bromo-2-(3-bromoprop-1-yn-1-yl)-3-(2,2,2-trifluoroethyl)indolizine Cpd-3-4 (1.55 g, 53.0% yield, white solid). LCMS calculated for $C_{13}H_9Br_2F_3N$ $[M+H]^+$: m/z=393.9/395.9/397.9; found: 394.0/396.0/398.0.

Step 4: Methyl 5-((3-(8-bromo-3-(2,2,2-trifluoroethyl)indolizin-2-yl)prop-2-yn-1-yl)(tert-butoxycarbonyl)amino)-4-methoxypyrimidine-2-carboxylate Under nitrogen atmosphere, a mixture of 8-bromo-2-(3-bromoprop-1-yn-1-yl)-3-(2,2,2-trifluoroethyl)indolizine Cpd-3-4 (1.37 g, 3.46 mmol), methyl 5-((tert-butoxycarbonyl)amino)-4-methoxypyrimidine-2-carboxylate Cpd-3-3 (980 mg, 3.46 mmol), and cesium carbonate (1.88 g, 13.8 mmol) in acetonitrile (20 mL) was stirred at 40° C. for 12 hours. LCMS detection showed that the starting material was completely consumed and the desired compound was detected. The reaction mixture was cooled to room temperature and filtered, and the filtrate was concentrated under reduced pressure. The residue was purified by SGC (0 to 25% EtOAc added to PE) method to obtain methyl 5-((3-(8-bromo-3-(2,2,2-trifluoroethyl)indolizin-2-yl)prop-2-yn-1-yl)(tert-butoxycarbonyl)amino)-4-methoxypyrimidine-2-carboxylate Cpd-3-5 (1.60 g, 65.1% yield, white solid). LCMS calculated for $C_{25}H_{25}BrF_3N_4O_5$ $[M+H]^+$: m/z=597.1/599.1; found: 597.2/599.2.

Step 5: Methyl 5-((tert-butoxycarbonyl)(3-(8-(((3S,4R)-3-fluoro-1-methylpiperidin-4-yl)amino)-3-(2,2,2-trifluoroethyl)indolizin-2-yl)prop-2-yn-1-yl)amino)-4-methoxypyrimidine-2-carboxylate Under atmosphere, a mixture of methyl 5-((3-(8-bromo-3-(2,2,2-trifluoroethyl)indolizin-2-yl)prop-2-yn-1-yl)(tert-butoxycarbonyl)amino)-4-methoxypyrimidine-2-carboxylate Cpd-3-5 (1.35 g, 2.26 mmol), (3S,4R)-3-fluoro-1-methylpiperidin-4-amine (448 mg, 3.39 mmol), Brettphos Pd G3 (205 mg, 226 μmol), Ruphos (211 mg, 452 μmol), and cesium carbonate (1.47 g, 4.52 mmol) in THF (20 mL) was stirred at 95° C. for 2 hours in a sealed tube. LCMS detection showed that the starting material was completely consumed and the desired compound was detected. The reaction mixture was cooled to room temperature and filtered, and the filtrate was concentrated under reduced pressure. The residue was purified by SGC (0 to 5% MeOH added to DCM) method to obtain methyl 5-((tert-butoxycarbonyl)(3-(8-(((3S,4R)-3-fluoro-1-methylpiperidin-4-yl)amino)-3-(2,2,2-trifluoroethyl)indolizin-2-yl)prop-2-yn-1-yl)amino)-4-methoxypyrimidine-2-carboxylate Cpd-3-6 (1.20 g, crude product, yellow solid). LCMS calculated for $C_{31}H_{37}F_4N_6O_5$ $[M+H]^+$: m/z=649.3; found: 649.2.

Step 6: 5-((tert-Butoxycarbonyl)(3-(8-(((3S,4R)-3-fluoro-1-methylpiperidin-4-yl)amino)-3-(2,2,2-trifluoroethyl)indolizin-2-yl)prop-2-yn-1-yl)amino)-4-methoxypyrimidine-2-carboxylic acid At room temperature, methyl 5-((tert-butoxycarbonyl)(3-(8-(((3S,4R)-3-fluoro-1-methylpiperidin-4-yl)amino)-3-(2,2,2-trifluoroethyl)indolizin-2-yl)prop-2-yn-1-yl)amino)-4- methoxypyrimidine-2-carboxylate Cpd-3-6 (1.20 g, 1.85 mmol) was dissolved in a mixed solvent of THF (8 mL), MeOH (8 mL) and water (2 mL), and lithium hydroxide (443 mg, 18.5 mmol) were added thereto. The system was stirred at room temperature for 2 hours. LCMS detection showed that the starting material was completely consumed and the desired compound was detected. The reaction mixture was adjusted to pH=4 with 1N HCl, diluted with water (20 mL), and extracted with DCM (20 mL×3). The combined organic phases were dried over anhydrous $Na_2SO_4$ and concentrated under reduced pressure to obtain 5-((tert-butoxycarbonyl)(3-(8-(((3S,4R)-3-fluoro-1-methylpiperidin-4-yl)amino)-3-(2,2,2-trifluoroethyl)indolizin-2-yl)prop-2-yn-1-yl)amino)-4-methoxypyrimidine-2-carboxylic acid Cpd-3-7 (400 mg, crude product, yellow solid). LCMS calculated for $C_{30}H_{35}F_4N_6O_5$ $[M+H]^+$: m/z=635.3; found: 635.5.

Step 7: tert-Butyl (3-(8-(((3S,4R)-3-fluoro-1-methylpiperidin-4-yl)amino)-3-(2,2,2-trifluoroethyl)indolizin-2-yl)prop-2-yn-1-yl)(4-methoxy-2-((methylsulfonyl)carbamoyl)pyrimidin-5-yl)carbamate A solution of 5-((tert-butoxycarbonyl)(3-(8-(((3S,4R)-3-fluoro-1-methylpiperidin-4-yl)amino)-3-(2,2,2-trifluoroethyl)indolizin-2-yl)prop-2-yn-1-yl)amino)-4-methoxypyrimidine-2-carboxylic acid Cpd-3-7 (260 mg, 410 μmol) and CDI (133 mg, 820 μmol) in DMF (4 mL) was stirred at 90° C. for 2 hours. The reaction mixture was cooled to room temperature, and then methanesulfonamide (78.0 mg, 820 μmol) and DBU (206 mg, 820 μmol) were added thereto. The reaction mixture was stirred at 90° C. for another 2 hours. LCMS detection showed that the starting material was completely consumed and the desired compound was detected. The reaction mixture was cooled to room temperature, diluted with water (50 mL), and extracted with DCM (50 mL×3). The combined organic layers were washed with saturated brine (50 mL), dried over anhydrous $Na_2SO_4$, filtered, and concentrated. The residue was purified by Prep-HPLC to obtain tert-butyl (3-(8-(((3S,4R)-3-fluoro-1-methylpiperidin-4-yl)amino)-3-(2,2,2-trifluoroethyl)indolizin-2-yl)prop-2-yn-1-yl)(4-methoxy-2-((methylsulfonyl)carbamoyl)pyrimidin-5-yl)carbamate Cpd-3-8 (100 mg, crude product, yellow solid). LCMS calculated for $C_{31}H_{38}F_4N_7O_6S$ $[M+H]^+$: m/z=711.3; found: 711.6.

Step 8: 5-((3-(8-(((3S,4R)-3-Fluoro-1-methylpiperidin-4-yl)amino)-3-(2,2,2-trifluoroethyl)indolizin-2-yl)prop-2-yn-1-yl)amino)-4-methoxy-N-(methylsulfonyl)pyrimidine-2-carboxamide Trifluoroacetic acid (1 mL) was added to a solution of tert-butyl (3-(8-(((3S,4R)-3-fluoro-1-methylpiperidin-4-yl)amino)-3-(2,2,2-trifluoroethyl)indolizin-2-yl)prop-2-yn-1-yl)(4-methoxy-2-((methylsulfonyl)carbamoyl)pyrimidin-5-yl)carbamate Cpd-3-8 (100 mg, 141 μmol) in DCM (3 mL) at 0° C. The reaction mixture was slowly warmed to room temperature and stirred for 2 hours. LCMS detection showed that the starting material was completely consumed and the desired compound was detected. The reaction mixture was added dropwise to a mixture of saturated sodium bicarbonate solution (10 mL) and icy water (15 mL), and extracted with DCM (10 mL×3). The combined organic layers were washed with saturated brine (50 mL), dried over anhydrous $Na_2SO_4$, filtered, and concentrated. The residue was purified by Prep-HPLC to obtain 5-((3-(8-(((3S,4R)-3-fluoro-1-methylpiperidin-4-yl)amino)-3-(2,2,2-trifluoroethyl)indolizin-2-yl)prop-2-yn-1-yl)amino)-4-methoxy-N-(methylsulfonyl)pyrimidine-2-carboxamide Cpd-3 (8.05 mg, 8.8% yield, yellow solid). LCMS calculated for $C_{26}H_{30}F_4N_7O_4S$ $[M+H]^+$: m/z=612.2; found: 612.2; $^1H$ NMR (400 MHz, DMSO-$d_6$) δ 8.05 (s, 1H), 7.60 (d, J=6.8 Hz, 1H), 6.93 (s, 1H), 6.80-6.70 (m, 1H), 6.52 (t, J=7.2 Hz, 1H), 5.86 (s, 1H), 5.64 (d, J=8.3 Hz, 1H), 4.87 (d, J=52.8 Hz, 1H), 4.32 (d, J=6.1 Hz, 2H), 4.05 (s, 3H), 4.02-3.90 (m, 2H), 3.60 (d, J=10.3 Hz, 1H), 3.23 (s, 3H), 3.18-3.08 (m, 1H), 2.91 (d, J=10.9 Hz, 1H), 2.28 (s, 3H), 2.05-1.94 (m, 1H), 1.78-1.67 (m, 1H), 1.23 (s, 2H).

Example 4: N-(Cyclopropylsulfonyl)-5-((3-(8-(((3S,4R)-3-fluoro-1-methylpiperidin-4-yl)amino)-3-(2,2,2-trifluoroethyl)indolizin-2-yl)prop-2-yn-1-yl)amino)-6-(methoxy-$d_3$)picolinamide (Cpd-4, i.e., Compound 4)

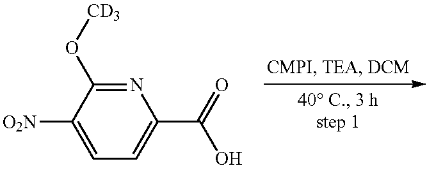

Cpd-2-1

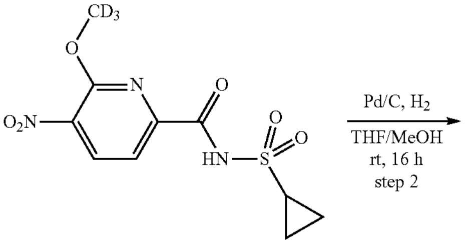

Cpd-4-1

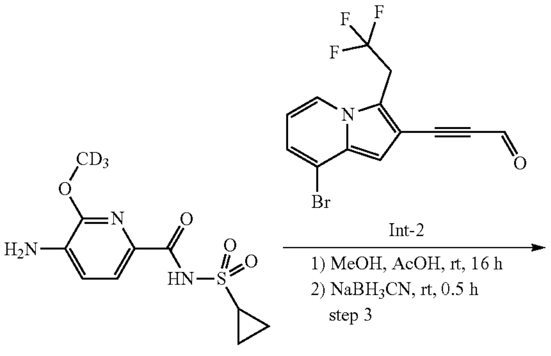

Cpd-4-2

-continued

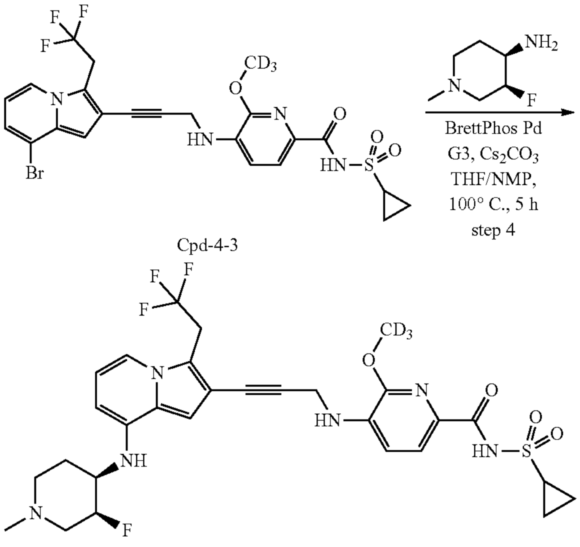

Cpd-4-3

Cpd-4

Step 1: N-(Cyclopropylsulfonyl)-6-(methoxy-$d_3$)-5-nitropicolinamide

At room temperature, cyclopropylsulfonamide (1.33 g, 10.9 mmol) and triethylamine (3.32 g, 32.8 mmol) were sequentially added to a solution of 6-(methoxy-$d_3$)-5-nitropicolinic acid Cpd-2-1 (2.20 g, 10.9 mmol) and 2-chloro-1-methylpyridinium iodide (3.35 g, 13.1 mmol) in dichloromethane (40 mL). The reaction mixture was stirred at 40° C. for 3 hours. LCMS detection showed that the starting material was completely consumed and the desired compound was detected. The reaction mixture was concentrated under reduced pressure, and the residue was diluted with water (100 mL). The pH was adjusted to 2 with 1N HCl aqueous solution. The precipitated solid was filtered, washed with water (100 mL), dried over anhydrous $Na_2SO_4$, filtered, and concentrated to obtain N-(cyclopropylsulfonyl)-6-(methoxy-$d_3$)-5-nitropicolinamide Cpd-4-1 (1.00 g, crude product, yellow solid). The crude product was used directly in the next step reaction. LCMS calculated for $C_{10}H_7D_3N_3O_6S$ $[M-H]^-$: m/z=303.1; found: 303.2.

Step 2: 5-Amino-N-(cyclopropylsulfonyl)-6-(methoxy-$d_3$)picolinamide

At room temperature, a mixture of N-(cyclopropylsulfonyl)-6-(methoxy-$d_3$)-5-nitropicolinamide Cpd-4-1 (1.00 g, 3.29 mmol, crude product) and palladium on carbon (350 mg, 5% content) in THF (15 mL) and MeOH (15 mL) was stirred for 16 hours under hydrogen atmosphere. LCMS detection showed that the starting material was completely consumed and the desired compound was detected. The reaction mixture was filtered and concentrated under reduced pressure to obtain 5-amino-N-(cyclopropylsulfonyl)-6-(methoxy-$d_3$)picolinamide Cpd-4-2 (730 mg, crude product, yellow solid). The crude product was used directly in the next step reaction. LCMS calculated for $C_{10}H_9D_3N_3O_4S$ $[M-H]^-$: m/z=273.1; found: 273.3.

Step 3: 5-((3-(8-Bromo-3-(2,2,2-trifluoroethyl)indolizin-2-yl)prop-2-yn-1-yl)amino)-N-(cyclopropylsulfonyl)-6-(methoxy-$d_3$)picolinamide 3-(8-Bromo-3-(2,2,2-trifluoroethyl)indolizin-2-yl)propiolaldehyde Int-2 (500 mg, 1.51 mmol), 5-amino-N-(cyclopropylsulfonyl)-6-(methoxy-$d_3$)picolinamide Cpd-4-2 (395 mg, 1.44 mmol), and acetic acid (91.0 mg, 1.51 mmol) were dissolved in MeOH (6 mL) and DCM (4 mL), and the system was stirred at room temperature for 16 hours. Then $NaBH_3CN$ (286 mg, 4.54 mmol) was added thereto, and the system was stirred for another 0.5 hours. LCMS detection showed that the starting material was completely consumed and the desired compound was detected. The reaction mixture was diluted with water (40 mL) and filtered to collect the filter cake. The filter cake was purified by slurrying with methanol to obtain 5-((3-(8-bromo-3-(2,2,2-trifluoroethyl)indolizin-2-yl)prop-2-yn-1-yl)amino)-N-(cyclopropylsulfonyl)-6-(methoxy-$d_3$)picolinamide Cpd-4-3 (560 mg, 62.8% yield, yellow solid). LCMS calculated for $C_{23}H_{16}BrD_3F_3N_4O_4S$ $[M-H]^-$: m/z=586.1/588.1; found: 586.2/588.2.

Step 4: N-(Cyclopropylsulfonyl)-5-((3-(8-(((3S,4R)-3-fluoro-1-methylpiperidin-4-yl)amino)-3-(2,2,2-trifluoroethyl)indolizin-2-yl)prop-2-yn-1-yl)amino)-6-(methoxy-$d_3$)picolinamide Under argon atmosphere, a mixture of 5-((3-(8-bromo-3-(2,2,2-trifluoroethyl)indolizin-2-yl)prop-2-yn-1-yl)amino)-N-(cyclopropylsulfonyl)-6-(methoxy-$d_3$)picolinamide Cpd-4-3 (560 mg, 950 μmol), (3S,4R)-3-fluoro-1-methylpiperidin-4-amine (252 mg, 1.90 mmol), BrettPhos Pd G3 (86.3 mg, 100 μmol), and cesium carbonate (620 mg, 1.90 mmol) in THF (13 mL) and NMP (1.3 mL) was stirred at 100° C. for 5 hours in a sealed tube. LCMS detection showed that the starting material was completely consumed and the desired compound was detected. The reaction mixture was diluted with water (50 mL) and extracted with EtOAc (20 mL×3). The organic layers were combined and washed with water (40 mL) and saturated brine (40 mL), dried over anhydrous $Na_2SO_4$, filtered, and concentrated under reduced pressure. The residue was purified by Prep-HPLC to obtain the product N-(cyclopropylsulfonyl)-5-((3-(8-(((3S,4R)-3-fluoro-1-methylpiperidin-4-yl)amino)-3-(2,2,2-trifluoroethyl)indolizin-2-yl)prop-2-yn-1-yl)amino)-6-(methoxy-$d_3$)picolinamide Cpd-4 (42.4 mg, 6.80% yield, yellow solid). LCMS calculated for $C_{29}H_{30}D_3F_4N_6O_4S$ $[M+H]^+$: m/z=640.2; found: 640.1; $^1H$ NMR (400 MHZ, DMSO-$d_6$) δ 10.88 (s, 1H), 7.68 (d, J=8.0 Hz, 1H), 7.58 (d, J=7.2 Hz, 1H), 7.08 (d, J=8.0 Hz, 1H), 6.92 (s, 1H), 6.76 (t, J=6.0 Hz, 1H), 6.51 (t, J=7.2 Hz, 1H), 5.86 (d, J=7.2 Hz, 1H), 5.55 (d, J=8.0 Hz, 1H), 4.83 (d, J=49.2 Hz, 1H), 4.28 (d, J=6.0 Hz, 2H), 3.99-3.91 (m, 2H), 3.62-3.49 (m, 1H), 3.13-3.01 (m, 2H), 2.84-2.82 (m, 1H), 2.33-2.21 (m, 1H), 2.23 (s, 3H), 2.15-2.10 (m, 1H), 2.03-1.93 (m, 1H), 1.71-1.67 (m, 1H), 1.19-1.15 (m, 2H), 1.09-1.04 (m, 2H).

Example 5: N-((Cyclopropylmethyl)sulfonyl)-5-((3-(8-(((3S,4R)-3-fluoro-1-methylpiperidin-4-yl)amino)-3-(2,2,2-trifluoroethyl)indolizin-2-yl)prop-2-yn-1-yl)amino)-6-(methoxy-$d_3$)picolinamide (Cpd-5, i.e., Compound 5)
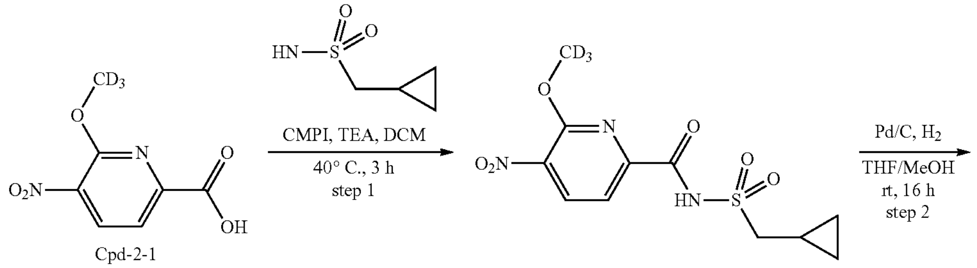
Cpd-2-1
Cpd-5-1
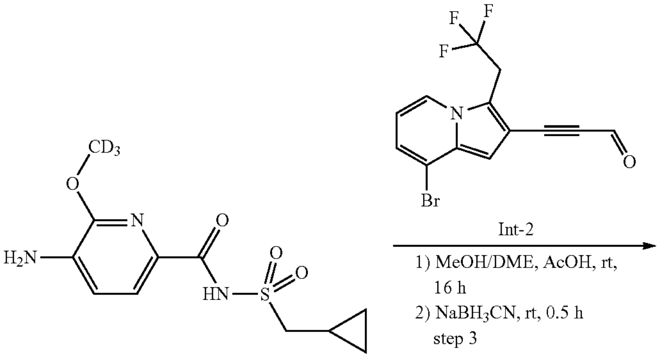
Cpd-5-2
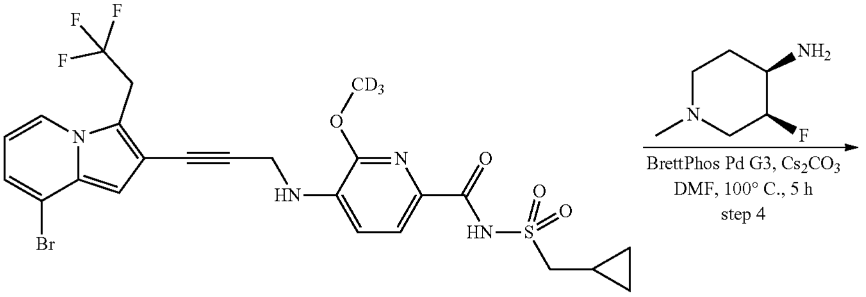
Cpd-5-3
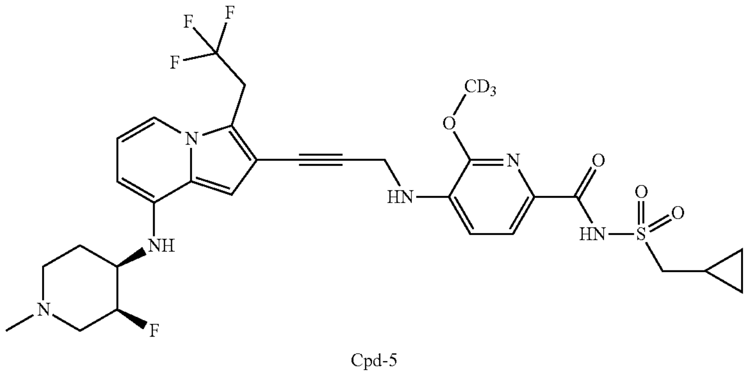
Cpd-5

Step 1: N-((Cyclopropylmethyl)sulfonyl)-6-(methoxy-$d_3$)-5-nitropicolinamide

At room temperature, (cyclopropylmethyl)sulfonamide (1.69 g, 12.5 mmol) and triethylamine (3.62 g, 35.8 mmol) were sequentially added to a mixture of 6-(methoxy-$d_3$)-5-nitropicolinic acid Cpd-2-1 (2.40 g, 11.9 mmol) and 2-chloro-1-methylpyridinium iodide (3.35 g, 13.1 mmol) in DCM (80 mL). The reaction mixture was stirred at 40° C. for 3 hours. LCMS detection showed that the starting material was completely consumed and the desired compound was detected. The reaction mixture was concentrated under reduced pressure, and the residue was diluted with water (100 mL), adjusted to pH=2 with 1N HCl aqueous solution, and extracted with DCM (100 mL×3). The organic layers were combined, washed with water (50 mL) and saturated brine (50 mL), dried over anhydrous $Na_2SO_4$, filtered, and concentrated under reduced pressure. The residue was purified by SGC (0 to 5% MeOH added to DCM) to obtain N-((cyclopropylmethyl)sulfonyl)-6-(methoxy-$d_3$)-5-nitropicolinamide Cpd-5-1 (1.10 g, 29.0% yield, white solid). LCMS calculated for $C_{11}H_9D_3N_3O_6S$ $[M-H]^-$: m/z=317.1; found: 316.9.

Step 2: 5-Amino-N-((cyclopropylmethyl)sulfonyl)-6-(methoxy-$d_3$)picolinamide

At room temperature, a mixture of N-((cyclopropylmethyl)sulfonyl)-6-(methoxy-$d_3$)-5-nitropicolinamide Cpd-5-1 (1.10 g, 3.46 mmol) and palladium on carbon (550 mg, 10% content) in THF (20 mL) and MeOH (30 mL) was stirred for 16 hours under hydrogen atmosphere. LCMS detection showed that the starting material was completely consumed and the desired compound was detected. The reaction mixture was filtered and concentrated under reduced pressure to obtain 5-amino-N-((cyclopropylmethyl)sulfonyl)-6-(methoxy-$d_3$)picolinamide Cpd-5-2 (970 mg, crude product, yellow-white solid). The crude product was used directly in the next step reaction. LCMS calculated for $C_{11}H_{11}D_3N_3O_4S$ $[M-H]^-$: m/z=287.1; found: 287.1.

Step 3: 5-((3-(8-Bromo-3-(2,2,2-trifluoroethyl)indolizin-2-yl)prop-2-yn-1-yl)amino)-N-((cyclopropylmethyl)sulfonyl)-6-(methoxy-$d_3$)picolinamide A mixture of 3-(8-bromo-3-(2,2,2-trifluoroethyl)indolizin-2-yl)propiolaldehyde Int-2 (500 mg, 1.51 mmol), 5-amino-N-((cyclopropylmethyl)sulfonyl)-6-(methoxy-$d_3$)picolinamide Cpd-5-2 (416 mg, 1.44 mmol), acetic acid (86.6 mg, 1.44 mmol), and $Na_2SO_4$ (1.02 g, 7.21 mmol) in MeOH (20 mL) and 1,2-dichloroethane (20 mL) was stirred at room temperature for 16 hours. Then $NaBH_3CN$ (181 mg, 2.89 mmol) was added thereto, and the system was stirred for another 0.5 hours at room temperature. LCMS detection showed that the starting material was completely consumed and the desired compound was detected. The reaction mixture was diluted with water (40 mL) and extracted with DCM (100 mL×3). The organic layers were combined, washed with water (50 mL) and saturated brine (50 mL), dried over anhydrous $Na_2SO_4$, filtered, and concentrated under reduced pressure. The residue was purified by SGC (0 to 70% EtOAc added to PE) method to obtain 5-((3-(8-bromo-3-(2,2,2-trifluoroethyl)indolizin-2-yl)prop-2-yn-1-yl)amino)-N-((cyclopropylmethyl)sulfonyl)-6-(methoxy-$d_3$)picolinamide Cpd-5-3 (390 mg, 44.9% yield, yellow solid). LCMS calculated for $C_{24}H_{20}BrD_3F_3N_4O_4S$ $[M+H]^+$: m/z=602.1/604.1; found: 602.3/604.3.

Step 4: N-((Cyclopropylmethyl)sulfonyl)-5-((3-(8-(((3S,4R)-3-fluoro-1-methylpiperidin-4-yl)amino)-3-(2,2,2-trifluoroethyl)indolizin-2-yl)prop-2-yn-1-yl)amino)-6-(methoxy-$d_3$)picolinamide Under argon atmosphere, a mixture of 5-((3-(8-bromo-3-(2,2,2-trifluoroethyl)indolizin-2-yl)prop-2-yn-1-yl)amino)-N-((cyclopropylmethyl)sulfonyl)-6-(methoxy-$d_3$)picolinamide Cpd-5-3 (390 mg, 650 μmol), (3S,4R)-3-fluoro-1-methylpiperidin-4-amine (171 mg, 1.29 mmol), BrettPhos Pd G3 (58.7 mg, 60.0 μmol), and cesium carbonate (422 mg, 1.29 mmol) in DMF (12 mL) was stirred at 100° C. for 5 hours. LCMS detection showed that the starting material was completely consumed and the desired compound was detected. The reaction mixture was diluted with water (50 mL), adjusted to pH=8 with 1N HCl aqueous solution, and extracted with EtOAc/THF (2:1, 30 mL×3). The organic layers were combined and washed with water (40 mL) and saturated brine (40 mL), dried over anhydrous $Na_2SO_4$, filtered, and concentrated under reduced pressure. The residue was purified by Prep-HPLC to obtain the product N-((cyclopropylmethyl)sulfonyl)-5-((3-(8-(((3S,4R)-3-fluoro-1-methylpiperidin-4-yl)amino)-3-(2,2,2-trifluoroethyl)indolizin-2-yl)prop-2-yn-1-yl)amino)-6-(methoxy-$d_3$)picolinamide Cpd-5 (81.2 mg, 19.1% yield, white solid). LCMS calculated for $C_{30}H_{32}D_3F_4N_6O_4S$ $[M+H]^+$: m/z=654.3; found: 654.7; $^1H$ NMR (400 MHZ, DMSO-$d_6$) δ 10.86 (s, 1H), 7.66 (d, J=8.0 Hz, 1H), 7.58 (d, J=7.2 Hz, 1H), 7.07 (d, J=8.0 Hz, 1H), 6.92 (s, 1H), 6.77 (t, J=6.0 Hz, 1H), 6.51 (t, J=7.2 Hz, 1H), 5.86 (d, J=7.2 Hz, 1H), 5.55 (d, J=8.0 Hz, 1H), 4.83 (d, J=49.2 Hz, 1H), 4.28 (d, J=6.0 Hz, 2H), 3.98-3.90 (m, 2H), 3.62-3.48 (m, 1H), 3.43 (d, J=7.2 Hz, 2H), 3.08-3.03 (m, 1H), 2.86-2.82 (m, 1H), 2.33-2.21 (m, 1H), 2.23 (s, 3H), 2.15-2.09 (m, 1H), 2.03-1.93 (m, 1H), 1.72-1.66 (m, 1H), 1.09-1.00 (m, 1H), 0.59-0.54 (m, 2H), 0.34-0.30 (m, 2H).

Example 6: 5-((3-(8-(((3S,4R)-3-Fluoro-1-methylpiperidin-4-yl)amino)-3-(2,2,2-trifluoroethyl)indolizin-2-yl)prop-2-yn-1-yl)amino)-6-(methoxy-$d_3$)-N-((2,2,2-trifluoroethyl)sulfonyl)picolinamide (Cpd-6, i.e., Compound 6)

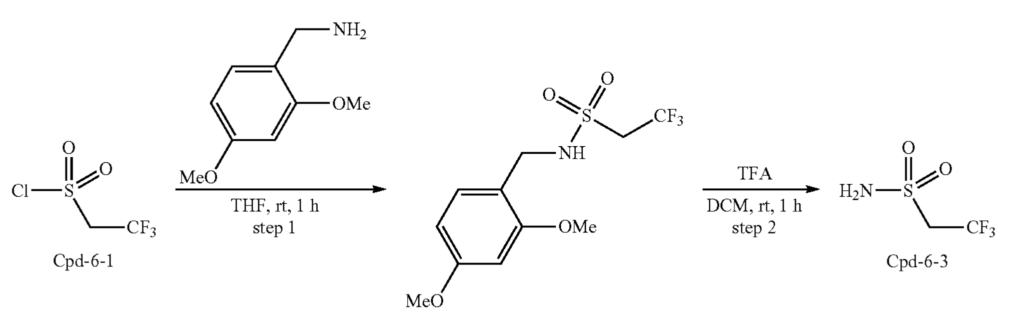

Cpd-6-1 Cpd-6-2 Cpd-6-3

-continued
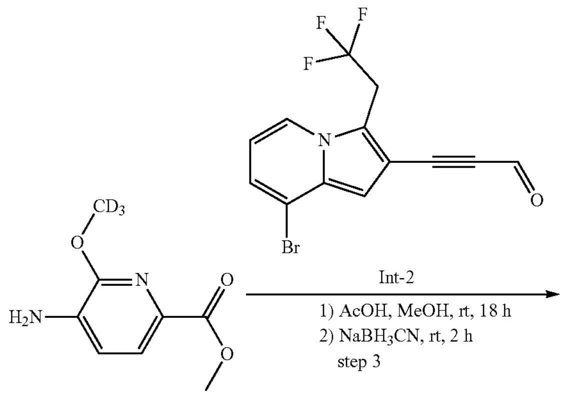
Cpd-2-3
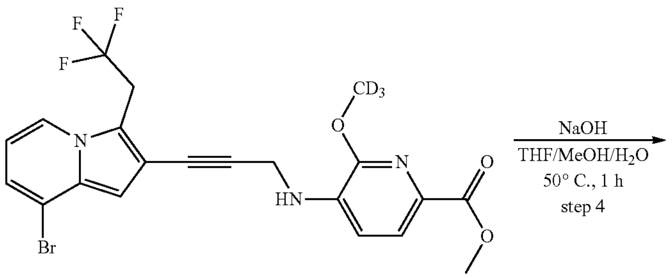
Cpd-6-4
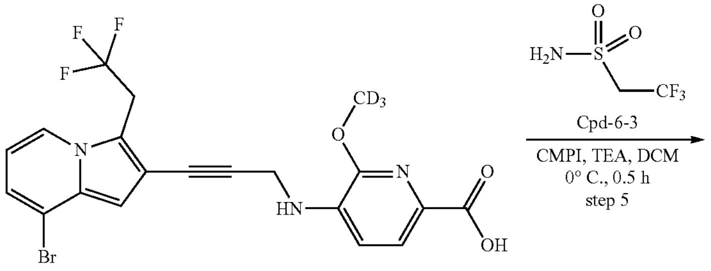
Cpd-6-5
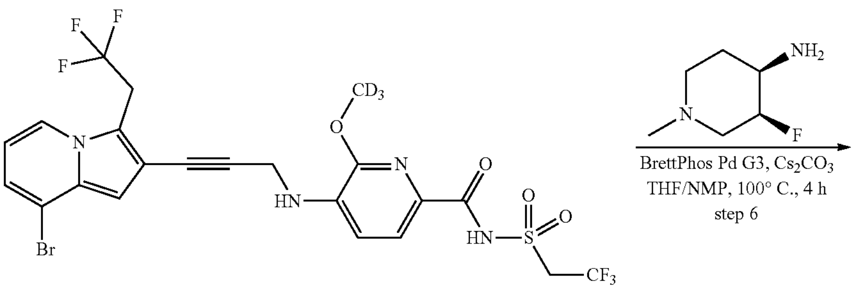
Cpd-6-6

-continued

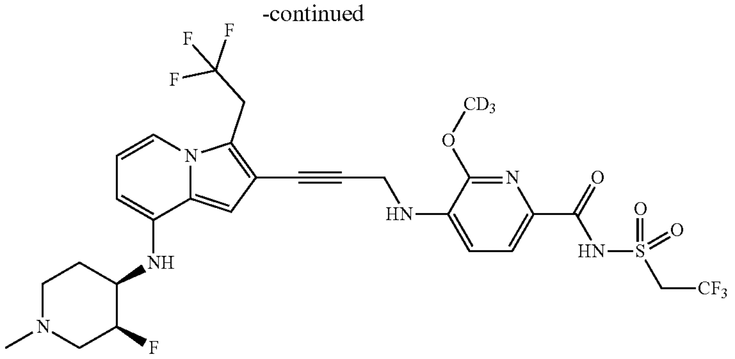

Cpd-6

Step 1: N-(2,4-Dimethoxybenzyl)-2,2,2-trifluoroethane-1-sulfonamide

At room temperature, 2,2,2-trifluoroethane-1-sulfonyl chloride Cpd-6-1 (750 mg, 4.11 mmol) was added dropwise to a solution of 2,4-dimethoxybenzylamine (1.37 g, 8.22 mmol) in THF (20 mL), and the system was stirred for 1 hour. LCMS detection showed that the starting material was completely consumed and the desired compound was detected. The reaction mixture was concentrated under reduced pressure, and the resulting residue was purified by SGC (0 to 1% MeOH added to DCM) method to obtain N-(2,4-dimethoxybenzyl)-2,2,2-trifluoroethane-1-sulfonamide Cpd-6-2 (1.20 g, 93.2% yield, white solid). LCMS calculated for $C_{11}H_{14}F_3NNaO_4S$ $[M+Na]^+$: m/z=336.1; found: 336.1.

Step 2: 2,2,2-Trifluoroethane-1-sulfonamide

N-(2,4-Dimethoxybenzyl)-2,2,2-trifluoroethane-1-sulfonamide Cpd-6-2 (1.45 g, 4.63 mmol) was dissolved in DCM (15 mL), and trifluoroacetic acid (15 mL) was slowly added thereto, and then the system was stirred for 1 hour at room temperature. LCMS detection showed that the starting material was completely consumed and the desired compound was detected. The reaction mixture was concentrated under reduced pressure to obtain 2,2,2-trifluoroethane-1-sulfonamide Cpd-6-3 (851 mg, 99.1% yield, purple solid). The crude product was used directly in the next step reaction. 1H NMR (400 MHZ, DMSO-$d_6$) δ 7.50 (s, 2H), 4.26 (q, J=10.0 Hz, 2H).

Step 3: Methyl 5-((3-(8-bromo-3-(2,2,2-trifluoroethyl)indolizin-2-yl)prop-2-yn-1-yl)amino)-6-(methoxy-$d_3$)picolinate A mixture of 3-(8-bromo-3-(2,2,2-trifluoroethyl)indolizin-2-yl)propiolaldehyde Int-2 (700 mg, 2.33 mmol), methyl 5-amino-6-(methoxy-$d_3$)picolinate Cpd-2-3 (432 mg, 2.33 mmol), and acetic acid (280 mg, 4.67 mmol) in MeOH (20 mL) was stirred at room temperature for 16 hours. Then $NaBH_3CN$ (440 mg, 7.00 mmol) was added thereto, and the system was stirred for another 2 hours at room temperature. LCMS detection showed that the starting material was completely consumed and the desired compound was detected. The reaction mixture was diluted with water (40 mL) and extracted with DCM (100 mL×3). The organic layers were combined, washed with water (50 mL) and saturated brine (50 mL), dried over anhydrous $Na_2SO_4$, filtered, and concentrated under reduced pressure. The residue was purified by SGC (0 to 70% EtOAc added to PE) method to obtain methyl 5-((3-(8-bromo-3-(2,2,2-trifluoroethyl)indolizin-2-yl)prop-2-yn-1-yl)amino)-6-(methoxy-$d_3$) picolinate Cpd-6-4 (625 mg, 53.7% yield, yellow solid). LCMS calculated for $C_{21}H_{15}D_3BrF_3N_3O_3$ $[M+H]^+$: m/z=499.1/501.1; found: 499.0/501.0.

Step 4: 5-((3-(8-Bromo-3-(2,2,2-trifluoroethyl)indolizin-2-yl)prop-2-yn-1-yl)amino)-6-(methoxy-$d_3$) picolinic acid Methyl 5-((3-(8-bromo-3-(2,2,2-trifluoroethyl)indolizin-2-yl)prop-2-yn-1-yl)amino)-6-(methoxy-$d_3$)picolinate Cpd-6-4 (300 mg, 600 μmol) and sodium hydroxide (72.1 mg, 1.80 mmol) were dissolved in a mixed solvent of THF (9 mL), MeOH (6 mL), and water (1 mL), and the system was stirred at 50° C. for 1 hour. LCMS detection showed that the starting material was completely consumed and the desired compound was detected. The reaction mixture was concentrated under reduced pressure, diluted with water (20 mL), and adjusted to pH=5 with 1N HCl. The solid was collected by filtration and dried to obtain 5-((3-(8-bromo-3-(2,2,2-trifluoroethyl)indolizin-2-yl)prop-2-yn-1-yl)amino)-6-(methoxy-$d_3$)picolinic acid Cpd-6-5 (246 mg, 84.4% yield, white solid). LCMS calculated for $C_{20}H_{13}D_3BrF_3N_3O_3$ $[M+H]^+$: m/z=485.1/487.1; found: 485.0/487.0.

Step 5: 5-((3-(8-Bromo-3-(2,2,2-trifluoroethyl)indolizin-2-yl)prop-2-yn-1-yl)amino)-6-(methoxy-$d_3$)-N-((2,2,2-trifluoroethyl)sulfonyl)picolinamide Tricthylamine (0.21 mL, 1.48 mmol) was added to a mixture of 5-((3-(8-bromo-3-(2,2,2-trifluoroethyl)indolizin-2-yl)prop-2-yn-1-yl)amino)-6-(methoxy-$d_3$)picolinic acid Cpd-6-5 (240 mg, 490 μmol), 2,2,2-trifluoroethane-1-sulfonamide Cpd-6-3 (242 mg, 1.48 mmol), and 2-chloro-1-methylpyridinium iodide (316 mg, 1.24 mmol) in DCM (40 mL) at 0° C. The reaction mixture was stirred at 0° C. for 30 minutes. LCMS detection showed that the starting material was completely consumed and the desired compound was detected. The reaction mixture was diluted with DCM (100 mL) and washed sequentially with 0.5N HCl aqueous solution (50 mL), saturated sodium bicarbonate aqueous solution (50 mL), and saturated brine (50 mL), dried over anhydrous $Na_2SO_4$, filtered, and concentrated under reduced pressure. The residue was purified by SGC (0 to 8% MeOH added to DCM) method to obtain 5-((3-(8-bromo-3-(2,2,2-trifluoroethyl)indolizin-2-yl)prop-2-yn-1-yl)amino)-6-(methoxy- $d_3$)-N-((2,2,2-trifluoroethyl)sulfonyl)picolinamide Cpd-6-6 (160 mg, 51.3% yield, white solid). LCMS calculated for $C_{22}H_{15}D_3BrF_6N_4O_4S$ [M+H]$^+$: m/z=630.0/632.0; found: 629.9/631.9.

Step 6: 5-((3-(8-(((3S,4R)-3-Fluoro-1-methylpiperidin-4-yl)amino)-3-(2,2,2-trifluoroethyl)indolizin-2-yl)prop-2-yn-1-yl)amino)-6-(methoxy-$d_3$)-N-((2,2,2-trifluoroethyl)sulfonyl)picolinamide Under argon atmosphere, a mixture of 5-((3-(8-bromo-3-(2,2,2-trifluoroethyl)indolizin-2-yl)prop-2-yn-1-yl)amino)-6-(methoxy-$d_3$)-N-((2,2,2-trifluoroethyl)sulfonyl)picolinamide Cpd-6-6 (160 mg, 250 μmol), (3S,4R)-3-fluoro-1-methylpiperidin-4-amine (67.0 mg, 510 μmol), BrettPhos Pd G3 (23.0 mg, 30.0 μmol), and cesium carbonate (165 mg, 510 μmol) in THF (13 mL) and NMP (1.3 mL) was stirred at 100° C. for 4 hours in a sealed tube. LCMS detection showed that the starting material was completely consumed and the desired compound was detected. The reaction mixture was diluted with water (50 mL) and extracted with EtOAc (20 mL×3). The organic layers were combined and washed with water (40 mL) and brine (40 mL), dried over anhydrous $Na_2SO_4$, filtered, and concentrated under reduced pressure. The residue was purified by SGC (0 to 8% MeOH added to DCM) to obtain the product 5-((3-(8-(((3S,4R)-3-fluoro-1-methylpiperidin-4-yl)amino)-3-(2,2,2-trifluoroethyl)indolizin-2-yl)prop-2-yn-1-yl)amino)-6-(methoxy-$d_3$)-N-((2,2,2-trifluoroethyl)sulfonyl)picolinamide Cpd-6 (14.0 mg, 8.09% yield, white solid). LCMS calculated for $C_{28}H_{27}D_3F_7N_6O_4S$ [M+H]$^+$: m/z=682.2; found: 682.5; $^1$H NMR (400 MHZ, DMSO-$d_6$) δ 10.53 (s, 1H), 7.64 (dd, J=16.0, 6.9 Hz, 2H), 7.01 (d, J=7.5 Hz, 1H), 6.93 (s, 1H), 6.53 (t, J=6.4 Hz, 1H), 6.50-6.33 (m, 1H), 5.90 (d, J=7.1 Hz, 1H), 5.81 (d, J=6.4 Hz, 1H), 5.09 (d, J=47.1 Hz, 1H), 4.70-4.33 (m, 2H), 4.26 (d, J=4.2 Hz, 2H), 3.97 (d, J=10.4 Hz, 2H), 3.89-3.76 (m, 1H), 2.73 (s, 3H), 2.49-2.45 (m, 2H), 2.26-2.16 (m, 1H), 1.97-1.88 (m, 1H).

Example 7: N-(Cyclopropylsulfonyl)-5-((3-(8-(((3S,4R)-3-fluoro-1-methylpiperidin-4-yl)amino)-3-(2,2,2-trifluoroethyl)indolizin-2-yl)prop-2-yn-1-yl)amino)-6-methoxypicolinamide (Cpd-7, i.e., Compound 7)

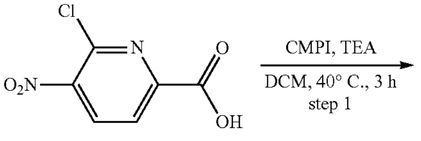

Cpd-1-1

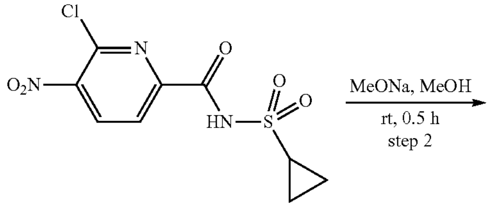

Cpd-7-1

-continued

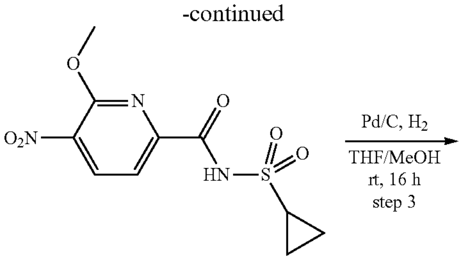

Cpd-7-2

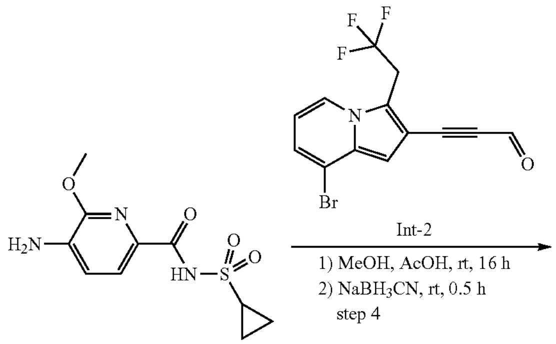

Cpd-7-3

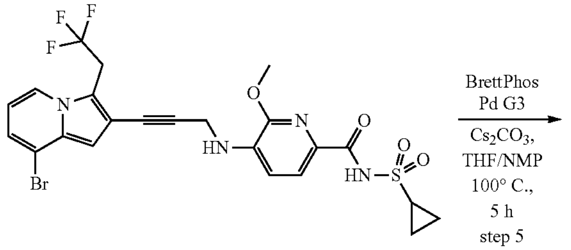

Cpd-7-4

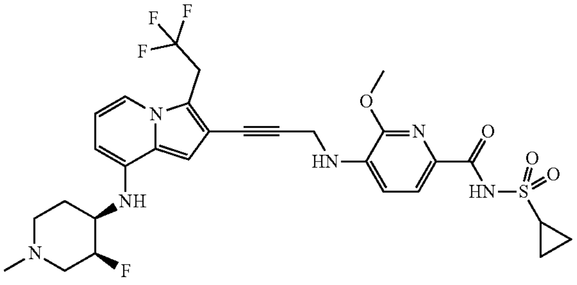

Cpd-7

Step 1: 6-Chloro-N-(cyclopropylsulfonyl)-5-nitropicolinamide

At room temperature, cyclopropylsulfonamide (3.59 g, 29.6 mmol) and triethylamine (7.49 g, 74.1 mmol) were sequentially added to a mixture of 6-chloro-5-nitropicolinic acid Cpd-1-1 (5.00 g, 24.7 mmol) and 2-chloro-1-methylpyridinium iodide (7.57 g, 29.6 mmol) in DCM (50 mL). The reaction system was stirred at 40° C. for 3 hours. LCMS detection showed that the starting material was completely consumed and the desired compound was detected. The reaction mixture was concentrated under reduced pressure, and the residue was diluted with water (100 mL). The pH was adjusted to 2 with 1N HCl aqueous solution. The precipitated solid was filtered, washed with water, and dried to obtain 6-chloro-N-(cyclopropylsulfonyl)-5-nitropicolinamide Cpd-7-1 (8.90 g, crude product, white solid). The crude product was used directly in the next step reaction. LCMS calculated for $C_9H_7ClN_3O_5S$ [M−H]=: m/z=304.0/306.0; found: 303.9/305.9.

Step 2: N-(Cyclopropylsulfonyl)-6-methoxy-5-nitropicolinamide

At room temperature, a solution of sodium methoxide (16.2 mL, 87.3 mmol, 5.4 mol/L) in methanol was added dropwise to a solution of 6-chloro-N-(cyclopropylsulfonyl)-5-nitropicolinamide Cpd-7-1 (8.90 g, 29.1 mmol) in methanol (90 mL). The reaction mixture was stirred at room temperature for 30 minutes. LCMS detection showed that the starting material was completely consumed and the desired compound was detected. The reaction mixture was quenched with 1N HCl aqueous solution, and the pH was adjusted to 2. The precipitated solid was filtered, washed with water, and dried to obtain N-(cyclopropylsulfonyl)-6-methoxy-5-nitropicolinamide Cpd-7-2 (6.70 g, crude product, white solid). The crude product was used directly in the next step reaction. LCMS calculated for $C_{10}H_{10}N_3O_6S$ $[M-H]^-$: m/z=300.0; found: 300.0.

Step 3: 5-Amino-N-(cyclopropylsulfonyl)-6-methoxypicolinamide

At room temperature, a mixture of N-(cyclopropylsulfonyl)-6-methoxy-5-nitropicolinamide Cpd-7-2 (6.70 g, 22.2 mmol) and palladium on carbon (3.30 g, 5% content) in THF (200 mL) and MeOH (130 mL) was stirred for 16 hours at room temperature under hydrogen atmosphere. LCMS detection showed that the starting material was completely consumed and the desired compound was detected. The reaction mixture was filtered and concentrated under reduced pressure to obtain 5-amino-N-(cyclopropylsulfonyl)-6-methoxypicolinamide Cpd-7-3 (6.20 g, crude product, white solid). The crude product was used directly in the next step reaction. LCMS calculated for $C_{10}H_{12}N_3O_4S$ $[M-H]^-$: m/z=270.1; found: 270.1.

Step 4: 5-((3-(8-Bromo-3-(2,2,2-trifluoroethyl)indolizin-2-yl)prop-2-yn-1-yl)amino)-N-(cyclopropylsulfonyl)-6-methoxypicolinamide A mixture of 3-(8-bromo-3-(2,2,2-trifluoroethyl)indolizin-2-yl)propiolaldehyde Int-2 (1.00 g, 3.03 mmol), 5-amino-N-(cyclopropylsulfonyl)-6-methoxypicolinamide Cpd-7-3 (820 mg, 3.03 mmol), and acetic acid (180 mg, 3.03 mmol) in MeOH (15 mL) was stirred at room temperature for 16 hours. Then $NaBH_3CN$ (570 mg, 9.09 mmol) was added thereto, and the system was stirred for another 2 hours at room temperature. LCMS detection showed that the starting material was completely consumed and the desired compound was detected. The reaction mixture was quenched with saturated sodium bicarbonate aqueous solution (50 mL) and extracted with EtOAc (20 mL×3). The organic layers were combined and washed with water (40 mL) and saturated brine (40 mL), dried over anhydrous $Na_2SO_4$, filtered, and concentrated under reduced pressure. The residue was purified by slurrying with dichloromethane to obtain 5-((3-(8-bromo-3-(2,2,2-trifluoroethyl)indolizin-2-yl)prop-2-yn-1-yl)amino)-N-(cyclopropylsulfonyl)-6-methoxypicolinamide Cpd-7-4 (500 mg, 28.2% yield, yellow solid). LCMS calculated for $C_{23}H_{21}BrF_3N_4O_4S$ $[M+H]^+$: m/z=585.0/587.0; found: 585.3/587.3.

Step 5: N-(Cyclopropylsulfonyl)-5-((3-(8-(((3S,4R)-3-fluoro-1-methylpiperidin-4-yl)amino)-3-(2,2,2-trifluoroethyl)indolizin-2-yl)prop-2-yn-1-yl)amino)-6-methoxypicolinamide Under argon atmosphere, a mixture of 5-((3-(8-bromo-3-(2,2,2-trifluoroethyl)indolizin-2-yl)prop-2-yn-1-yl)amino)-N-(cyclopropylsulfonyl)-6-methoxypicolinamide Cpd-7-4 (500 mg, 850 μmol), (3S,4R)-3-fluoro-1-methylpiperidin-4-amine (226 mg, 1.71 mmol), BrettPhos Pd G3 (77.4 mg, 10.0 μmol), and cesium carbonate (557 mg, 1.71 mmol) in THF (15 mL) and NMP (1.5 mL) was stirred at 100° C. for 5 hours in a sealed tube. LCMS detection showed that the starting material was completely consumed and the desired compound was detected. The reaction mixture was diluted with water (50 mL) and extracted with EtOAc (20 mL×3). The organic layers were combined and washed with water (40 mL) and saturated brine (40 mL), dried over anhydrous $Na_2SO_4$, filtered, and concentrated under reduced pressure. The residue was purified by Prep-HPLC to obtain the product N-(cyclopropylsulfonyl)-5-((3-(8-(((3S,4R)-3-fluoro-1-methylpiperidin-4-yl)amino)-3-(2,2,2-trifluoroethyl)indolizin-2-yl)prop-2-yn-1-yl)amino)-6-methoxypicolinamide Cpd-7 (46.1 mg, 8.3% yield, yellow solid). LCMS calculated for $C_{29}H_{33}F_4N_6O_4S$ $[M+H]^+$: m/z=637.2; found: 637.1; $^1H$ NMR (400 MHZ, DMSO-$d_6$) δ 10.83 (s, 1H), 7.68 (d, J=6.8 Hz, 1H), 7.58 (d, J=6.8 Hz, 1H), 7.08 (d, J=8.4 Hz, 1H), 6.92 (s, 1H), 6.76 (t, J=6.0 Hz, 1H), 6.51 (t, J=7.2 Hz, 1H), 5.86 (d, J=7.6 Hz, 1H), 5.55 (d, J=8.4 Hz, 1H), 4.83 (d, J=48.6 Hz, 1H), 4.28 (d, J=6.4 Hz, 2H), 4.06 (s, 3H), 4.00-3.91 (m, 2H), 3.62-3.49 (m, 1H), 3.11-3.03 (m, 2H), 2.84-2.82 (m, 1H), 2.33-2.21 (m, 1H), 2.23 (s, 3H), 2.15-2.09 (m, 1H), 2.03-1.93 (m, 1H), 1.71-1.67 (m, 1H), 1.19-1.15 (m, 2H), 1.10-1.04 (m, 2H).

Example 8: 5-((3-(8-(((3R,4S)-3-Fluoro-1-methylpiperidin-4-yl)amino)-3-(2,2,2-trifluoroethyl)indolizin-2-yl)prop-2-yn-1-yl)amino)-6-(methoxy-$d_3$)-N-(methylsulfonyl)picolinamide (Cpd-8, i.e., Compound 8)

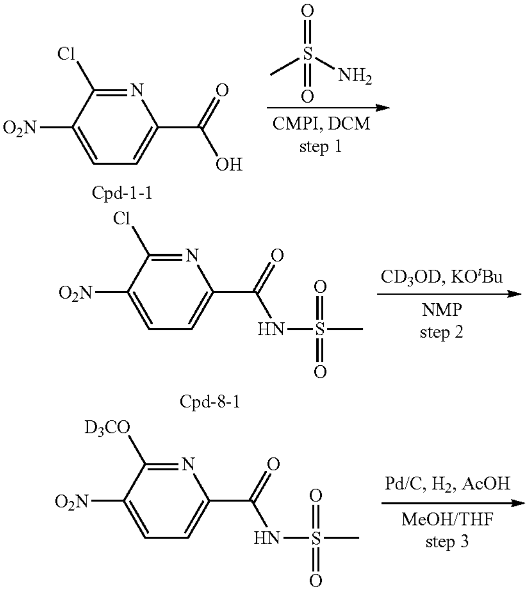

Cpd-1-1

Cpd-8-1

Cpd-8-2

-continued

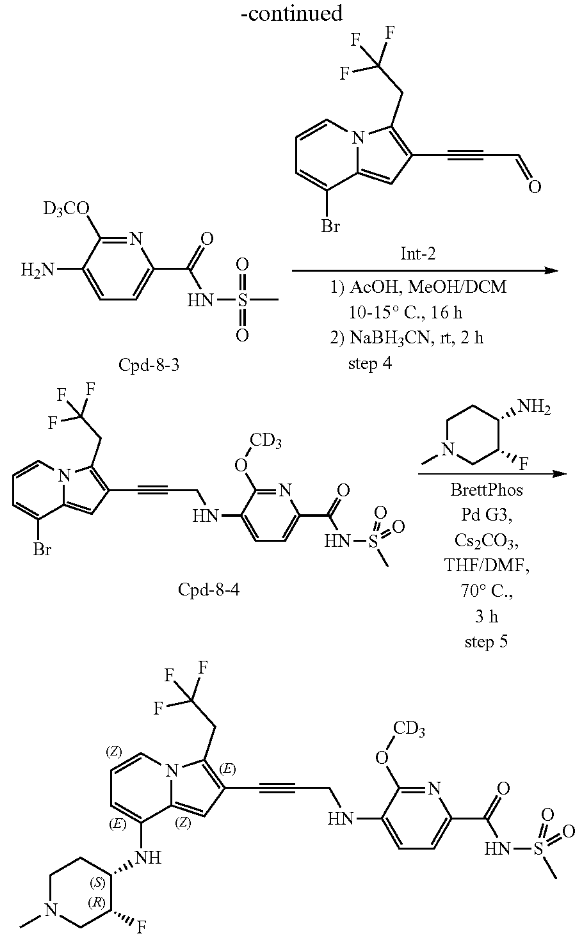

Cpd-8-3

Cpd-8-4

Cpd-8

Step 1: 6-Chloro-N-(methylsulfonyl)-5-nitropicolinamide

2-Chloro-1-methylpyridinium iodide (95.0 g, 372 mmol) and methanesulfonamide (35.0 g, 368 mmol) were added to a suspension of 6-chloro-5-nitropicolinic acid Cpd-1-1 (50.0 g, 247 mmol) in dichloromethane (500 mL) with stirring. After the system was stirred for 10 minutes, triethylamine (100 g, 988 mmol) was added dropwise thereto. Then the reaction mixture was heated to reflux and reacted for about 5 hours. After being cooled and concentrated, the residue was diluted with water (250 mL) and adjusted to pH=2 with concentrated HCl. A large amount of yellow solid precipitated. The mixture was stirred at room temperature overnight, subjected to suction filtration, and the filter cake was rinsed with water (250 mL). The filter cake was dried at 50° C. under vacuum to obtain 6-chloro-N-(methylsulfonyl)-5-nitropicolinamide Cpd-8-1 (68.0 g, 98.5% yield, yellow solid). LCMS calculated for $C_7H_5ClN_3O_5S$ $[M-H]^-$: m/z=278.0; found: 278.1.

Step 2: 6-(Methoxy-$d_3$)-N-(methylsulfonyl)-5-nitropicolinamide

Under argon atmosphere, 6-chloro-N-(methylsulfonyl)-5-nitropicolinamide Cpd-8-1 (45.0 g, 161 mmol) and deuterated methanol (17.4 g, 482 mmol) were dissolved in anhydrous NMP (450 mL), then the system was cooled to −15° C. to 0° C., and a solution of 1M potassium tert-butoxide in tetrahydrofuran (338 mL, 338 mmol) was added dropwise thereto. Then the system temperature was controlled at −10° C. to 0° C., and the reaction was stirred for 40 minutes, then 4N HCl (135 mL) was added dropwise to quench the reaction. The system was concentrated under reduced pressure, and water (1.62 L) was added dropwise thereto with stirring. A large amount of yellow solid was produced and filtered. The filter cake was rinsed with water (500 mL) and methyl tert-butyl ether (500 mL), and the filter cake was recrystallized with acetonitrile-water to obtain the product 6-(methoxy-$d_3$)-N-(methylsulfonyl)-5-nitropicolinamide Cpd-8-2 (30.0 g, 67.0% yield, yellow solid). LCMS calculated for $C_8H_7D_3N_3O_6S$ $[M+H]^+$: m/z=279.0; found: 279.2.

Step 3: 5-Amino-6-(methoxy-$d_3$)-N-(methylsulfonyl)picolinamide 6-(Methoxy-$d_3$)-N-(methylsulfonyl)-5-nitropicolinamide Cpd-8-2 (30.0 g, 108 mmol) was mixed with THF (600 mL) and acetic acid (3.24 g, 53.9 mmol), and stirred to form a solution, then methanol (600 mL) was added thereto. After argon replacement, palladium on carbon (3.00 g, 10% content) was added thereto, and argon was replaced with hydrogen, and then the reaction was stirred at room temperature for 12 hours. The reaction mixture was filtered through diatomite, and the filter cake was rinsed with THF. The filtrate was combined and concentrated. The residue was dried to obtain the product 5-amino-6-(methoxy-$d_3$)-N-(methylsulfonyl)picolinamide Cpd-8-3 (26.0 g, 97.1% yield, off-white solid), which was directly used in the next step without further treatment. LCMS calculated for $C_8H_9D_3N_3O_4S$ $[M+H]^+$: m/z=249.1; found: 249.2.

Step 4: 8-Bromo-2-(3-((2-(methoxy-$d_3$)-6-((methylsulfonyl)carbamoyl)pyridin-3-yl)amino)prop-1-yn-1-yl)-3-(2,2,2-trifluoroethyl)indolizine A mixed solvent of methanol (100 mL) and dichloromethane (100 mL) was added to 5-amino-6-(methoxy-$d_3$)-N-(methylsulfonyl)picolinamide Cpd-8-3 (7.20 g, 29.0 mmol) and acetic acid (3.14 g, 58.0 mmol). When the mixture became clear, Int-2 (10.1 g, 30.5 mmol) was added thereto. The system was stirred at 10° C. to 15° C. for 16 hours. A large amount of turbidity was produced in the system, and then sodium cyanoborohydride (6.00 g, 87.1 mmol) was added thereto, and the system was stirred for another 2 hours. The system was concentrated, added with methanol (100 mL), added dropwise with water (100 mL) at room temperature, then stirred at room temperature for 2 hours, and filtered. The filter cake was rinsed with water (50 mL) and methyl tert-butyl ether (100 mL), and dried under vacuum with an oil pump to obtain 8-bromo-2-(3-((2-(methoxy-$d_3$)-6-((methylsulfonyl)carbamoyl)pyridin-3-yl)amino)prop-1-yn-1-yl)-3-(2,2,2-trifluoroethyl)indolizine Cpd-8-4 (12.9 g, 79.0% yield, off-white solid). LCMS calculated for $C_{21}H_{16}D_3BrF_3N_4O_4S$ $[M+H]^+$: m/z=562.0/564.0; found: 562.2/564.2.

Step 5: 5-((3-(8-(((3R,4S)-3-Fluoro-1-methylpiperidin-4-yl)amino)-3-(2,2,2-trifluoroethyl)indolizin-2-yl)prop-2-yn-1-yl)amino)-6-(methoxy-$d_3$)-N-(methylsulfonyl)picolinamide Under argon atmosphere, a mixture of 8-bromo-2-(3-((2-(methoxy-$d_3$)-6-((methylsulfonyl)carbamoyl)pyridin-3-yl)

amino)prop-1-yn-1-yl)-3-(2,2,2-trifluoroethyl)indolizine Cpd-8-4 (1.80 g, 3.20 mmol), (3R,4S)-3-fluoro-1-methylpiperidin-4-amine (500 mg, 3.80 mmol), BrettPhos Pd G3 (600 mg, 662 μmol), and cesium carbonate (3.44 g, 10.6 mmol) in THF (20 mL) and DMF (10 mL) was stirred at 70° C. for 3 hours. The system was cooled and concentrated, and the residue was purified by silica gel column chromatography (MeOH:DCM=1:24) to obtain the product 5-((3-(8-(((3R,4S)-3-fluoro-1-methylpiperidin-4-yl)amino)-3-(2,2,2-trifluoroethyl)indolizin-2-yl)prop-2-yn-1-yl)amino)-6-(methoxy-$d_3$)-N-(methylsulfonyl)picolinamide Cpd-8 (830 mg, 42.3% yield, off-white solid). LCMS calculated for $C_{27}H_{28}D_3F_4N_6O_4S$ $[M+H]^+$: m/z=614.2; found: 614.4; $^1H$ NMR (400 MHZ, DMSO-$d_6$) d 10.83 (s, 1H), 7.67 (d, J=8.0 Hz, 1H), 7.58 (d, J=6.9 Hz, 1H), 7.07 (d, J=8.1 Hz, 1H), 6.92 (s, 1H), 6.75 (t, J=6.1 Hz, 1H), 6.52 (t, J=7.1 Hz, 1H), 5.86 (d, J=7.5 Hz, 1H), 5.56 (d, J=8.4 Hz, 1H), 4.84 (d, J=49.3 Hz, 1H), 4.28 (d, J=6.1 Hz, 2H), 3.95 (q, J=10.8 Hz, 2H), 3.56 (d, J=28.9 Hz, 1H), 3.07 (t, J=11.2 Hz, 1H), 2.85 (d, J=11.1 Hz, 1H), 2.40-2.09 (m, 5H), 2.05-1.91 (m, 1H), 1.69 (dd, J=13.2, 4.0 Hz, 1H).

Example 9: 5-((3-(8-(((3S,4S)-3-Fluoro-1-methylpiperidin-4-yl)amino)-3-(2,2,2-trifluoroethyl)indolizin-2-yl)prop-2-yn-1-yl)amino)-6-(methoxy-$d_3$)-N-(methylsulfonyl)picolinamide (Cpd-9, i.e., Compound 9)

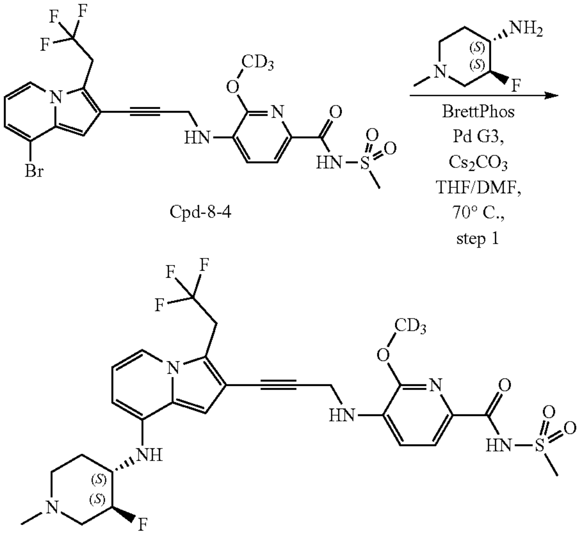

Cpd-8-4

Cpd-9

Step 1: 5-((3-(8-(((3S,4S)-3-Fluoro-1-methylpiperidin-4-yl)amino)-3-(2,2,2-trifluoroethyl)indolizin-2-yl)prop-2-yn-1-yl)amino)-6-(methoxy-$d_3$)-N-(methylsulfonyl)picolinamide Under argon atmosphere, a mixture of 5-((3-(8-bromo-3-(2,2,2-trifluoroethyl)indolizin-2-yl)prop-2-yn-1-yl)amino)-N-(methylsulfonyl)-6-(methoxy-$d_3$)picolinamide Cpd-8-4 (1.80 g, 3.20 mmol), (3S,4S)-3-fluoro-1-methylpiperidin-4-amine (400 mg, 3.02 mmol), BrettPhos Pd G3 (600 mg, 662 μmol), and cesium carbonate (3.44 g, 10.6 mmol) in THF (20 mL) and DMF (10 mL) was stirred at 70° C. for 3 hours. The system was cooled and concentrated, and the residue was purified by silica gel column chromatography (MeOH:DCM=1:24) to obtain the product 5-((3-(8-(((3S,4S)-3-fluoro-1-methylpiperidin-4-yl)amino)-3-(2,2,2-trifluoroethyl)indolizin-2-yl)prop-2-yn-1-yl)amino)-6-(methoxy-$d_3$)-N-(methylsulfonyl)picolinamide Cpd-9 (500 mg, 26.9% yield, brown solid). LCMS calculated for $C_{27}H_{28}D_3F_4N_6O_4S$ $[M+H]^+$: m/z=614.2; found: 614.4; $^1H$ NMR (400 MHZ, DMSO-$d_6$) δ 10.85 (s, 1H), 7.68 (d, J=8.0 Hz, 1H), 7.55 (d, J=6.9 Hz, 1H), 7.07 (d, J=8.1 Hz, 1H), 6.78 (s, 1H), 6.74 (d, J=7.8 Hz, 1H), 6.51 (t, J=7.2 Hz, 1H), 5.86 (d, J=7.5 Hz, 1H), 5.74 (d, J=8.3 Hz, 1H), 4.57 (dtd, J=49.6, 9.3, 4.7 Hz, 1H), 4.28 (d, J=6.2 Hz, 2H), 3.95 (q, J=10.7 Hz, 2H), 3.49 (d, J=4.2 Hz, 1H), 3.10 (p, J=5.4 Hz, 1H), 2.77-2.62 (m, 1H), 2.24 (s, 3H), 2.19-1.90 (m, 3H), 1.61-1.39 (m, 1H).

Example 10: 5-((3-(8-(((3R,4R)-3-Fluoro-1-methylpiperidin-4-yl)amino)-3-(2,2,2-trifluoroethyl)indolizin-2-yl)prop-2-yn-1-yl)amino)-6-(methoxy-$d_3$)-N-(methylsulfonyl)picolinamide (Cpd-10, i.e., Compound 10)

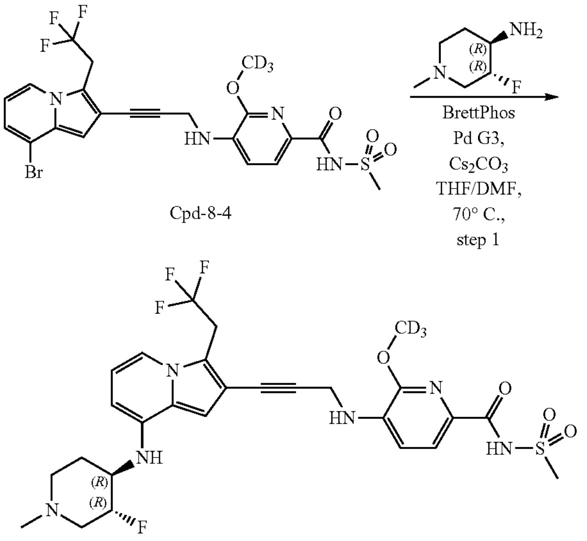

Cpd-8-4

Cpd-10

Step 1: 5-((3-(8-(((3R,4R)-3-Fluoro-1-methylpiperidin-4-yl)amino)-3-(2,2,2-trifluoroethyl)indolizin-2-yl)prop-2-yn-1-yl)amino)-6-(methoxy-$d_3$)-N-(methylsulfonyl)picolinamide Under argon atmosphere, a mixture of 8-bromo-2-(3-((2-(methoxy-$d_3$)-6-((methylsulfonyl)carbamoyl)pyridin-3-yl)amino)prop-1-yn-1-yl)-3-(2,2,2-trifluoroethyl)indolizine Cpd-8-4 (1.80 g, 3.20 mmol), (3R,4R)-3-fluoro-1-methylpiperidin-4-amine (500 mg, 3.78 mmol), BrettPhos Pd G3 (600 mg, 662 μmol), and cesium carbonate (3.44 g, 10.6 mmol) in THF (20 mL) and DMF (10 mL) was stirred at 70° C. for 3 hours. The system was cooled and concentrated, and the residue was purified by silica gel column chromatography (MeOH:DCM=1:24) to obtain the product 5-((3-(8-(((3R,4R)-3-fluoro-1-methylpiperidin-4-yl)amino)-3-(2,2,2-trifluoroethyl)indolizin-2-yl)prop-2-yn-1-yl)amino)-6-(methoxy-$d_3$)-N-(methylsulfonyl)picolinamide Cpd-10 (1.12 g, 57.0% yield, brown solid). LCMS calculated for $C_{27}H_{28}D_3F_4N_6O_4S$ $[M+H]^+$: m/z=614.2; found: 614.4; $^1H$ NMR (400 MHZ, DMSO-$d_6$) δ 10.89 (s, 1H), 7.68 (d, J=8.0 Hz, 1H), 7.55 (d, J=6.9 Hz, 1H), 7.08 (d, J=8.1 Hz, 1H), 6.81-6.78 (m, 2H), 6.51 (t, J=7.1 Hz, 1H), 5.86 (d, J=7.4 Hz, 1H), 5.74 (d, J=8.3 Hz, 1H), 4.57 (dtd, J=49.6, 9.2, 4.8 Hz, 1H), 4.28 (d, J=6.1 Hz, 2H), 3.95 (q, J=10.7 Hz, 2H), 3.59-3.41 (m, 1H), 3.10 (dt, J=10.9, 5.7 Hz, 1H), 2.77-2.59 (m, 1H), 2.25 (s, 3H), 2.17-1.83 (m, 3H), 1.62-1.38 (m, 1H).

Biological Evaluation

I. Biochemical Assay: Test of Compounds Promoting the Binding of p53 Y220C Mutant With DNA Homogeneous time-resolved fluorescence (HTRF) assay was used to measure the reactivation effect of compounds on the p53 Y220C mutant. The recombinant His-tagged p53 Y220C (94-312) used for HTRF assays was expressed in *E. coli* and purified to the purity of 90% through Ni-NTA column. The biotin-labeled DNA used for HTRF assays was synthesized by Pharmaron Inc, with the specific sequence of 5'-ATTAGGCATGTCTAGGCATGTCTAGG-3' (SEQ ID NO: 1).

The binding of recombinant His-tagged p53 Y220C protein and biotin-labeled DNA was measured using fluorescence resonance energy transfer (FRET). For FRET assays, binding between p53 mutants and DNA sequences was measured by detecting the fluorescence of the interaction between an anti-His antibody (Cisbio, 61HI2KLA) conjugated to Eu and $d_2$-conjugated streptavidin (Cisbio, 610SADLF) bound to a biotin-labeled DNA molecule.

Compounds were prepared into 2 mM stock solutions and serially diluted into 10 concentrations at a 1:3 ratio in DMSO. Each 200-fold working concentration compound was sequentially diluted to 4-fold working concentration. 4 μL of compound solution was transferred line by line to a 384-well assay plate using Echo, containing 2 replicates per column. 4 μL of p53 solution was added to the assay plate. 4 μL of biotin DNA solution was added to the assay plate, and then 4 μL of assay solution (His-Eu antibody and streptavidin-$d_2$) was added to each well of the assay plate. The assay plate was incubated overnight and protected from light. Fluorescence was read on BMG (BMG LRBTECH).

The ratio of each well was calculated (ratio_665 nm/615 nm-ratio_background). The activity % was calculated as follows:

$$C = (\text{Ave\_Ac} - \text{Ave\_Ba})/(\text{Ave\_Dc} - \text{Ave\_Bd})$$

$$R\ \text{data} = (A - \text{Ave\_Ba} - C*D)/(D - \text{Ave\_Bd})*(\text{Ave\_Dc} - \text{Ave\_Bd})$$

$$\text{Activity}\,\% = R\ \text{data}/\text{Ave\_VC}*100.$$

A: fluorescence intensity of the sample at 665 nm;

D: fluorescence intensity of the sample at 615 nm;

Ba: fluorescence intensity of the plate background at 665 nm;

Bd: fluorescence intensity of the plate background at 615 nm;

Dc: fluorescence intensity of HIS-Eu background at 615 nm;

Ac: fluorescence intensity of streptavidin-$d_2$ background at 665 nm;

VC: DMSO treatment group.

$SC_{150}$ was calculated using Graphpad 8.0 to fit the logarithm of activity % and compound concentration to a non-linear regression (dose response-variable slope).

TABLE 1

Activity of compounds promoting the binding of p53 Y220C mutant with DNA

| Compound number | $SC_{150}$ (nM) |
|---|---|
| Cpd-A | 10 |
| Cpd-B | 15 |
| Cpd-C | 4.6 |
| Cpd-1 | 1.0 |
| Cpd-2 | 0.58 |
| Cpd-3 | 0.74 |
| Cpd-4 | 0.35 |
| Cpd-5 | 1.1 |
| Cpd-6 | 1.7 |
| Cpd-7 | 0.64 |

Cpd-A is selected from WO2021061643A1; Cpd-B is selected from WO2022213975A1;

Cpd-A

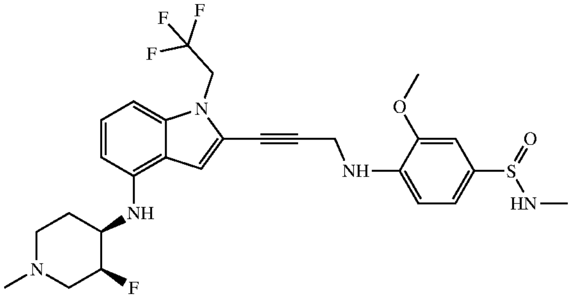

Cpd-B

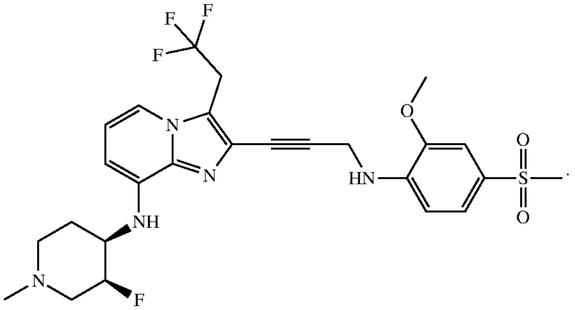

The above data show that the representative compounds of the present disclosure have good activity for promoting the binding of p53 Y220C mutants with DNA, and are obviously superior to the reference compounds.

II. Cellular Assay: Test of Anti-Proliferation Effect on NUGC-3 Cells

The anti-proliferation effect was assessed against the human gastric adenocarcinoma cell line based on the activity of dehydrogenase in cells, which showed good correlation with the number of living cells. Cell line NUGC-3 (JCRB, JCRB0822) was cultured in RPMI 1640 (Invitrogen, 11875-085) medium supplemented with 10% (v/v) fetal bovine serum (BI, 04-002-1A), according to the standard instructions of the American Type Culture Collection. The cell line was authenticated by short tandem repeat profiling.

In the proliferation assay, 1000 NUGC-3 cells were seeded in a 96-well flat clear bottom, TC-treated plate (Corning, 3903) in 200 μL of medium per well, and allowed to recover overnight in culture medium. Compounds were added with increasing concentration, with DMSO treatment serving as a positive control. After 5 days of treatment, the plate was equilibrated to room temperature for 30 minutes, and the number of living cells was measured by the addition of the Cell Counting Kit-8 reagent (MCE, HY-K0301). Absorbance was measured on an Enspire (Perkin elme). The relative viability of each group was presented as the percentage change relative to the positive control group and then fit to a four-parameter logit non-linear curve using the program XLFit (IDBS)

TABLE 2

Anti-proliferation activity of compounds on NUGC-3 cells

| Compound number | NUGC-3 $IC_{50}$ (μM) |
|---|---|
| Cpd-A | 0.78 |
| Cpd-B | 0.36 |
| Cpd-C | 0.23 |
| Cpd-1 | 0.10 |
| Cpd-2 | 0.058 |
| Cpd-4 | 0.097 |
| Cpd-5 | 0.081 |
| Cpd-6 | 0.19 |
| Cpd-7 | 0.070 |
| Cpd-8 | 0.34 |

TABLE 2-continued

Anti-proliferation activity of compounds on NUGC-3 cells

| Compound number | NUGC-3 $IC_{50}$ (μM) |
|---|---|
| Cpd-9 | 0.55 |
| Cpd-10 | 0.90 |

The above data show that the representative compounds of the present disclosure have good inhibitory activity on the proliferation of NUGC-3 cells, and are obviously superior to the reference compounds.

III. Evaluation of Drug-Drug Interactions Related to Metabolic Enzymes (i) Test of the Inhibitory Activity on CYP Isoenzymes at a Single Concentration 1. Experimental Purpose:

To test the inhibitory effect of compounds on CYP isoenzymes at a single concentration.

2. Experimental Instrument and Reagents:

Liver Microsome:

| Species | Gender | Supplier | Cat. No. | Batch | Storage |
|---|---|---|---|---|---|
| Human | Mix | Corning | 452117 | 38298 | −80° C. |

Reagents:

| Compound | Supplier | Cat. No. | Storage |
|---|---|---|---|
| Terfenadine | Sigma-Aldrich | T9652 | 4° C. |
| Tolbutamide | Sigma-Aldrich | T0891 | 4° C. |
| Potassium hydrogen phosphate | Sinopharm | 20032117 | Room temperature |
| Reduced nicotinamide adenine dinucleotide phosphate | Shanghai ABCONE Biotechnology Co., Ltd. | N99640-100MG | −20° C. |
| Phenacetin | Sigma-Aldrich | 101690303 | Room temperature |
| Diclofenac | Sigma-Aldrich | D6899-10G | Room temperature |
| Mephenytoin | Glpbio | GC14486 | −20° C. |
| Dextromethorphan | Sigma-Aldrich | D9684-5G | Room temperature |
| Midazolam | National Institute for Food and Drug Control | PVJT-0H9Z | Room temperature |
| Testosterone | Adamas reagent | 171265 | Room temperature |
| Bupropion | Cayman Chemical Company | 10488 | −20° C. |
| Amodiaquine | Abmole | M5412 | −20° C. |
| B-Naphthoflavone | Sigma-Aldrich | N5757-1G | 4° C. |
| Sulfaphenazole | Sigma-Aldrich | S0758-1G | 4° C. |
| Benzylnirvanol | Shanghai Yuanye Bio-Technology Co., Ltd. | Y43177-5 mg | Room temperature |
| Quinidine | Internation-Laboratory-USA | 1311468-5G | Room temperature |
| Ketoconazole | Sigma-Aldrich | K1003-100MG | 4° C. |

3. Experimental Methods:

8.71 g of $K_2HPO_4$ was dissolved in 950 mL of water. The pH was adjusted to 7.4 with HCl solution. The mixture was adjusted to a final volume of 1000 mL with water. The buffer was filtered through a 0.45 μm filter. The buffer was stored in a refrigerator at 4° C. for future use. Terfenadine/tolbutamide (1 mg/mL each) stock solutions were prepared with DMSO. The above stock solution was diluted with acetonitrile to produce a quenching solution containing 5/10 ng/ml (terfenadine/tolbutamide).

Positive Control Working Solutions:

| CYP enzyme | Inhibitor | Stock solution concentration (mM) | Working solution concentration (mM) | Incubation concentration (μM) | Stock solution volume (μL) | Total volume (μL) | Format |
|---|---|---|---|---|---|---|---|
| 1A2 | β-Naphtho-flavone | 10 | 2 | 10 | 10 | 50 | 5 in 1 |
| 2C9 | Sulfaphenazole | 10 | 2 | 10 | 10 | | |
| 2C19 | Benzylnirvanol | 5 | 1 | 5 | 10 | | |
| 2D6 | Quinidine | 10 | 2 | 10 | 10 | | |
| 3A4/5 | Ketoconazole | 10 | 2 | 10 | 10 | | |
| | Ketoconazole | 2 | 2 | 10 | 50 | 50 | Single |

Substrate Working Solutions:

| CYP enzyme | Substrate | Stock solution concentration (mM) | Working solution concentration (mM) | Incubation concentration (μM) | Stock solution volume (μL) | Total volume (μL) | Format |
|---|---|---|---|---|---|---|---|
| 1A2 | Phenacetin | 250 | 50 | 50 | 2 | 10 | 5 in 1 |
| 2C9 | Diclofenac | 50 | 10 | 10 | 2 | | |
| 2C19 | Mephenytoin | 225 | 45 | 45 | 2 | | |
| 2D6 | Dextromethorphan | 25 | 5 | 5 | 2 | | |
| 3A4/5 | Midazolam | 12.5 | 2.5 | 2.5 | 2 | | |
| | Testosterone | 50 | 50 | 50 | 5 | 5 | Single |

Liver microsomes were thawed in a 37° C. water bath prior to use. Liver microsome working solution (final concentration of 0.5 mg/mL) was prepared. 5 mM NADPH working solution was prepared with phosphate buffered saline. The above stock solution was prepared into a 2 mM working solution with DMSO.

238.5 μL of liver microsome working solution was added to a 1.1 mL tube. 1.5 μL of test compound/control working solution/DMSO was added and mixed well by pipetting several times. The mixture was pre-incubated in water bath with shaking at 37° C. for 5 minutes. After the pre-incubation, 60 μL of NADPH working solution was added and mixed well by pipetting several times. The mixture was incubated in water bath with shaking at 37° C. for 10 minutes. Immediately after incubation, 500 μL of quenching solution was added and vortexed for 1 minute. All samples were centrifuged at 4,000 rpm for 15 minutes at 4° C. 300 μL of the above supernatants were aliquoted for further LC-MS/MS analysis.

4. Data Processing Methods and Results:

Inhibition rate (% inhibition) is calculated using metabolite formation of the test compound or the control compound compared to the matrix control.

TABLE 3

Inhibitory activity of compounds on CYP isoenzymes*

| Compound number | Inhibition rate (%) | | | | | |
|---|---|---|---|---|---|---|
| | CYP1A2 | CYP2C9 | CYP2C19 | CYP2D6 | CYP3A4/5 (Midazolam) | CYP3A4/5 (Testosterone) |
| Cpd-A | 12 | 38 | 42 | 5.5 | 83 | ND |
| Cpd-B | 0.56 | 21 | 31 | 3.6 | 61 | 75 |
| Cpd-C | 18 | 43 | 67 | 9.5 | 79 | ND |
| Cpd-1 | NI | 6.7 | NI | 1.6 | 9.8 | 3.7 |
| Cpd-2 | NI | 8.9 | 8.4 | 7.2 | 8.7 | NI |

*Final compound concentration is 10 μM;

ND: not detected;

NI: no inhibition

The above data show that the compounds of the present disclosure have relatively weak inhibitory activity on CYP isoenzymes, and the risk of drug-drug interaction is significantly lower than that of the reference compounds.

(ii) Determination of the Multi-Concentration Inhibitory Activity Curve of CYP3A4/5 enzymes 1. Experimental Purpose:

To determine the concentration inhibitory activity curve of compounds on CYP3A4/5 enzymes.

2. Experimental Instrument and Materials:

Liver Microsome:

| Species | Gender | Supplier | Cat. No. | Batch | Storage |
|---|---|---|---|---|---|
| Human | Mix | Corning | 452117 | 38298 | −80° C. |

Reagents:

| Compound | Supplier | Cat. No. | Storage |
|---|---|---|---|
| Terfenadine | Sigma-Aldrich | T9652 | 4° C. |
| Tolbutamide | Sigma-Aldrich | T0891 | 4° C. |
| Potassium hydrogen phosphate | Sinopharm | 20032117 | Room temperature |
| Reduced nicotinamide adenine dinucleotide phosphate | Shanghai ABCONE Biotechnology Co., Ltd. | N99640-100MG | −20° C. |
| Midazolam | National Institute for Food and Drug Control | PVJT-0H9Z | Room temperature |
| Testosterone | Adamas reagent | 171265 | Room temperature |
| Ketoconazole | Sigma-Aldrich | K1003-100MG | 4° C. |

3. Experimental Methods:

8.71 g of $K_2HPO_4$ was dissolved in 950 mL of water. The pH was adjusted to 7.4 with HCl solution. The mixture was adjusted to a final volume of 1000 mL with water. The buffer was filtered through a 0.45 μm filter. The buffer was stored in a refrigerator at 4° C. for future use. Terfenadine/tolbutamide (1 mg/mL each) stock solutions were prepared with DMSO. The above stock solution was diluted with acetonitrile to produce a quenching solution containing 5/10 ng/ml (terfenadine/tolbutamide).

Positive Control Working Solutions:

| CYP enzyme | Inhibitor | Stock solution concentration (mM) | Working solution concentration (mM) | Incubation concentration (μM) | Stock solution volume (μL) | Total volume (μL) |
|---|---|---|---|---|---|---|
| 3A4/5 | Ketoconazole | 10 | 2 | 10 | 10 | 50 |
| | Ketoconazole | 2 | 2 | 10 | 50 | 50 |

Substrate Working Solutions:

| CYP enzyme | Substrate | Stock solution concentration (mM) | Working solution concentration (mM) | Incubation concentration (μM) | Stock solution volume (μL) | Total volume (μL) |
|---|---|---|---|---|---|---|
| 3A4/5 | Midazolam | 12.5 | 2.5 | 2.5 | 2 | 10 |
| | Testosterone | 50 | 50 | 50 | 5 | 5 |

Liver microsomes were thawed in a 37° C. water bath prior to use. Liver microsome working solution (final system concentration of 0.5 mg/mL) was prepared. 5 mM NADPH working solution was prepared with phosphate buffered saline. The above stock solution was prepared into a 2 mM working solution with DMSO. The above stock solution was diluted with acetonitrile (4-fold dilution, 6 non-zero concentrations).

238.5 μL of liver microsome working solution was added to a 1.1 mL tube. 1.5 μL of test compound/control working solution/DMSO was added and mixed well by pipetting several times. The mixture was pre-incubated in water bath with shaking at 37° C. for 5 minutes. After the pre-incubation, 60 μL of NADPH working solution was added and mixed well by pipetting several times. The mixture was incubated in water bath with shaking at 37° C. for 10 minutes. Immediately after incubation, 500 μL of quenching solution was added and vortexed for 1 minute. All samples were centrifuged at 4,000 rpm for 15 minutes at 4° C. 300 μL of the above supernatants were aliquoted for further LC-MS/MS analysis.

4. Data Processing Methods and Results:

The half-maximal inhibitory concentration ($IC_{50}$) was calculated using Graph Pad Prism.

TABLE 4

Inhibitory activity of compounds on CYP3A4/5 enzymes

| Compound number | CYP3A4/5 $IC_{50}$ (μM) (Midazolam) | CYP3A4/5 $IC_{50}$ (μM) (Testosterone) |
|---|---|---|
| Cpd-A | 2.3 | 0.89 |
| Cpd-B | 5.8 | 3.2 |
| Cpd-C | 3.8 | ND |
| Cpd-1 | >50 | >50 |
| Cpd-2 | >50 | >50 |

ND: Not detected

The above data show that the representative compounds of the present disclosure have no obvious inhibitory activity on CYP3A4/5 enzymes, and the risk of drug-drug interaction is significantly lower than that of the reference compounds.

IV. In Vitro Metabolic Stability Evaluation: Study on the Metabolic Stability of Liver Microsomes:

1. Experimental Purpose:

To evaluate the metabolic stability of the test compound in human/rat/mouse liver microsomes.

2. Experimental Reagents and Materials:

Reagents:

| Reagent name | Manufacturer | Cat. No. | Storage conditions |
|---|---|---|---|
| Terfenadine | Sigma-Aldrich | T9652 | 2 to 8° C. |
| Tolbutamide | Sigma-Aldrich | T0891 | 2 to 8° C. |
| $K_2HPO_4$ | SCR | 20032117 | RT |
| Reduced nicotinamide adenine dinucleotide phosphate (NADPH) | ACROS | 328742500 | −20° C. |

Materials:

| Experimental | Gender | Manufacturer | Cat. No. | Storage |
|---|---|---|---|---|
| Human liver | Mixed | Corning | 452117 | −80° C. |
| Rat liver | Male | BioreclamationIVT | M00001 | −80° C. |
| Mouse liver | Male | BioreclamationIVT | M00501 | −80° C. |

3. Experimental Methods:

The test compound and the positive control compound (dextromethorphan as a control compound) were dissolved respectively in DMSO to prepare a stock solution with a concentration of 10 mM, and the above stock solution was diluted into 200 μM working solution with DMSO. 8.709 g of potassium hydrogen phosphate ($K_2HPO_4$) was dissolved in 950 mL of water, and the pH value of the solution was adjusted to 7.4 with hydrochloric acid, and then the volume was adjusted to 1000 mL with water. After filtration using a 0.22 μm filter membrane, the mixture was stored in a 4° C. refrigerator for later use. After liver microsomes of various species (protein concentration of 20 mg/mL) were thawed in a 37° C. water bath, the liver microsomes were diluted with a phosphate buffer respectively to obtain a liver microsome working solution with protein concentration of 0.629 mg/mL. 5 mM NADPH solution was prepared using the above phosphate buffer for later use. 1 mg/mL stock solution of terfenadine/tolbutamide was prepared with DMSO and then diluted with a 50% methanol/50% acetonitrile mixed solution to a reaction stop solution containing 5/10 ng/mL (terfenadine/tolbutamide) internal standard.

238.5 μL of liver microsome working solutions of various species were added to a 1.1 mL microtube, and 1.5 μL of the test compound working solution or the positive control compound (dextromethorphan) working solution (200 μM) was added respectively, mixed well, and pre-incubated in a 37° C. water bath for 5 minutes. 60 μL of NADPH solution was added to start the reaction, and after mixing well, at the time points of 0, 5, 15, 30, and 60 minutes after the reaction, 30 μL of the reaction mixture was respectively pipetted and added to 300 μL of the reaction stop solution. Samples from all time points were vortexed vigorously for 1 minute and centrifuged at 4000 rpm for 15 minutes at 4° C. 100 μL of the supernatant was added to 100 μL of pure water and mixed well for LC-MS/MS analysis.

4. Data Processing Methods:

The slope (ke) was determined by plotting the natural logarithm of the percentage of compound remaining against time, and the Tin and intrinsic clearance ($CL_{int}$) were calculated based on the first-order kinetic formula:

The compound remaining rate is calculated as follows:

$$\%\text{ remaining rate} = \frac{\text{ratio of compound peak area to internal standard peak area at each time point}}{\text{ratio of compound peak area to internal standard peak area at initial } T0 \text{ time point}} \times 100$$

Intrinsic clearance $CL_{int}$ (μL/min/mg protein)= $0.693*1000/T_{1/2}$/protein concentration (0.5 mg protein/mL)

TABLE 5

Metabolic stability of compounds in human/rat/mouse liver microsomes

| Compound number | Species | In vitro $t_{1/2}$ (min) | In vitro $Cl_{int}$ (μL/min/mg protein) |
|---|---|---|---|
| Cpd-A | Human | 41 | 33.6 |
| | Rat | 30 | 46.1 |
| | Mouse | 27 | 50.7 |
| Cpd-C | Human | 49 | 28.3 |
| | Rat | 23 | 61.5 |
| | Mouse | 17 | 83.9 |
| Cpd-1 | Human | 136 | 7.3 |
| | Rat | 28 | 35.0 |
| | Mouse | 72 | 13.7 |
| Cpd-2 | Human | >256 | <5.4 |
| | Rat | 119 | 11.7 |
| | Mouse | 110 | 12.6 |

The above data show that the representative compounds of the present disclosure have excellent metabolic stability in the liver microsomes of various species and are obviously superior to the reference compounds.

V. In Vitro Metabolic Stability Evaluation: Metabolic Stability Test in Hepatocytes 1. Experimental Purpose:

To determine the metabolic stability of compounds in human/rat/mouse hepatocytes.

2. Experimental materials:

| Species | Strain | Gender | Supplier |
|---|---|---|---|
| Human | N/A | Mix | BioIVT |
| Rat | Sprague Dawley | Male | BioIVT |
| Mouse | ICR/CD-1 | Male | BioIVT |

3. Experimental Design 3.1 Preparation of Compound Working Solution

The test compound and the control drug verapamil powder were prepared into a high concentration stock solution using DMSO, and diluted to a 100 μM working solution with 50% acetonitrile/water before use, with final concentrations of 1 μM for the test compound and verapamil.

3.2 Preparation of Hepatocytes 1) 49.5 mL of Williams' Medium E and 0.5 mL GlutaMAX were mixed as the incubation solution. The hepatocyte recovery solution and the incubation solution were pre-warmed in a 37° C. water bath for at least 15 minutes prior to use.

2) A tube of cryopreserved hepatocytes was taken, ensuring that the hepatocytes were still in a cryogenic frozen state prior to resuscitation. The hepatocytes were quickly placed in a 37° C. water bath and gently shaken until all ice crystals were completely dispersed, sprayed with 70% ethanol and transferred to a biosafety cabinet.

3) The contents of the hepatocyte tube were poured into a centrifuge tube containing 50 mL of recovery medium, which were centrifuged at 100 g for 10 minutes. After centrifugation, the recovery medium was aspirated, and sufficient incubation medium was added to obtain a cell suspension having a cell density of approximately $1.5\times10^6$ cells/mL.

4) Cellometer Vision was used to count hepatocytes and determine the density of viable cells. The survival rate of hepatocytes must be greater than 75%. The hepatocyte suspension was diluted with incubation medium to a viable cell density of $0.5\times10^6$ cells/mL.

5) A portion of hepatocyte suspension with a density of $0.5\times10^6$ cells/mL was boiled in water for 5 minutes to inactivate as a negative control. After cells were inactivated, substrate conversion mediated by non-cellular enzymes could be easily investigated.

3.3 Experimental Methods 1) 198 μL of the suspension of live or inactivated cells was transferred to a 96-well deep-well plate, which was then placed on a vortexer and preheated in an incubator for 10 minutes. Live cells were incubated in duplicate, while inactivated cells were incubated in single.

2) 2 μL of 100 μM test compound or verapamil was added to each well for the reaction initiation, and the deep-well plate was placed back on the incubator vortexer.

3) 25 μL of the suspension were taken from the incubated samples at 0, 15, 30, 60, 90, and 120 minutes, respectively, and added to 150 μL of acetonitrile containing internal standards (200 nM alprazolam, 200 nM labetalol, 2 μM ketoprofen, and 200 nM caffeine) to terminate the reaction. The mixture was vortexed for 10 minutes and centrifuged at 3220 g and 4° C. for 30 minutes. After centrifugation was completed, 100 μL of the supernatant and 100 μL of ultra-pure water were mixed well for UPLC-MS/MS analysis detection.

4. Data Analysis

All data calculations were performed using Microsoft Excel software. Peak areas were detected by extracting the ion chromatogram. The in vitro half-life ($t_{1/2}$) of the parent drug was detected by linear fitting of the natural logarithm of the percentage of parent drug eliminated with time.

The in vitro half-life ($t_{1/2}$) was calculated by the slope:

$$\text{in vitro } t_{1/2} = 0.693/k$$

In vitro intrinsic clearance (unit μL/min/$10^6$ cells) was calculated using the following formula:

$$\text{in vitro } CL_{int} = \text{kV}/N$$

V=incubation volume per well (0.2 mL);

N=number of cells per well ($0.1\times10^6$ cells)

TABLE 6

Metabolic stability of compounds in human/rat/mouse hepatocytes

| Compound number | Species | In vitro $t_{1/2}$ (min) | In vitro $Cl_{int}$ (μL/min/$10^6$ cells) |
|---|---|---|---|
| Cpd-A | Human | 61 | 22.7 |
| | Rat | 73 | 19.0 |
| | Mouse | 164 | 8.5 |
| Cpd-B | Human | 82 | 16.8 |
| | Rat | 22 | 63.8 |
| | Mouse | 7 | 197.9 |
| Cpd-C | Human | 75 | 18.4 |
| | Rat | 88 | 15.7 |
| | Mouse | 44 | 31.8 |
| Cpd-1 | Human | >511 | <2.7 |
| | Rat | >511 | <2.7 |
| | Mouse | >511 | <2.7 |

TABLE 6-continued

| Metabolic stability of compounds in human/rat/mouse hepatocytes | | | |
|---|---|---|---|
| Compound number | Species | In vitro $t_{1/2}$ (min) | In vitro $Cl_{int}$ (μL/min/$10^6$ cells) |
| Cpd-2 | Human | >511 | <2.7 |
| | Rat | >511 | <2.7 |
| | Mouse | >511 | <2.7 |

The above data show that the representative compounds of the present disclosure have excellent metabolic stability in human/rat/mouse hepatocytes and are obviously superior to the reference compounds.

VI. Cardiac Safety Evaluation: HERG Potassium Channel Inhibitory Activity Test

1. Experimental Purpose:

The manual patch-clamp technique was used to evaluate whether test compounds have potential inhibitory effects on the voltage-gated potassium channel hERG. This experiment was conducted to detect the effect of compounds in five concentrations on hERG channel current, obtaining a dose-effect curve and calculating the $IC_{50}$.

2. Experimental Instrument and Reagents:

| Experimental materials | Supplier (Cat. No.) |
|---|---|
| 6 cm cell culture dish | Shanghai Yes Service Biotech, Inc. (150462) |
| 3.5 cm cell culture dish | Shanghai Yes Service Biotech, Inc. (150460) |
| Dialyzed fetal bovine serum | Shanghai Bohan Biotechnology Co., Ltd. (BS-0005-500) |
| DMSO | Beijing Solarbio Science & Technology Co., Ltd. (D8371) |
| DMEM medium | Thermo Fisher Scientific (China) Co., Ltd. (10569044) |
| HEPES | Thermo Fisher Scientific (China) Co., Ltd. (15630080) |
| Trypsin | Thermo Fisher Scientific (China) Co., Ltd. (12604) |
| Phosphate buffered saline (without calcium and magnesium ions) | Beijing Solarbio Science & Technology Co., Ltd. (D1040) |
| Penicillin-streptomycin solution | Thermo Fisher Scientific (China) Co., Ltd. (15140122) |
| MEM non-essential amino acid solution | Thermo Fisher Scientific (China) Co., Ltd. (11140050) |
| Geneticin (G418) | Thermo Fisher Scientific (China) Co., Ltd. (11811031) |
| Blasticidin | Thermo Fisher Scientific (China) Co., Ltd. (R21001) |
| Polylysine | Thermo Fisher Scientific (China) Co., Ltd. (P4832) |
| Dofetilide | Beijing Express Technology Development Co., Ltd. (D525700) |
| Doxycycline | Sigma-Aldrich (Shanghai) Trading Co., Ltd. (D9891) |
| Carbon dioxide incubator | Thermo Fisher Scientific (China) Co., Ltd. (Thermo371) |
| Glass electrode drawing machine | Japan NARISHIGE Company (PC-10 Puller) |
| Micromanipulator positioner | Qingdao Sources Optics Co., Ltd. (MC1000e) |
| Perfusion system | American ALA Company (VM8 gravity drug delivery system) |
| Vacuum pump | German Chemvak Company (V300) |
| Osmometer | Ashern Company (Osmo310) |

3. Experimental Methods:

Cell line and cell culture: HEK293 cell line stably expressing the hERG ion channel (Cat. No.: K1236) was purchased from Invitrogen Company. The cell line was cultured in a medium containing 85% DMEM, 10% dialyzed fetal bovine serum, 0.1 mM non-essential amino acid solution, 100 U/mL penicillin-streptomycin solution, 25 mM HEPES, 5 g/mL blasticidin, and 400 μg/mL geneticin. When the cell density grows to 40% to 80% of the bottom area of the culture dish, the cells were digested with trypsin and passaged three times per week. Prior to the experiment, cells were cultured in a 3.5 cm culture dish at a density of $5\times10^5$, induced with 1 μg/mL doxycycline for 48 hours, and then the cells were digested and seeded on glass slides for subsequent manual patch clamp experiments.

Solution preparation: extracellular fluid (in mM): 132 sodium chloride, 4 potassium chloride, 3 calcium chloride, 0.5 magnesium chloride, 11.1 glucose, and 10 HEPES (pH adjusted to 7.35 with sodium hydroxide). Intracellular fluid (in mM): 10 EGTA, 10 HEPES, 10 potassium chloride, 10 sodium chloride, and 110 potassium fluoride (pH adjusted to 7.2 with potassium hydroxide). The osmotic pressure of the solution was controlled between 280 to 300 mOsmol/kg. The solution was filtered and stored at 4° C. prior to use.

Test compound solution preparation: Following the standard operating procedure, test compounds were dissolved in DMSO and prepared into a stock solution with a final concentration of 10 mM. The stock solution was gradiently diluted with DMSO as the solvent in a 1:3 ratio into three other intermediate concentration solutions at concentrations of (mM): 3.33, 1.11, and 0.37, respectively. Prior to the start of the experiment, the test compound gradient intermediate solution was diluted with extracellular fluid again in a 1:1000 ratio into working solutions of a series of concentrations, and the working solution of 30 μM was prepared into a working solution in a 1:333.33 ratio using a stock solution of 10 mM, and the final concentrations of which were (μM): 30, 10, 3.33, 1.11, and 0.37, respectively. The DMSO content in the working solution was 0.1 to 0.3% (v/v). 5 working solutions with different concentration gradients of 30, 10, 3.33, 1.11, and 0.37 μM were used to determine the potential inhibitory effect of compounds on hERG channels and to fit the dose-effect curve and calculate $IC_{50}$.

Experimental procedure: A coverslip loaded with HEK293 cells in a culture dish was placed in the perfusion chamber of the microscope stage. A suitable cell was placed in the center of the field of view under an Olympus IX71 or IX73 inverted microscope, and the tip of the glass electrode was found using a ×10 objective lens, and placed in the center of the field of view. Then the electrode was moved downward using a micromanipulator, while the coarse focus screw was adjusted to slowly bring the electrode closer to the cell. On the point of approaching the cell, the objective lens was switched to a ×40 objective lens for observation, and an electrode was gradually brought closer to the surface of the cell using a micromanipulator for fine adjustment. The negative pressure was given to form a seal between the electrode tip and the cell membrane with a resistance higher than 1 GΩ. The transient capacitive current Cfast was compensated in the voltage clamp mode. The brief negative pressure was then applied repeatedly to rupture the membrane, eventually forming a whole-cell recording mode. Under the condition that the membrane potential was clamped at −60 mV, the slow capacitive current Cslow, the cell membrane capacitance (Cm), and the input membrane resistance (Ra) were compensated respectively. After the cells were stable, the clamping voltage was changed to −90 mV, the sampling frequency was set at 20 kHz, and the filtering frequency was 10 kHz. The condition for detecting the leakage current was that the clamping voltage changed to −80 mV and the time duration was 500 ms. The hERG current test method was as follows: A 4.8-second depolarizing command voltage was applied to bring the membrane potential from −80 mV to +30 mV, and then a 5.2-second repolarizing voltage was instantly applied to lower the membrane potential to −50 mV to remove channel inactivation, thereby allowing the hERG tail current to be observed. The peak value of the tail current was the magnitude of the hERG current. The hERG current used to detect the test compound was continuously recorded for 120 seconds before administration to evaluate the stability of the hERG current generated by the test cells. Only stable cells within the acceptable range of the evaluation criteria were allowed to proceed to the subsequent compound testing. Test of the inhibitory effect of the test compound on hERG current: First, the hERG current measured in the extracellular fluid containing 0.1% DMSO was used as the detection baseline. After the hERG current had been stable for at least 5 minutes, the solution containing the test compound was sequentially perfused around the cells from a low concentration to a high concentration. After each perfusion was completed, approximately 5 minutes were waited to allow the compounds to fully act on the cells, and hERG currents were synchronously recorded. The last 5 hERG current values were recorded after the currents to be recorded tended to stabilize, and the average value was taken as the final current value at a specific concentration. After testing the compound, 450 nM dofetilide was added to the same cell, and the current was completely inhibited, serving as a positive control for that cell. At the same time, the positive compound dofetilide was tested before and after the end of the test drug experiment using the same patch clamp system for synchronous detection to ensure the reliability and sensitivity of the entire detection system. The above test steps were repeated on two separate test cells (n=2).

4. Data Processing Methods and Results:

Data quality control standards: The initial seal resistance was greater than 1 GΩ; The series resistance was less than 15 MΩ and the voltage error of the series resistance was less than 5 mV; The leakage current at the detection voltage was less than 50% of the current value under this condition; The tail current was greater than the plateau current of the pre-pulse, with an initial tail current value greater than 250 pA; The membrane breakthrough resistance Ra was less than 15 MΩ; The decay rate of the tail current per minute was less than 2.5%.

Data analysis: Only data that meets the above criteria could be analyzed according to the following steps.

Note: Data are output by PatchMaster software.

After being infused with blank solvent or compound gradient solutions, stable 5 consecutive current values were obtained, and the average value was calculated, respectively, as "tail $\text{current}_{blank}$" and "tail $\text{current}_{compound}$".

The current suppression percentage is calculated by the following formula.

$$\text{tail current inhibition rate} = \left(1 - \frac{\text{tail current}_{compound} - \text{tail current}_{positive\ drug}}{\text{tail current}_{blank} - \text{tail current}_{positive\ drug}}\right) \times 100$$

The dose-effect curve was fitted by Graphpad Prism 8.0 software and the $IC_{50}$ value was calculated.

TABLE 7

Inhibitory activity of compounds on hERG

| Compound number | hERG $IC_{50}$ (μM) |
|---|---|
| Cpd-A | 19 |
| Cpd-B | 5.5 |
| Cpd-C | 1.4 |
| Cpd-1 | >30 |
| Cpd-2 | >30 |

The above data show that the representative compounds of the present disclosure have a lower risk of potential cardiotoxicity caused by hERG inhibition, and their safety is obviously superior to that of the reference compounds.

VII. In Vivo Pharmacokinetic Study in Mice

1. Experimental Purpose:

To test the pharmacokinetics of compounds in CD-1 mice.

2. Experimental Instrument and Materials:

Animals: CD-1 mice (male)

Instrument:

| Instrument name | Manufacturer | Instrument number |
|---|---|---|
| API4000 Qtrap-Shimadzu 20AT | AB Sciex/Shimadzu | TW-017-0002 |
| Large benchtop refrigerated centrifuge | Eppendorf | TW-007-0017 |
| Electronic balance | Sartorius | TW-001-0013 |
| Pipetting workstation | Sptlabtech | TW-013-0016 |
| Vortex oscillator | DRAGON LAB | TW-005-0013 |
| High-throughput tissue grinder | Ningbo Scientz Biotechnology Co., Ltd. | TW-011-0002 |

Reagents:

| Name | Manufacturer | Cat. No. | Batch number |
|---|---|---|---|
| Acetonitrile | Sigma-Aldrich | 34851 | F222M7L201 |
| Methanol | Sigma-Aldrich | 75851G | WXBD8013V |
| DMSO | Fisher Scientific | D159-4 | 186403 |
| Formic acid | Sigma-Aldrich | F112034 | G2122206 |
| PBS | Shanghai Basal Media | B310KJ | H211017 |

Vehicle:

Intravenous injection: 40% HP-β-CD in water; intragastric administration: 0.2% HPC+0.5% Tween80 in water.

3. Experimental Methods:

6 male mice. Fasting treatment was performed in the evening before the administration, with free access to water. During the experiment, the mice were allowed to eat and drink freely, and administered by intravenous injection or gavage. After administration, the animal status was observed, and abnormal behaviors were recorded. Blood was collected from the orbit at 0.0833, 0.25, 1, 2, 4, 8, and 24 hours after intravenous injection, and at 0.25, 0.5, 1, 2, 4, 6, 8, and 24 hours after intragastric administration. 20 μL of plasma sample was taken and added with 250 μL of acetonitrile (containing dexamethasone as an internal standard) to precipitate proteins. The mixture was centrifuged at 4° C. and 4000 rpm for 20 minutes, and 180 μL of the supernatant was taken and mixed with 180 μL of an aqueous solution containing 0.1% formic acid in a 96-well plate. Then, 10 μL of the sample was taken for LC-MS/MS detection.

4. Data Processing Methods and Results:

The standard curve was established using the internal standard method, with the theoretical standard curve concentration as the X-axis and the peak area ratio as the Y-axis (peak area of the test compound/peak area of internal standard). Linear regression method (weighting factor 1/X2) was used, $R^2$>0.9900. Unknown samples were calculated by the standard curve. Pharmacokinetic parameters were calculated by the non-compartmental analysis model of WinNonlin 8.2 software and were presented in a report, including $Cl_{int}$, $C_{max}$, AUC, etc.

TABLE 8

Pharmacokinetic parameters of compounds in CD-1 mice

| | IV 1 mg/kg | | PO 10 mg/kg | |
|---|---|---|---|---|
| Compound number | $Cl_{int}$ (mL/min/kg) | $AUC_{0-t}$ (hr*μM) | $C_{max}$ (μM) | $AUC_{0-t}$ (hr*μM) |
| Cpd-A | 18 | 1.7 | 2.2 | 10.4 |
| Cpd-2 | 15 | 1.7 | 5.9 | 15.7 |

The above data show that the representative compound of the present disclosure has a lower clearance and a higher oral exposure in mice, and is superior to the reference compound.

VIII. In Vivo Pharmacokinetic Study in Rats

1. Experimental Purpose:

To test the pharmacokinetics of compounds in SD rats.

2. Experimental Instrument and Materials:

Animal: SD rats (male)

Instrument:

| Instrument name | Manufacturer | Instrument number |
|---|---|---|
| API4000 Qtrap-Shimadzu 20AT | AB Sciex/Shimadzu | TW-017-0002 |
| Large benchtop refrigerated centrifuge | Eppendorf | TW-007-0017 |
| Pipetting workstation | Sptlabtech | TW-013-0016 |
| Vortex oscillator | DRAGON LAB | TW-005-0013 |
| High-throughput tissue grinder | Ningbo Scientz Biotechnology Co., Ltd. | TW-011-0002 |

Reagents:

| Name | Manufacturer | Cat. No. | Batch number |
|---|---|---|---|
| Acetonitrile | Sigma-Aldrich | 34851 | WXBD8733V |
| Methanol | Sigma-Aldrich | 75851G | P2478457 |
| DMSO | Fisher Scientific | D4540 | BCCH3267 |
| Formic acid | Sigma-Aldrich | F112034 | B2320164 |
| PBS | Shanghai Basal Media | B310KJ | K211007 |

Vehicle:

Intravenous injection: 40% HP-β-CD in water; intragastric administration: 0.2% HPC+0.5% Tween80 in water.

3. Experimental Methods:

6 male rats. Fasting treatment was performed in the evening before the administration, with free access to water. During the experiment, the rats were allowed to eat and drink freely, and administered by intravenous injection or gavage. After administration, the animal status was observed, and abnormal behaviors were recorded. Blood was collected via jugular vein puncture at 0.0833, 0.25, 1, 2, 4, 8, and 24 hours after intravenous injection; Blood was collected via jugular vein puncture at 0.25, 0.5, 1, 2, 4, 6, 8, and 24 hours after intragastric administration. 50 μL of plasma sample was taken and added with 500 μL of acetonitrile (containing dexamethasone as an internal standard) to precipitate proteins. The mixture was centrifuged at 4° C. and 4000 rpm for 20 minutes, and 300 μL of the supernatant was taken and mixed with 300 μL of Watsons aqueous solution in a 96-well plate. Then, 5 μL of the sample was taken for LC-MS/MS detection.

4. Data Processing Methods and Results:

The standard curve was established using the internal standard method, with the theoretical standard curve concentration as the X-axis and the peak area ratio as the Y-axis (peak area of the test compound/peak area of internal standard). Linear regression method (weighting factor 1/X2) was used, $R^2$>0.9900. Unknown samples were calculated by the standard curve. Pharmacokinetic parameters were calculated by the non-compartmental analysis model of WinNonlin 8.2 software and were presented in a report, including $Cl_{int}$, $C_{max}$, AUC, etc.

TABLE 9

Pharmacokinetic parameters of compounds in SD rats

| | IV 1 mg/kg | | PO 10 mg/kg | |
|---|---|---|---|---|
| Compound number | $Cl_{int}$ (mL/min/kg) | $AUC_{0-t}$ (hr*μM) | Cmax (μM) | $AUC_{0-t}$ (hr*μM) |
| Cpd-A | 7.1 | 4.2 | 3.2 | 35.8 |
| Cpd-2 | 3.3 | 8.4 | 8.9 | 58.4 |

The above data show that the representative compound of the present disclosure has a lower clearance and a higher oral exposure in rats, and is obviously superior to the reference compound.

IX. In Vivo Efficacy Study in Human Gastric Cancer NUGC-3 Xenograft Mouse Model

1. Experimental Purpose:

To test the in vivo anti-tumor activity of compounds in the subcutaneous human gastric cancer NUGC-3 xenograft model in female NUNU mice.

2. Experimental Materials:

Animals: 6 to 8 weeks old female NUNU mice;

Reagents:

| Reagent name | Supplier | Cat. No. | Batch number |
|---|---|---|---|
| Penicillin-streptomycin double antibody | Gibco | 15240-062 | 2441816 |
| Trypsin-EDTA | Gibco | 25200-072 | 2756239 |
| RPMI-1640 | Gibco | C22400500BT | 6123180 |
| DPBS | Corning | 21-031-CVC | 21031095 |
| FBS | Dongling | FBSV500 | A22JV |
| Matrigel | Corning | 354234 | 3012001 |
| Glacial acetic acid | Alfa Aesar | 36289 | U02F788 |
| Tween80 | Sigma | P1754 | WXBD4333V |
| Dimethyl sulfoxide (DMSO) | Leyan | 1083196 | Lg0913304311 |
| Solutol | Sigma | 42966 | BCCJ5912 |

Cpd-A vehicle: 0.2% HPC, 0.5% Tween80 in water (w/v/v);

Cpd-2 vehicle: 5% DMSO/10% Solutol HS 15/85% pH 4.65±0.10 acetate buffer.

3. Experimental Protocol:

Cell culture: NUGC-3 cells were cultured in RPMI-1640 medium containing 10% FBS.

Molding and grouping: NUGC-3 cells in the exponential growth phase ($5\times10^6$) were harvested, resuspended in 0.2 mL of PBS and Matrigel (1:1), and then inoculated subcutaneously into the right flank of NUNU mice to establish a subcutaneous xenograft model. Mice were observed daily for healthy status and tumor growth after cell inoculation. On the 5th day after inoculation, 36 animals were selected, grouped, and the tumor volume of the animals in the group was approximately 150.0 $mm^3$. The study was divided into 6 groups, with 6 mice in each group, and the administration was performed on the same day (see Table 10).

4. Experimental Design:

Table 10 is the grouping and administration information for the efficacy experiment. Mice in the G1 group were orally administered vehicle control (5% DMSO/10% Solutol HS 15/85% pH 4.65±0.10 acetate buffer) once a day for a total of 19 days. Mice in the G2 group were orally administered Cpd-A once a day at a dose of 50 mg/kg for a total of 19 days. Mice in the G3 group were orally administered Cpd-A once a day at a dose of 100 mg/kg for a total of 19 days. Mice in the G4 group were orally administered Cpd-2 once a day at a dose of 25 mg/kg for a total of 19 days. Mice in the G5 group were orally administered Cpd-2 once a day at a dose of 50 mg/kg for a total of 19 days. Mice in the G6 group were orally administered Cpd-2 once a day at a dose of 100 mg/kg for a total of 19 days.

TABLE 10

In vivo efficacy study design of NUGC-3 xenograft mouse model

| Group | N | Compound | Dose (mg/kg) | Administration volume (mL/kg) | Administration route | Administration frequency (post grouping) |
|---|---|---|---|---|---|---|
| G1 | 6 | Vehicle | — | 10 | PO | QD*19 Days |
| G2 | 6 | Cpd-A | 50 | 10 | PO | QD*19 Days |
| G3 | 6 | Cpd-A | 100 | 10 | PO | QD*19 Days |
| G4 | 6 | Cpd-2 | 25 | 10 | PO | QD*19 Days |
| G5 | 6 | Cpd-2 | 50 | 10 | PO | QD*19 Days |
| G6 | 6 | Cpd-2 | 100 | 10 | PO | QD*19 Days |

5. Experimental Observation and Result Analysis:

Experimental observation: The health status and mortality of the animals were monitored daily. Routine checks included observing the effect of tumor growth and drug treatment on animals' normal behavior such as mobility, food and water consumption, body weight gain/loss, eye/hair matting and any other abnormal effect. The number of deaths and side effects of the animals in the group were recorded based on the number of the animals in each group. Clinical symptoms observed during the trial were recorded in the raw data. Tumor volume calculation formula: Tumor volume ($mm^3$)=0.5×(tumor long diameter×tumor short diameter$^2$). During the research process, the entire administration process as well as tumor and body weight measurements were conducted in a Laminar Flow Cabinet.

Data processing: Percentage of tumor growth inhibition TGI (%): TGI %=(1−ΔT/ΔC)×100%; Wherein ΔC is the tumor volume $C_t$–$C_0$ for the control group, $C_0$ is the average tumor volume of the control group at the time of grouping, and $C_t$ is the average tumor volume of the control group after treatment; ΔT is the tumor volume $T_t$–$T_0$ for the treatment group, $T_0$ is the average tumor volume of the treatment group at the time of grouping, and $T_t$ is the average tumor volume of the treatment group after treatment.

Statistical analysis: Tumor volume and animal body weight results are expressed in Mean±SEM. Tumor volumes between different groups were statistically compared and analyzed. All statistical analyses were completed in GraphPad Prism 8.0. The one-way ANOVA method was used to compare whether there was a significant difference in tumor volume or tumor weight between groups, where $p \geq 0.05$ was considered as having no significant difference, $p<0.05$ was considered as having a significant difference, and $p<0.001$ was considered as having an extremely significant difference.

Figure 2:
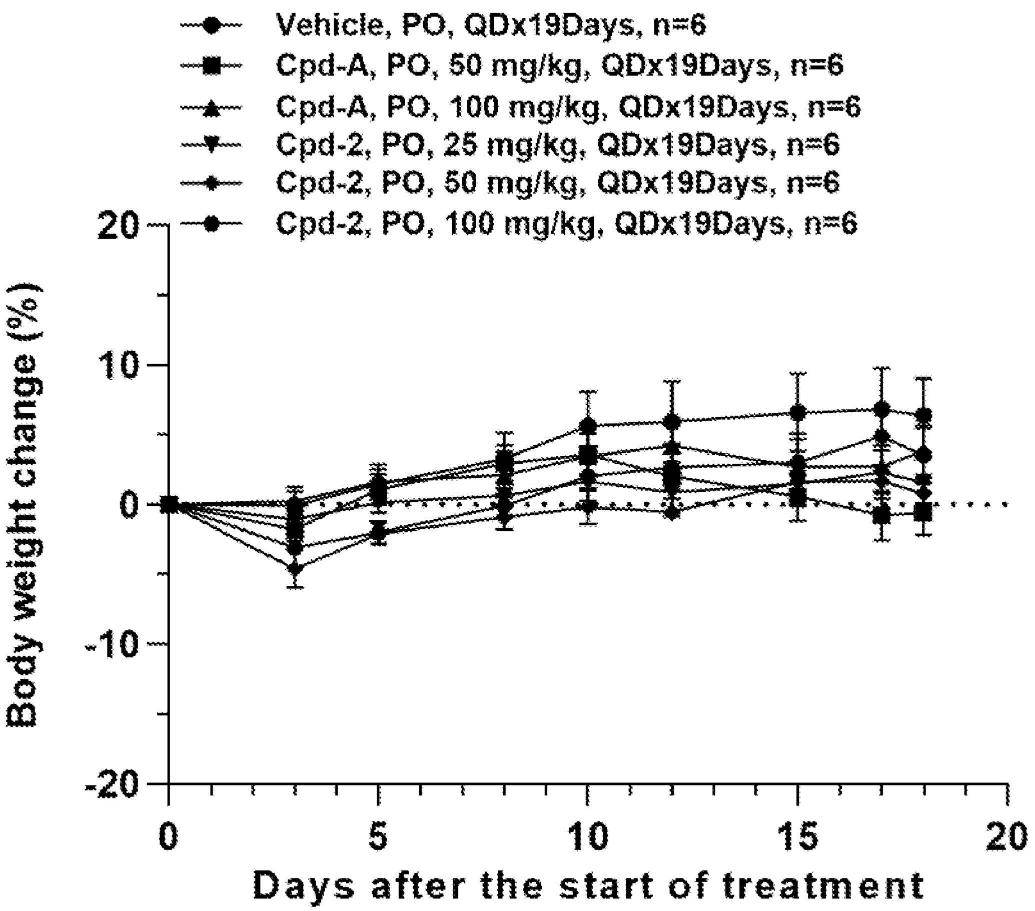
FIG. 2 shows the curves of relative mice body weight change in the control group and each treatment group in the efficacy study of NUGC-3 human gastric cancer xenograft mice model described in test example IX.

6. Experimental Results:

The tumor growth curves of the control group and each experimental group in the efficacy study of the human gastric cancer NUGC-3 xenograft model in mice are as shown in FIG. 1, and the relative body weight changes of the mice in the model are as shown in FIG. 2. The average tumor volume, percentage of tumor growth inhibition TGI (%), and comparison results of animals in each group at the end of the experiment are shown in Table 11.

On the 19th day after grouping, the average tumor volume of G1 (Vehicle) group was 1482.2 $mm^3$, and the average tumor volumes of G2 (Cpd-A, 50 mg/kg, QD), G3 (Cpd-A, 100 mg/kg, QD), G4 (Cpd-2, 25 mg/kg, QD), G5 (Cpd-2, 50 mg/kg, QD), and G6 (Cpd-2, 100 mg/kg, QD) groups were 1208.1 $mm^3$, 399.1 $mm^3$, 615.1 $mm^3$, 202.2 $mm^3$, and 102.5 $mm^3$, respectively. The corresponding percentages of tumor growth inhibition (TGI) were 20.6%, 81.3%, 65.1%, 96.1%, and 103.6%, respectively. Statistical analysis showed that the average tumor volume in G3, G4, G5, and G6 groups was significantly smaller than that in the Vehicle group ($p<0.05$ for all); Wherein the difference in the average tumor volume between G5 and G6 groups and the Vehicle group was extremely significant ($p<0.001$ for both). The above results show that the reference compound Cpd-A exhibits good anti-tumor efficacy in the subcutaneous NUGC-3 mouse model at a high dose of 100 mg/kg, while the representative compound of the present disclosure Cpd-2 exhibits good anti-tumor efficacy at each test dose in this model and the activity has a dose dependency. At the same time, at a lower dose (such as 50 mg/kg, QD), Cpd-2 (TGI=96.1%) has better tumor growth inhibitory activity than Cpd-A (TGI=81.3%) at twice of the dose (100 mg/kg, QD), indicating that Cpd-2 has better anti-tumor efficacy than Cpd-A.

TABLE 11

In vivo efficacy study results of NUGC-3 xenograft mouse model

| Group | Tumor volume ($mm^3$) (at 19 days) | TGI (%)[a] (at 19 days) | p value[b] |
|---|---|---|---|
| G1: Vehicle | 1,482.2 ± 333.8 | — | — |
| G2: Cpd-A, 50 mg/kg | 1,208.1 ± 320.9 | 20.6 | 0.8127 |
| G3: Cpd-A, 100 mg/kg | 399.1 ± 106.3 | 81.3 | 0.0037 |
| G4: Cpd-2, 25 mg/kg | 615.1 ± 157.6 | 65.1 | 0.0243 |
| G5: Cpd-2, 50 mg/kg | 202.2 ± 57.9 | 96.1 | 0.0006 |
| G6: Cpd-2, 100 mg/kg | 102.5 ± 42.1 | 103.6 | 0.0003 |

Note:

[a]TGI (%) = [1 − ($T_{19}$ − $T_0$)/($V_{19}$ − $V_0$)] × 100

[b]p value of comparative analysis of the average tumor volume of each administration group and the average tumor volume of the Vehicle in the G1 group X. In Vivo Efficacy Study in Human Gastric Cancer NUGC-3 Xenograft Rat Model 1. Experimental Purpose:

To test the in vivo anti-tumor activity of compounds in the subcutaneous human gastric cancer NUGC-3 xenograft model in female B-Rag2/IL2rg KO SD rats.

2. Experimental Materials:

Animals: 7 to 9 weeks old female B-Rag2/IL2rg KO SD rats;

Reagents:

| Reagent name | Supplier | Cat. No. | Batch number |
|---|---|---|---|
| Phosphate buffered saline (PBS) | BasalMedia | B310KJ | L211110 |
| RPMI-1640 medium | BasalMedia | L210KJ | D211212 |
| Trypsin | BasalMedia | S310KJ | B121201 |
| Fetal bovine serum | ExcellBio | FSP500 | 012C-0530A |
| Penicillin-streptomycin double antibody 100× | BasalMedia | S110JV | H121101 |
| Matrigel | CORNING | 354234 | 3012001 |
| Solutol HS15 | MeiluneBio | MB1809 | A0413D |
| Acetic acid | Taicang Hushi | NA | 20180322 |
| Sodium acetate | Sigma-Aldrich | S2889 | WXBD3974v |
| Ultrapure water | Guangzhou Watsons | NA | NA |
| DMSO | Sigma-Aldrich | V900090 | WXBF1310V |

Vehicle: 5% DMSO/10% Solutol HS 15/85% pH 4.65 ± 0.10 acetate buffer;

3. Experimental Protocol:

Cell culture: NUGC-3 cells were cultured in RPMI-1640 medium containing 10% FBS.

Molding and grouping: NUGC-3 cells in the exponential growth phase ($1\times10^7$) were harvested, resuspended in 0.2 mL of PBS and Matrigel (1:1), and then inoculated subcutaneously into the right flank of B-Rag2/IL2rg KO SD rats to establish a subcutaneous xenograft model. Rats were observed daily for healthy status and tumor growth after cell inoculation. On the 10th day after inoculation, 24 animals were selected, grouped, and the tumor volume of the animals in the group was approximately 199.0 $mm^3$. The study was divided into 4 groups, with 6 rats in each group, and the administration was performed on the same day (see Table 12).

4. Experimental Design:

Table 12 is the grouping and administration information for the efficacy study. Rats in the G1 group were orally administered vehicle control (5% DMSO/10% Solutol HS 15/85% pH 4.65±0.10 acetate buffer) once a day for a total of 28 days. Rats in the G2 group were orally administered Cpd-2 once a day at a dose of 6.25 mg/kg for a total of 28 days. Rats in the G3 group were orally administered Cpd-2 once a day at a dose of 12.5 mg/kg for a total of 28 days. Rats in the G4 group were orally administered Cpd-2 once a day at a dose of 25 mg/kg for a total of 28 days.

TABLE 12

In vivo efficacy study design of NUGC-3 xenograft rat model

| Group | N | Compound | Administration dose (mg/kg) | Administration volume (mL/kg) | Administration route | Administration frequency |
|---|---|---|---|---|---|---|
| G1 | 6 | Vehicle | — | 10 | PO | QD × 28 days |
| G2 | 6 | Cpd-2 | 6.25 | 10 | PO | QD × 28 days |
| G3 | 6 | Cpd-2 | 12.5 | 10 | PO | QD × 28 days |
| G4 | 6 | Cpd-2 | 25 | 10 | PO | QD × 28 days |

5. Experimental Observation and Result Analysis:

Experimental observation: The health status and mortality of the animals were monitored daily. Routine checks included the effect of tumor growth and drug treatment on animals' normal behavior such as mobility, food and water consumption, body weight gain/loss, eye/hair matting and any other abnormal effect. The number of deaths and side effects of the animals in the group were recorded based on the number of the animals in each group. Clinical symptoms observed during the trial were recorded in the raw data. Tumor volume calculation formula: Tumor volume ($mm^3$)= 0.5×(tumor long diameter×tumor short diameter$^2$). During the research process, the entire administration process as well as tumor and body weight measurements were conducted in a Laminar Flow Cabinet.

Data processing: Percentage of tumor growth inhibition TGITV (%): TGITV %=(1−ΔT/ΔC)×100%; Wherein ΔC is the tumor volume $C_t$−$C_0$ for the control group, $C_0$ is the average tumor volume of the control group at the time of grouping, and $C_t$ is the average tumor volume of the control group after treatment; ΔT is the tumor volume $T_t$−$T_0$ for the treatment group, $T_0$ is the average tumor volume of the treatment group at the time of grouping, and $T_t$ is the average tumor volume of the treatment group after treatment.

Statistical analysis: Tumor volume and animal body weight results are expressed in Mean±SEM. Tumor volumes between different groups were statistically compared and analyzed. All statistical analyses were completed in https://d$_2$k.bio/Efficacy/Invivo. The wilcox.test nominal method was used to compare whether there was a significant difference in tumor volume or tumor weight between groups, where $p \geq 0.05$ was considered as having no significant difference, $p<0.05$ was considered as having a significant difference, and $p<0.01$ was considered as having an extremely significant difference.

Figure 3:
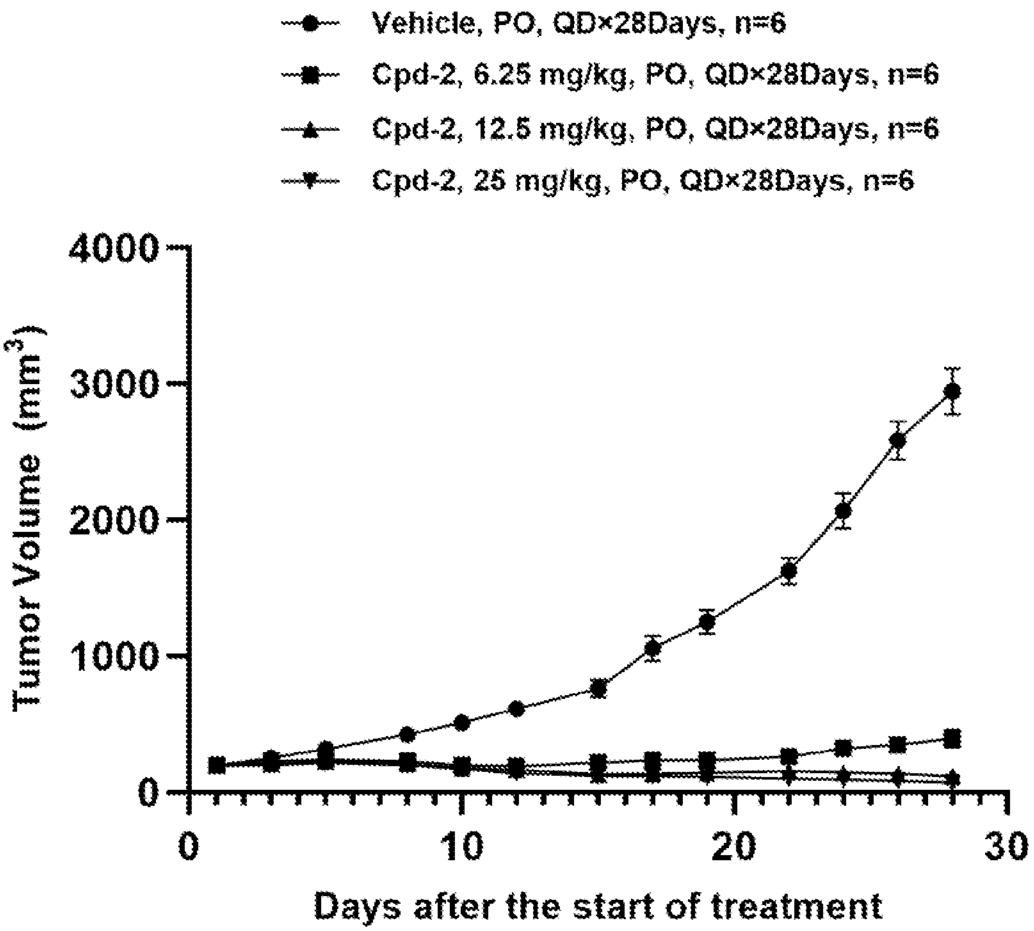
FIG. 3 shows the tumor growth curves of the control group and each treatment group in the efficacy study of NUGC-3 human gastric cancer xenograft rat model described in test example X.
Figure 4:
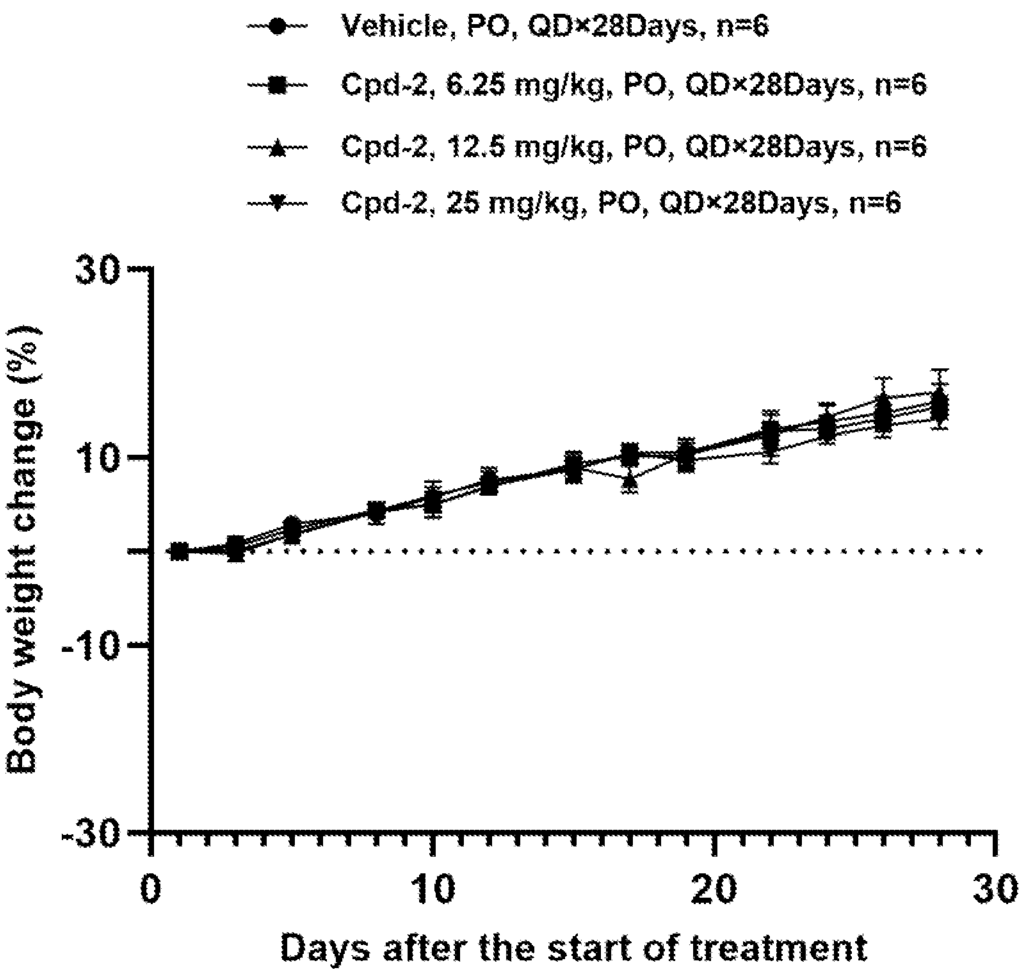
FIG. 4 shows the curves of relative rat body weight change in the control group and each treatment group in the efficacy study of NUGC-3 human gastric cancer xenograft rat model described in test example X.

6. Experimental Results:

The tumor growth curves of the control group and each experimental group in the efficacy study of the human gastric cancer NUGC-3 xenograft model in rats are as shown in FIG. 3, and the relative body weight changes of the rats in the model are as shown in FIG. 4. The average tumor volume, percentage of tumor growth inhibition TGI (%), and comparison results of animals in each group at the end of the experiment are shown in Table 13.

On the 28th day after grouping, the average tumor volume of G1 (Vehicle) group was 2946.2 $mm^3$, and the average tumor volumes of G2 (Cpd-2, 6.25 mg/kg, QD), G3 (Cpd-2, 12.5 mg/kg, QD), and G4 (Cpd-2, 25 mg/kg, QD) groups were 395.0 $mm^3$, 119.2 $mm^3$, and 70.1 $mm^3$, respectively. The corresponding percentages of tumor growth inhibition (TGI) were 92.9%, 102.9%, and 104.7%, respectively. Statistical analysis showed that the difference in the average tumor volume between G2, G3, and G4 groups and the Vehicle group was extremely significant ($p<0.01$ for all). The above results show that the representative compound of the present disclosure Cpd-2 exhibits good anti-tumor efficacy in the subcutaneous NUGC-3 xenograft rat model at each test dose, and the activity has a dose dependency.

TABLE 13

In vivo efficacy study results of NUGC-3 xenograft rat model

| Group | Tumor volume ($mm^3$) (Mean ± SEM) (at 28 days) | $TGI_{TV}$ (%) (at 28 days) | p value[a] |
|---|---|---|---|
| G1: Vehicle, QD × 28 days, p.o. | 2946.2 ± 167.4 | / | / |
| G2: Cpd-2, 6.25 mg/kg, QD × 28 days, p.o. | 395.0 ± 63.1 | 92.9 | 0.0022 |
| G3: Cpd-2, 12.5 mg/kg, QD × 28 days, p.o. | 119.2 ± 10.2 | 102.9 | 0.0022 |
| G4: Cpd-2, 25 mg/kg, QD × 28 days, p.o. | 70.1 ± 14.9 | 104.7 | 0.0022 |

Note:

p value of comparative analysis of the average tumor volume of each administration group and the average tumor volume of the Vehicle in the G1 group.

The invention claimed is:

1. A nitrogen-containing compound of formula I, an isotope-labeled compound thereof, a solvate thereof, a pharmaceutically acceptable salt thereof, or a solvate of the pharmaceutically acceptable salt thereof;

I

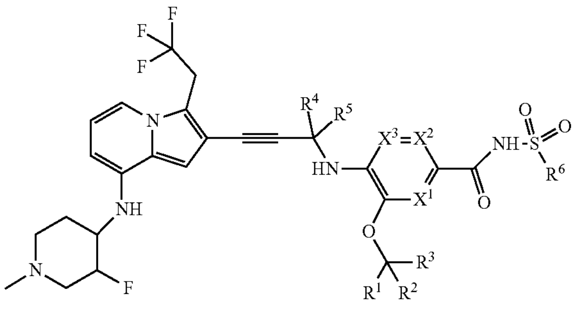

wherein $X^1$, $X^2$, and $X^3$ are each independently selected from CH and N;

$R^1$, $R^2$, $R^3$, $R^4$, and $R^5$ are each independently selected from hydrogen and deuterium;

$R^6$ is $-(CH_2)_nR^7$;

n is 0, 1, 2, or 3;

$R^7$ is selected from $C_1$-$C_6$ alkyl, deuterated $C_1$-$C_6$ alkyl, $C_1$-$C_6$ haloalkyl, and $C_3$-$C_6$ cycloalkyl.

2. The compound of formula I, the isotope-labeled compound thereof, the solvate thereof, the pharmaceutically acceptable salt thereof, or the solvate of the pharmaceutically acceptable salt thereof according to claim 1, wherein the compound of formula I is represented by formula Ia;

Ia

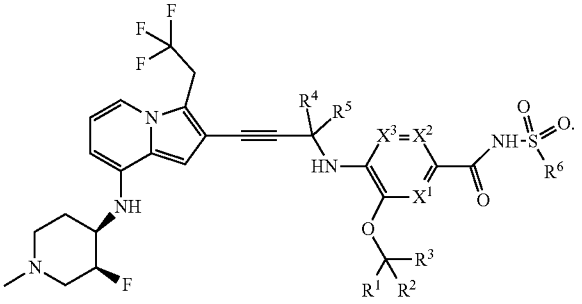

3. The compound of formula I, the isotope-labeled compound thereof, the solvate thereof, the pharmaceutically acceptable salt thereof, or the solvate of the pharmaceutically acceptable salt thereof according to claim 1, wherein $X^1$ is N; $X^2$ is CH or N; $X^3$ is CH;

or, $X^1$ is N; $X^2$ and $X^3$ are CH.

4. The compound of formula I, the isotope-labeled compound thereof, the solvate thereof, the pharmaceutically acceptable salt thereof, or the solvate of the pharmaceutically acceptable salt thereof according to claim 1, wherein $R^6$ is $-(CH_2)_nR^7$;

n is 0 or 1;

$R^7$ is selected from $C_1$-$C_3$ alkyl, deuterated $C_1$-$C_3$ alkyl, $C_1$-$C_3$ haloalkyl, and $C_3$-$C_6$ cycloalkyl.

5. The compound of formula I, the isotope-labeled compound thereof, the solvate thereof, the pharmaceutically acceptable salt thereof, or the solvate of the pharmaceutically acceptable salt thereof according to claim 1, wherein $R^6$ is $-(CH_2)_nR^7$;

n is 0 or 1;

$R^7$ is selected from $-CH_3$, $-CD_3$, $-CF_3$, and cyclopropyl.

6. The compound of formula I, the isotope-labeled compound thereof, the solvate thereof, the pharmaceutically acceptable salt thereof, or the solvate of the pharmaceutically acceptable salt thereof according to claim 1, wherein $R^1$, $R^2$, and $R^3$ are deuterium; $R^4$ and $R^5$ are hydrogen;

or, $R^1$, $R^2$, and $R^3$ are hydrogen; $R^4$ and $R^5$ are deuterium.

7. The compound of formula I, the isotope-labeled compound thereof, the solvate thereof, the pharmaceutically acceptable salt thereof, or the solvate of the pharmaceutically acceptable salt thereof according to claim 1, wherein formula I is formula Ib or Ic;

Ib

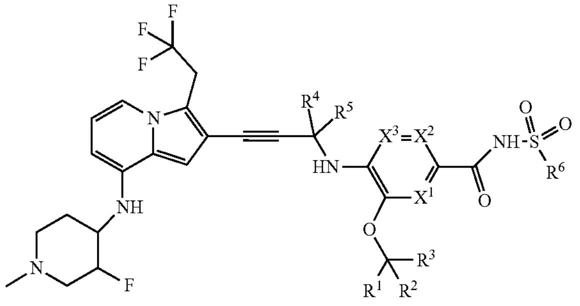

Ic

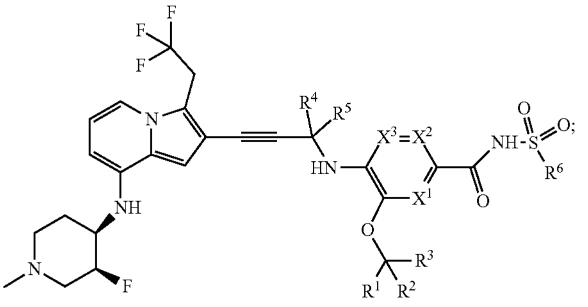

wherein in formulas Ib and Ic,

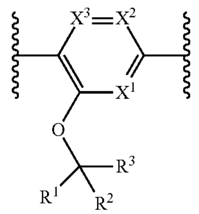

is

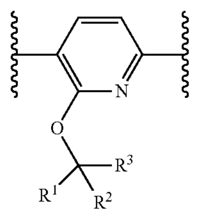

or

-continued

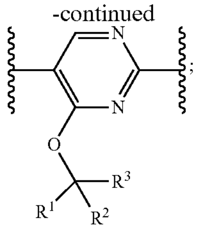

$R^1$, $R^2$, $R^3$, $R^4$, and $R^5$ are each independently selected from hydrogen and deuterium;

$R^6$ is —$(CH_2)_nR^7$;

n is 0 or 1;

$R^7$ is selected from $C_1$-$C_6$ alkyl, $C_1$-$C_6$ haloalkyl, and $C_3$-$C_6$ cycloalkyl.

8. The compound of formula I, the isotope-labeled compound thereof, the solvate thereof, the pharmaceutically acceptable salt thereof, or the solvate of the pharmaceutically acceptable salt thereof according to claim 7, wherein in formulas Ib and Ic,

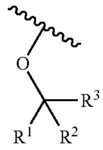

is selected from —$OCH_3$ and —$OCD_3$;

$R^4$ and $R^5$ are selected from hydrogen;

$R^6$ is —$(CH_2)_nR^7$; n is 0 or 1; $R^7$ is selected from —$CH_3$, —$CD_3$, —$CF_3$, and cyclopropyl.

9. The compound of formula I, the isotope-labeled compound thereof, the solvate thereof, the pharmaceutically acceptable salt thereof, or the solvate of the pharmaceutically acceptable salt thereof according to claim 1, wherein the compound of formula I is selected from the following compounds:

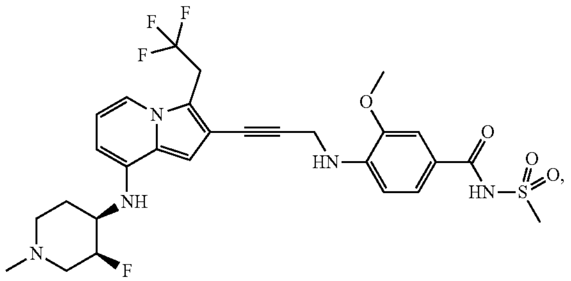

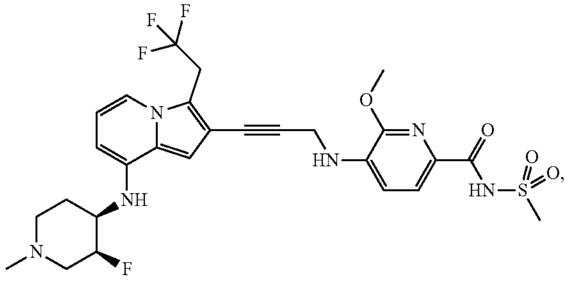

-continued

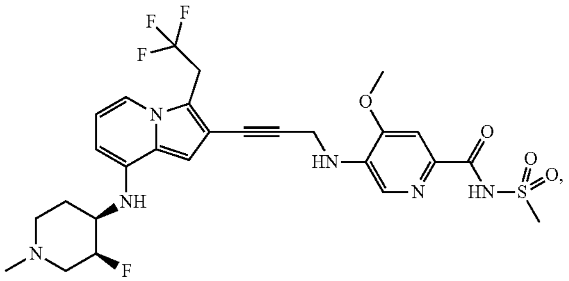

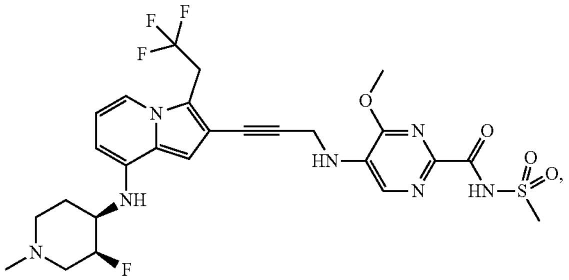

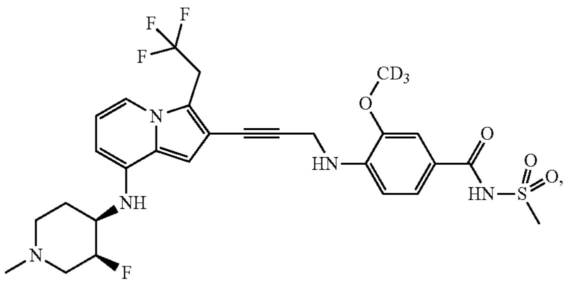

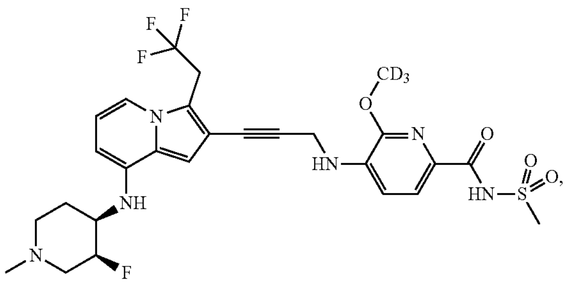

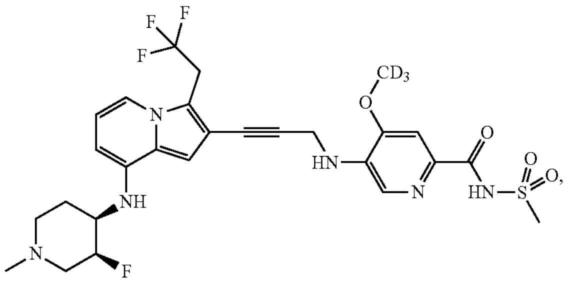

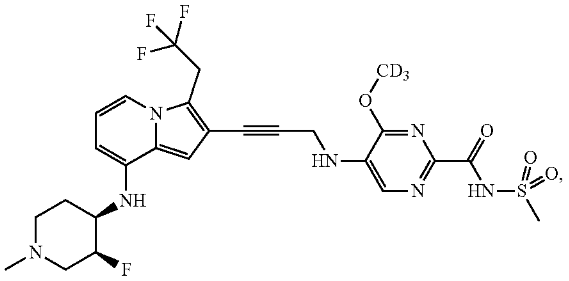

-continued
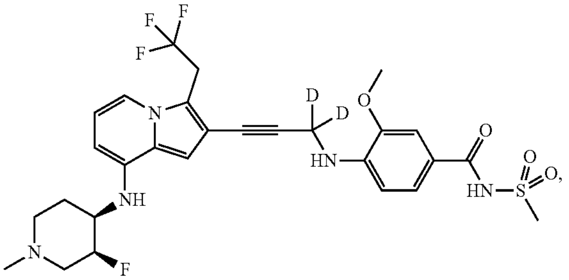
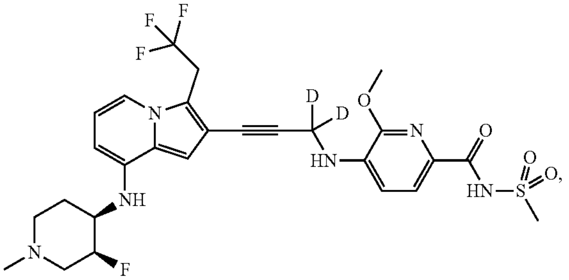
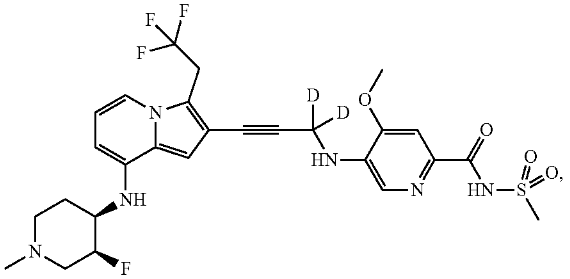
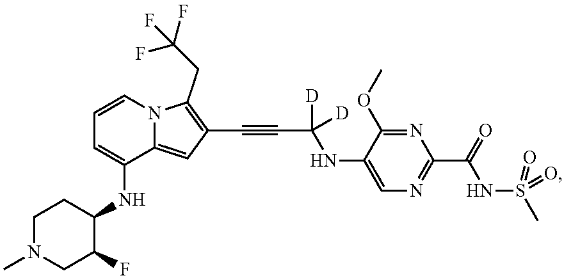
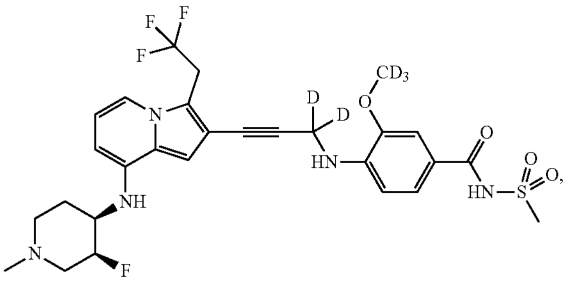
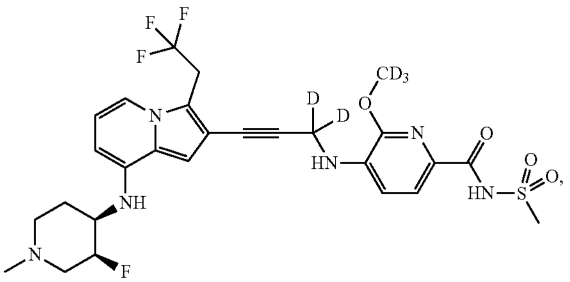
-continued
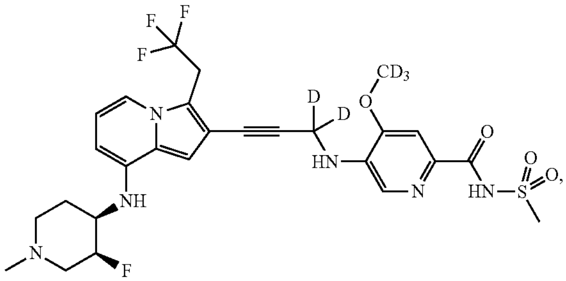
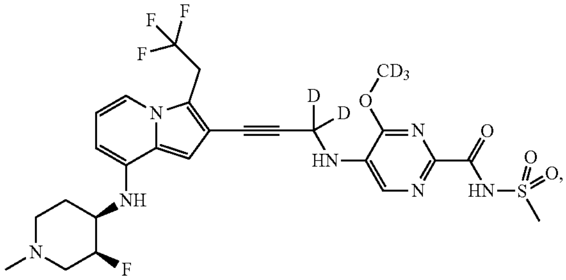
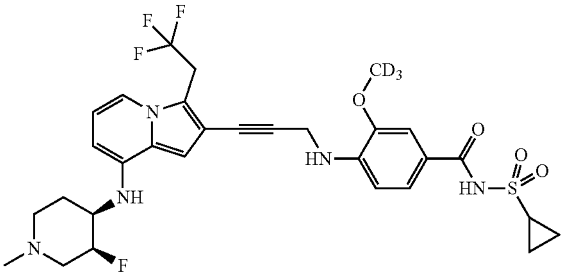
,
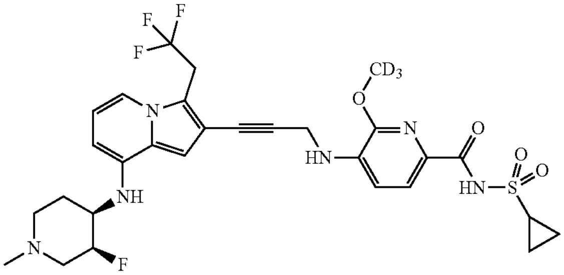
,
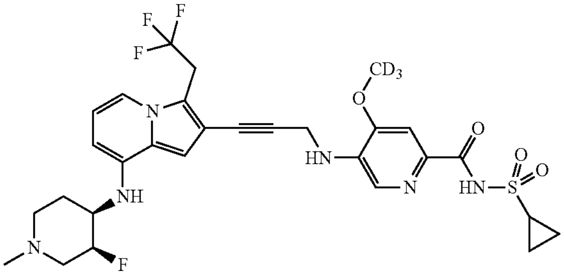
,
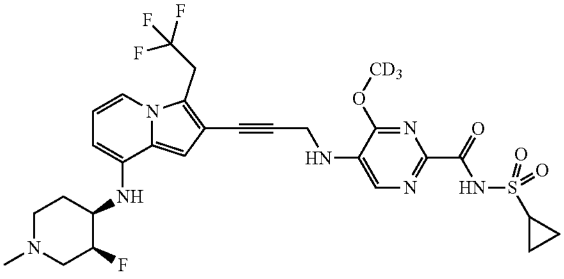
, -continued
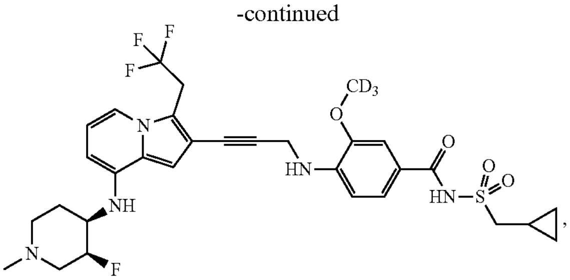
,
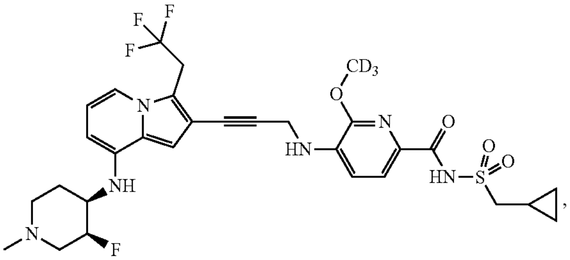
,
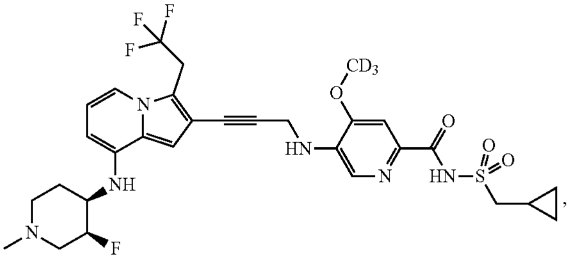
,
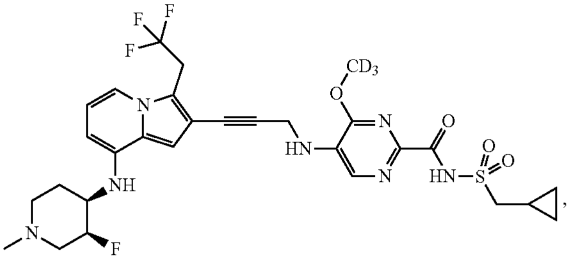
,
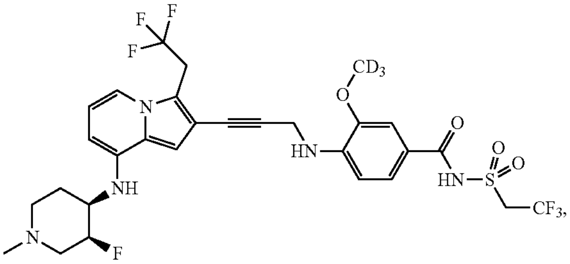
,
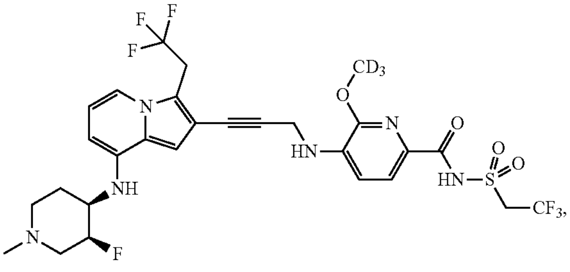
,
-continued
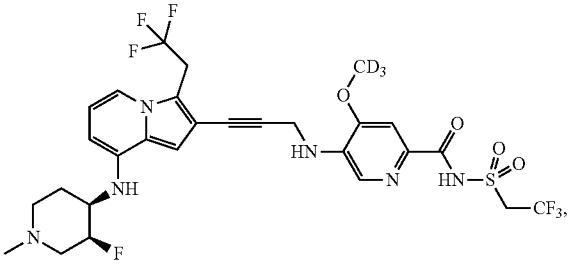
,
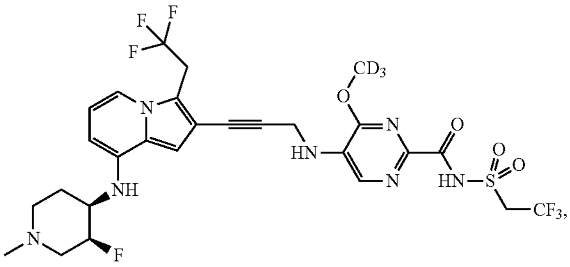
,
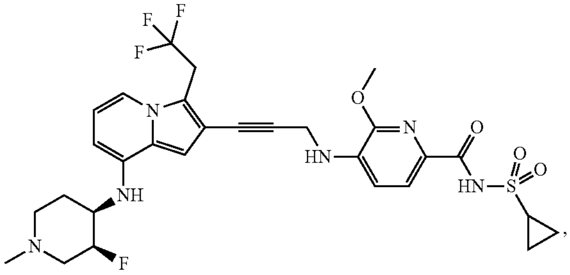
,
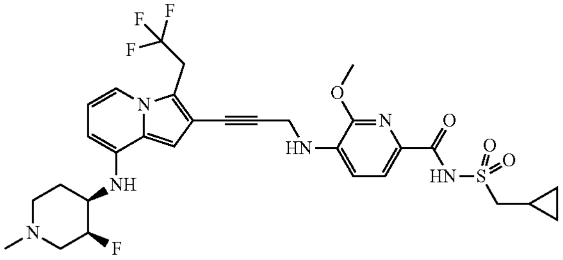
,
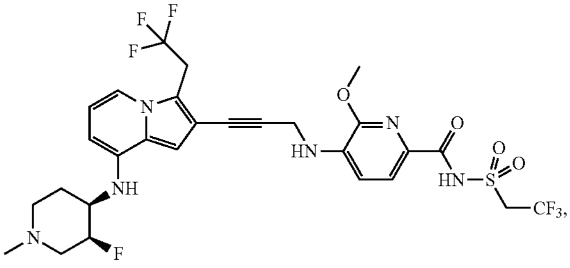
,
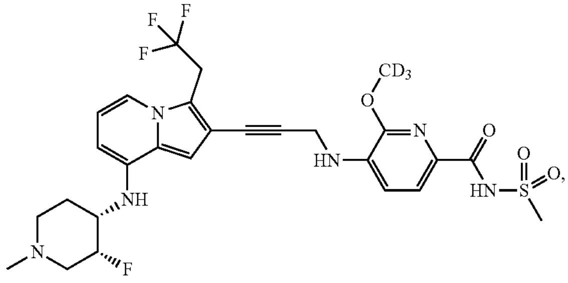
, -continued

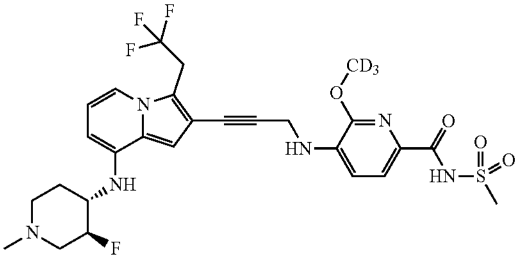

and

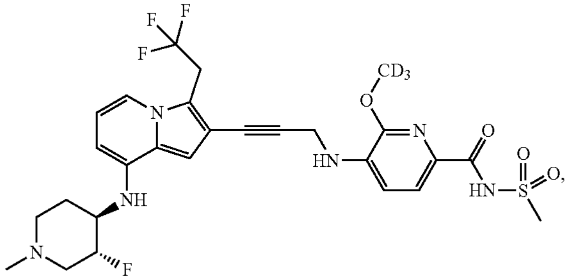 [SMILES: [2H]C([2H])([2H])Oc1nc(C(=O)NS(C)(=O)=O)ccc1NCC#Cc1cc2c(N[C@@H]3CCN(C)C[C@H]3F)cccn2c1CC(F)(F)F]

an enantiomer thereof, or a mixture of the two in any ratio.

10. A pharmaceutical composition comprising the compound of formula I, the isotope-labeled compound thereof, the solvate thereof, the pharmaceutically acceptable salt thereof, or the solvate of the pharmaceutically acceptable salt thereof according to claim 1, and a pharmaceutical excipient.

11. A method for promoting the binding of p53 Y220C mutants with DNA, wherein the method comprises: administering to a patient a therapeutically effective amount of the compound of formula I, the isotope-labeled compound thereof, the solvate thereof, the pharmaceutically acceptable salt thereof, or the solvate of the pharmaceutically acceptable salt thereof according to claim 1.

12. A method for promoting the binding of p53 Y220C mutants with DNA, wherein the method comprises: administering to a patient a therapeutically effective amount of the pharmaceutical composition according to claim 10.

13. A method for the treatment of gastric cancer, wherein the method comprises: administering to a patient a therapeutically effective amount of the compound of formula I, the isotope-labeled compound thereof, the solvate thereof, the pharmaceutically acceptable salt thereof, or the solvate of the pharmaceutically acceptable salt thereof according to claim 1.

14. A compound of formula a-11 or a-32;

a-11

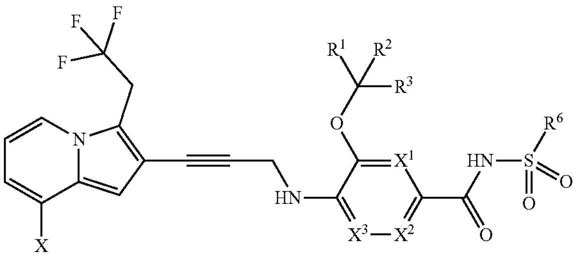

-continued a-33

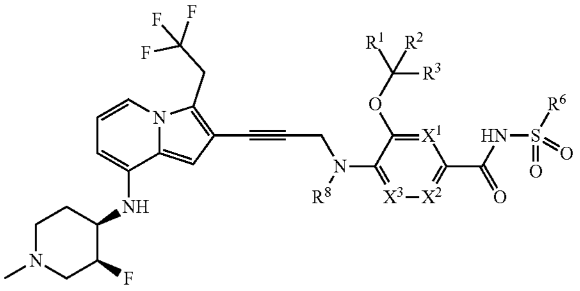

wherein X is halogen; $R^8$ is an amino protecting group;

$X^1$, $X^2$, and $X^3$ are each independently selected from CH and N;

$R^1$, $R^2$, $R^3$, $R^4$, and $R^5$ are each independently selected from hydrogen and deuterium;

$R^6$ is $-(CH_2)_nR^7$, n is 0, 1, 2, or 3;

$R^7$ is selected from $C_1$-$C_6$ alkyl, deuterated $C_1$-$C_6$ alkyl, $C_1$-$C_6$ haloalkyl, and $C_3$-$C_6$ cycloalkyl.

15. The compound of formula a-11 or a-32 according to claim 14, wherein the compound of formula a-11 or a-32 is any one of the following compounds;

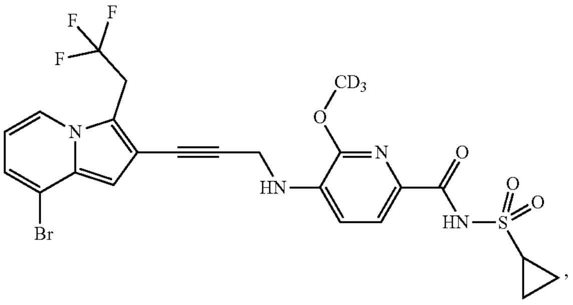

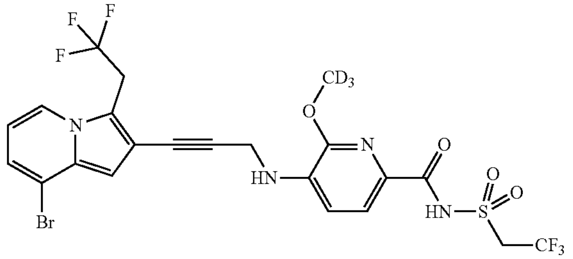

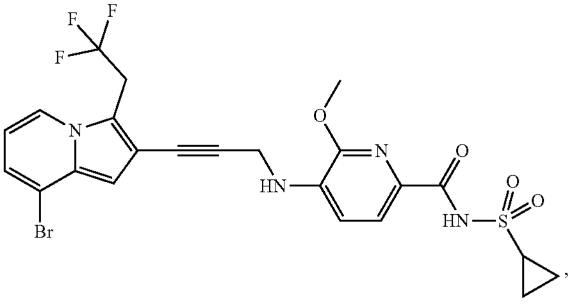

-continued
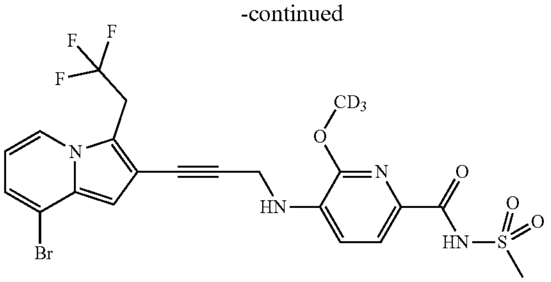
or
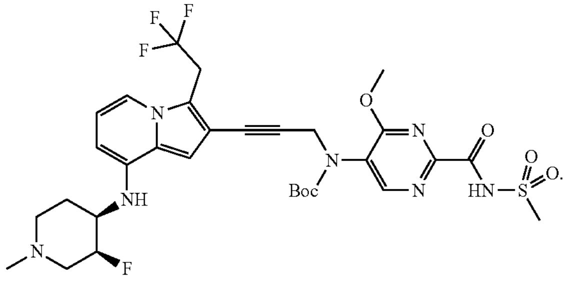
.
* * * * *

SEQUENCE LISTING

```
Sequence total quantity: 1
SEQ ID NO: 1          moltype = DNA  length = 26
FEATURE               Location/Qualifiers
source                1..26
                      mol_type = other DNA
                      organism = synthetic construct
SEQUENCE: 1
attaggcatg tctaggcatg tctagg                                 26
```